US009182592B2

(12) United States Patent
Ueno et al.

(10) Patent No.: US 9,182,592 B2
(45) Date of Patent: Nov. 10, 2015

(54) OPTICAL FILTERING DEVICE, DEFECT INSPECTION METHOD AND APPARATUS THEREFOR

(75) Inventors: Taketo Ueno, Tokyo (JP); Toshihiko Nakata, Tokyo (JP); Yukihiro Shibata, Tokyo (JP); Shun'ichi Matsumoto, Tokyo (JP); Atsushi Taniguchi, Tokyo (JP); Hiroshi Toshiyoshi, Yokohama (JP); Takuya Takahashi, Mitaka (JP); Kentaro Motohara, Koganei (JP)

(73) Assignees: HITACHI, LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 3 days.

(21) Appl. No.: 13/983,310

(22) PCT Filed: Feb. 3, 2012

(86) PCT No.: PCT/JP2012/052555

§ 371 (c)(1),
(2), (4) Date: Feb. 25, 2014

(87) PCT Pub. No.: WO2012/105705

PCT Pub. Date: Aug. 9, 2012

(65) Prior Publication Data

US 2014/0160471 A1  Jun. 12, 2014

(30) Foreign Application Priority Data

Feb. 4, 2011 (JP) .................... PCT/JP2011/052426

(51) Int. Cl.
*G01N 21/00* (2006.01)
*G02B 26/02* (2006.01)
(Continued)

(52) U.S. Cl.
CPC ............ *G02B 26/02* (2013.01); *G01N 21/9501* (2013.01); *G01N 21/956* (2013.01)

(58) Field of Classification Search
CPC .. G02B 26/02; G02B 26/023; G02B 27/0172; G02B 26/0833; G02B 27/017; G02B 2027/0127; G02B 2027/014; G02B 2027/0147; G02B 27/0101; G02B 27/2214; G02B 27/225; G02B 5/201; G02B 5/3016; G02B 5/30
See application file for complete search history.

(56) References Cited

U.S. PATENT DOCUMENTS 5,463,459 A   10/1995  Morioka et al.
5,570,180 A *  10/1996  Nagai ........................... 356/330
(Continued)

FOREIGN PATENT DOCUMENTS

JP        9-159937        6/1997
JP        2000-74648      3/2000
(Continued)

OTHER PUBLICATIONS

Takuya Takahashi et al. Electrostatically Addressable Gatefold Micro-Shutter Arrays for Astronomical Infrared Spectrograph, Asia-Pacific Conference of Transducers and Micro-Nano Technology—APCOT 2006.
(Continued)

*Primary Examiner* — Michael P Stafira
(74) *Attorney, Agent, or Firm* — Baker Botts L.L.P.

(57) ABSTRACT

An optical filtering device and an optical inspection apparatus for detecting a defect in a high sensitivity using an optical filtering device which includes a shutter array formed in a two-dimensionally on an optically opaque thin film produced on a SOI wafer and the SOI wafer is removed at portions thereof on the lower side of the shutter patterns to form perforation portions while working electrodes are formed at the remaining portion of the SOI wafer, a glass substrate having electrode patterns formed on the surface thereof and having the shutter array mounted thereon, and a power supply section for supplying electric power to the electrode patterns formed on the glass substrate and the working electrodes of the SOI wafer. And the working electrodes is controlled to cause the shutter patterns to carry out opening and closing movements with respect to the perforation portions to carry out optical filtering.

11 Claims, 64 Drawing Sheets

(51) Int. Cl.
*G01N 21/956* (2006.01)
*G01N 21/95* (2006.01)

(56) References Cited

U.S. PATENT DOCUMENTS

| | | | |
|---|---|---|---|
| 5,784,190 A * | 7/1998 | Worley | 359/291 |
| 5,999,306 A | 12/1999 | Atobe et al. | |
| 6,201,633 B1 * | 3/2001 | Peeters et al. | 359/296 |
| 7,002,677 B2 | 2/2006 | Bevis et al. | |
| 7,677,742 B2 | 3/2010 | Hillmer et al. | |
| 2004/0016896 A1 * | 1/2004 | Almogy et al. | 250/559.45 |
| 2004/0160599 A1 | 8/2004 | Hamamatsu et al. | |
| 2004/0207287 A1 | 10/2004 | Akagawa | |
| 2005/0018179 A1 | 1/2005 | Bevis et al. | |
| 2006/0012781 A1 * | 1/2006 | Fradkin et al. | 356/237.5 |
| 2006/0068568 A1 | 3/2006 | Yanase | |
| 2009/0290168 A1 | 11/2009 | Hamamatsu et al. | |
| 2009/0323054 A1 | 12/2009 | Hamamatsu et al. | |

FOREIGN PATENT DOCUMENTS

| | | |
|---|---|---|
| JP | 2000-352943 A | 12/2000 |
| JP | 2002-287045 | 10/2002 |
| JP | 2003-83907 | 3/2003 |
| JP | 2003-98113 | 4/2003 |
| JP | 2003-271927 | 9/2003 |
| JP | 2004-170111 | 6/2004 |
| JP | 2004-184142 A | 7/2004 |
| JP | 2008-519245 A | 6/2008 |

OTHER PUBLICATIONS

Wolker Viereck et al. Large-area applications of optical MEMS: micromirror arrays guide daylight, optimize indoor illumination, Photonik International 2009/2.

* cited by examiner

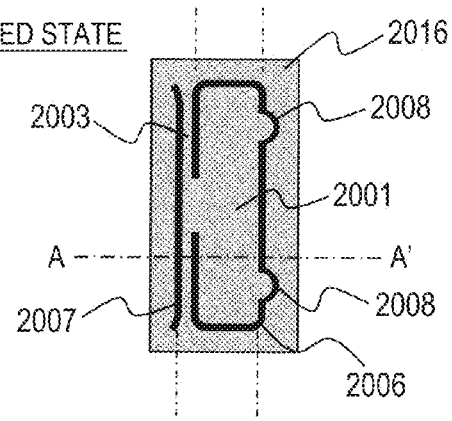
FIG. 2B CLOSED STATE
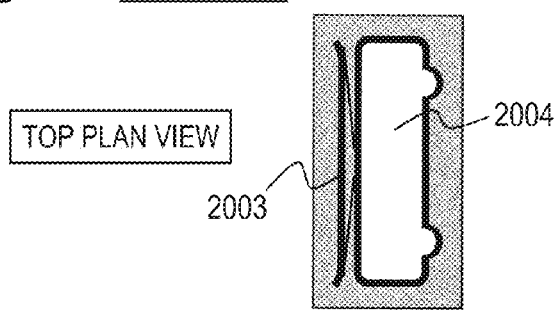
FIG. 2C OPEN STATE
TOP PLAN VIEW
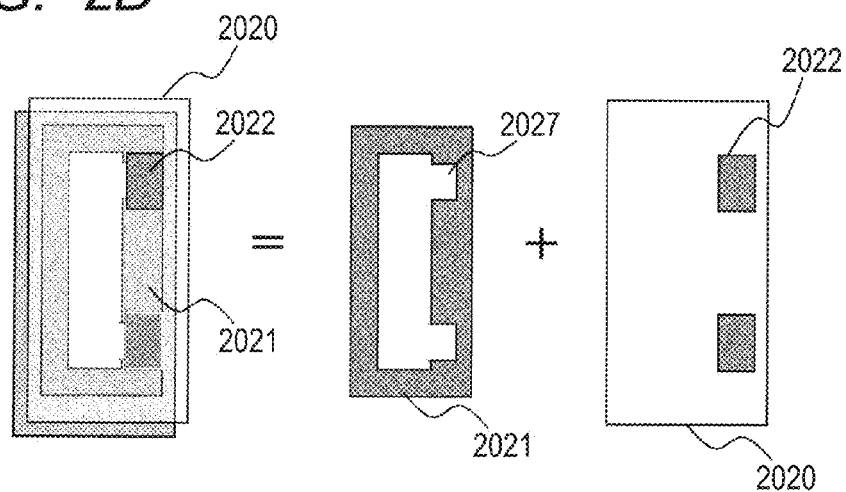
FIG. 2D

TOP PLAN VIEW

BOTTOM PLAN VIEW

Y SECTION

X SECTION

SHUTTER IN LATCHED STATE

UNIT [V]

| | WIRING LINE POTENTIAL | SHUTTER POTENTIAL | POTENTIAL DIFFERENCE $|\Delta V_2|$ | SHUTTER STATE | CORRESPONDENCE TO FIG. 8F |
|---|---|---|---|---|---|
| S1101 | $V_{B1} = -5$ | $V_{B1} = -5$ | 0 | CLOSED | S801 |
| S1102 | $V_{A1} = +5$ | $V_{B1} = -5$ | 10 | CLOSED | S802 |
| S1103 | $V_{A1} = +5$ | $V_{B2} = -20$ | 25 | CLOSED | |
| S1104 | $V_{A2} = +20$ | $V_{B2} = -20$ | 40 | LATCHED CLOSED | S803 |
| S1105 | $V_{A1} = +5$ | $V_{B2} = -20$ | 25 | LATCHED CLOSED | S804 |
| S1106 | $V_{A1} = +5$ | $V_{B1} = -5$ | 10 | LATCHED CLOSED | |
| S1107 | $V_{B1} = -5$ | $V_{B1} = -5$ | 0 | CLOSED | S801 |

| TIME<br>SWITCH | 0 TO $t_0$ | $t_0$ TO $2 \times t_0$ |
|---|---|---|
| 5311 | 5303 | 5303 |
| 5312 | 5304 | 5303 |
| 5313 | 5303 | 5304 |
| 5331 | 5302 | 5302 |
| 5332 | 5302 | 5302 |
| 5333 | 5301 | 5302 |
| 5334 | 5302 | 5301 |

FIG. 15C
| TIME SWITCH | 0 TO $t_1$ | $t_1$ TO $2\times t_1$ | $2\times t_1$ TO $3\times t_1$ | $3\times t_1$ TO |
|---|---|---|---|---|
| 5341 | 5323 | 5323 | 5324 | 5324 |
| 5342 | 5324 | 5323 | 5324 | 5324 |
| 5343 | 5323 | 5323 | 5323 | 5324 |
| 5351 | 5322 | 5322 | 5322 | 5322 |
| 5352 | 5322 | 5322 | 5322 | 5322 |
| 5353 | 5322 | 5322 | 5321 | 5322 |
| 5354 | 5321 | 5322 | 5322 | 5322 |
FIG. 16A
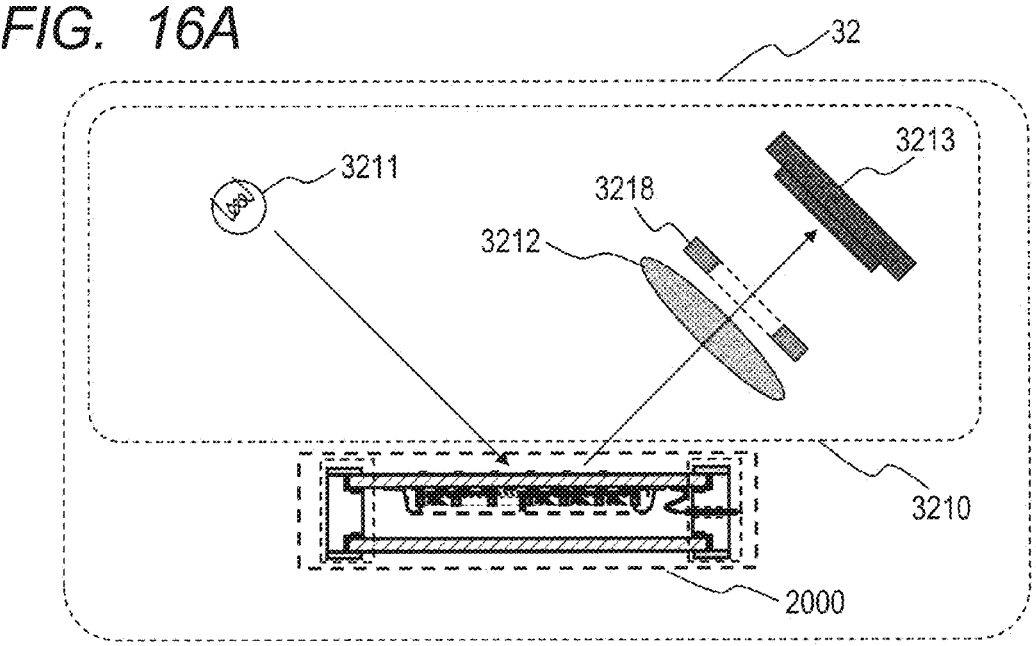
FIG. 16B
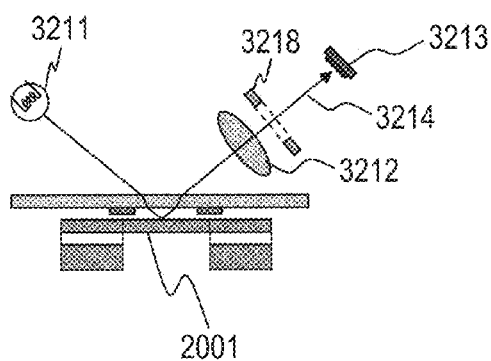

①: S1102  ④: S1105
②: S1103  ⑤: S1106
③: S1104

OPTICAL FILTERING DEVICE, DEFECT INSPECTION METHOD AND APPARATUS THEREFOR

BACKGROUND

The present invention relates to an optical filtering device which blocks light to a desired region from within incident light while it transmits the remaining light therethrough, and a method of and an apparatus for comparing an optical image of an inspection object article and a reference image with each other using the optical filtering device and detecting a fine pattern defect or a foreign article from the difference between the images. More particularly, the present invention relates to a defect inspection method for carrying an appearance inspection of a semiconductor wafer, a photo mask, a liquid crystal device and so forth and an apparatus for the defect inspection method.

In fabrication of semiconductor devices, a substrate (wafer) on which a semiconductor device is to be formed is processed by up to several hundred fabrication steps to obtain a product. At the steps, a foreign article sticks to a substrate (wafer) or a pattern defect is caused by step dispersion in pattern formation or the like, and they make a semiconductor device defective. Further, in a defect inspection system for a semiconductor device, as miniaturization of patterns progresses, it is demanded not only to detect a finer defect or foreign article but also to detect an interesting object (DOI (Defect of Interest)). Simultaneously, needs for classification of various kinds of DOIs or defects which are not desired to detect are growing. To satisfy such needs, a defect inspection apparatus has been and is being developed, fabricated and sold in recent years which includes a plurality of detection optical systems and image processing systems (hereinafter referred to as detection head) and uses detection signals of the detection optical systems to achieve increase of the types of defects which can be detected and improvement in defect detection performance. Such a defect inspection apparatus as described above has been and is being applied to a semiconductor production line.

The defect detection apparatus for a semiconductor device is used to detect a pattern defect or a foreign article which occurs at such a step as, for example, a lithography step, a film-forming step or an etching step by inspecting the surface of a substrate after completion of the step and issue a cleaning carrying out instruction for the apparatus for the step. Or, the defect detection apparatus is used to detect, at an early stage, occurrence of a defective article by feeding a substrate, which is in a state in which it already suffers from a fatal defect, to succeeding steps.

A substrate for which a predetermined process has been carried out at a preceding step and on which a semiconductor device is being formed is loaded into an inspection apparatus. An image of the surface of the substrate (wafer) on which a semiconductor device is being formed is picked up and acquired, and such a defect signal decision threshold value defect decision process as disclosed in JP-A-2003-83907 (Patent Document 1), JP-A-2003-98113 (Patent Document 2), JP-A-2003-271927 (Patent Document 3) or the like is carried out based on the image thereby to carry out a defect decision. Then, the number of defects on the substrate and so forth are outputted.

If the detected defect number Nt is smaller than a defect number threshold value Nc set in advance, then the substrate (wafer) is sent as it is to a next step. If the defect number Nt is greater than the defect number threshold value Nc, then a cleaning carrying out instruction of the preceding step apparatus is issued, whereafter propriety of regeneration of the substrate is decided. If it is decided that the substrate can be regenerated, then the substrate is cleaned at a cleaning step and then is sent to the next step through the inspection step again.

In the substrate (wafer) which is an inspection object article and on which a semiconductor device is being formed, portions 1 and 1' (hereinafter referred to each as die) having a same pattern are juxtaposed regularly as shown in FIG. 4. The defect inspection method and the defect inspection apparatus to which the present invention is directed compare images at positions in adjacent dies which have same inter-die coordinates with each other and carry out defect detection decision based on a difference between the images.

The semiconductor defect inspection system is ready for detection of a finer DOI and a requirement for a high speed inspection by adopting the following technique in addition to the technique described above. In particular, diffracted light from patterns on a semiconductor device is blocked using a spatial filter so that it may not be reflected on the inspection image to detect a foreign article or a defect on the semiconductor device with a high sensitivity as disclosed, for example, in JP-A-2000-105203 (Patent Document 4).

However, with such a spatial filter configured by juxtaposition of bar-like plates as disclosed in the above-mentioned patent document, it is difficult to block, for example, diffracted light of a plurality of pitches formed on the Fourier transform plane and caused by the presence of a plurality of pitches of patterns formed on a semiconductor device. Further, if a light source having a plurality of illumination wavelengths or a plurality of laser light sources of different oscillation wavelengths are used to illuminate a semiconductor device, then even if the patterns have a single pitch, diffracted light of a plurality of pitches is generated on the Fourier transform plane and it is difficult to block such diffracted light. Further, even if such light blocking is possible, the light blocking region becomes excessively great and this results in substantial reduction in size of apertures. This gives rise to a problem that the defect detection sensitivity drops.

On the other hand, if a light source having a plurality of illumination waveforms or a plurality of laser light sources having different oscillation wavelengths are used to illuminate a semiconductor device, then even if the patterns have a single pitch, it is similarly difficult to block light except a case in which the ratio of the plural light wavelengths and the pattern pitch on a semiconductor device have a special relationship. Or, even if it is possible to block light, the defect detection sensitivity drops from a similar reason.

From such reasons as described above, a defect inspection method which uses not a spatial filter wherein bar-like plates are arrayed one-dimensionally but a spatial filter having devices arrayed two-dimensionally has been proposed.

For example, as a two-dimensional optical filtering technique which can block light to an arbitrary region, a PLZT filter and a liquid crystal filter which use double refraction are available. However, since the former has a wavelength dependency in working characteristic thereof, filtering of illumination light of a plurality of wavelengths is difficult. The latter can detect only scattered light of particular polarized light, and scattered light components polarized in a direction perpendicular to the polarization direction are blocked. Therefore, depending upon the polarization characteristic of scattered light from a defect, the detection sensitivity drops significantly. Further, the latter has such a subject that the durability when ultraviolet rays are irradiated thereon is low and gives rise to a problem that the light source to be used for inspection is limited.

Therefore, development wherein a device in the form of a two-dimensional array which does not utilize a double refraction effect is utilized as a spatial filter is being progressed. Among such devices, a device draws attention which uses a MEMS (Micro Electro Mechanical System) technology because the ratio in transmission light intensity upon ON/OFF switching (light transmission ratio) thereof is high.

As a device for separating an arbitrary region in which the MEMS technology is used and any other region, a method which uses such a two-dimensional DMD (Digital Micromirror Device) as disclosed in JP-A-2004-170111 (Patent Document 5), another method which uses such a micro actuator array and micromirrors as disclosed in JP-A-2004-184564 (Patent Document 6) and a further method which uses an array of micro shutters by T. Takahashi et al. are available.

Of the methods mentioned, the former two methods, namely, the methods which use micromirrors, utilize that, if a desired potential difference is applied to different portions of a device to change the direction of the mirrors, then the direction in which light irradiated toward the mirrors is reflected changes.

PRIOR ART DOCUMENTS

Patent Documents

Patent Document 1: JP-A-2003-83907
Patent Document 2: JP-A-2003-98113
Patent Document 3: JP-A-2003-271927
Patent Document 4: JP-A-2000-105203
Patent Document 5: JP-A-2004-170111
Patent Document 6: JP-A-2004-184564
Patent Document 7: JP-A-2000-352943
Patent Document 8: JP-A-2010-2406
Patent Document 9: JP-A-2006-100596

Non-Patent Documents

Non-Patent Document 1: T. Takahashi et al., "Electrostatically Addressable Gatefold Micro-shutter Arrays for Astronomical Infrared Spectrograph," Proc. Asia Pacific Conference on Transducers and Micro-Nano Technology, 2006, Singapore Non-Patent Document 2: "Step Pattern Formation on Si Vicinal Surfaces with Two Coexisting Structures," M. Uwaha, http://www.ims.nus.edu.sg/Programs/nanoscale/files/muwahal.pdf

SUMMARY OF THE INVENTION

The optical filtering technique described above which uses a device which changes the reflection direction of light using micromirrors has no problem if an image is obtained based on a result of ON/OFF switching. However, if the device is inserted as a spatial filter into the Fourier transform plane, then since the surface of mirrors is moved, occurrence of aberrations is inevitable in principle. Thus, since the image formation degradation and a picked up image indicates an out-of-focus state, there is the tendency that the defect detection performance decreases.

Meanwhile, since the micro shutter array is used as a device of the transmission type whereas the shutters carry out only opening and closing movements, different from an alternative case in which light is reflected using mirrors, no aberrations occur. However, in order to form the shutters and in order to prevent malfunction by sticking, it is necessary to etch a substrate to form an incision. Therefore, since light leaks through the incision, the micro shutter array has a problem that the light blocking ratio drops.

Further, with the micro shutter array, if a high voltage is applied to a shutter main body or a wiring line on a glass substrate, then since the shutter array and the wiring patterns on the glass substrate are positioned closely to each other, insulation breakdown sometimes occurs and causes an accident such as discharge, resulting in damage to the shutter array main body. Further, different from a common switch array of column and row directions, only if shutter opening/closing movements are determined successively for crossing points, an arbitrary shutter cannot be moved to open or close. Thus, it is necessary to lay wiring lines for the individual shutters to control the shutters to open or close or to carry out complicated simultaneous control of signal generators and signals for the individual wiring lines.

The present invention solves the problems of the prior art described above and provides an optical filtering device wherein an arbitrary shutter can be opened and closed and besides the light blocking ability when the shutter is closed is high.

Further, the present invention solves the problems of the prior art described above and provides an inspection method and an inspection apparatus of the optical type which are high in defect detection sensitivity using an optical filtering device wherein an arbitrary shutter can be opened and closed and besides the light blocking ability when the shutter is closed is high.

Means for Solving the Problems

According to the present invention, in order to solve the problems described above, an optical filtering device is configured as a system which includes the following means:
(1): a MEMS shutter array electrically connected in one direction,
(2): a glass substrate having wiring patterns formed thereon in a state in which they conduct in a direction perpendicular to (1),
(3): means for positioning and fixing (1) and (2) to each other,
(4): controlling power supply hardware for driving (1), and
(5): a procedure for controlling operation of (4).
It is to be noted that the optical filtering device preferably has the following features:
(6): a transparent substrate and a frame combined such that (1) is positioned on the inner side and light can pass therethrough, and
(7): a procedure for sealing (1) using (2) and (6) as outer walls and removing moisture from the inside.

Further, the present invention provides an inspection method and an inspection apparatus of the optical type which uses a spatial (optical) filtering device wherein an arbitrary shutter can be opened and closed and besides the light blocking ratio is high. In particular, in the present invention, in order to achieve the subjects described hereinabove, the inspection method and the inspection apparatus are configured as a system which includes the following means.
(A): a light source such as a laser and an illumination optical system,
(B): an observation optical system for a Fourier transform plane which can measure a diffracted light distribution from an inspect object sample,
(C): a spatial filtering device to which a MEMS shutter array which can block light to an arbitrary region and exhibits a high light blocking ratio is applied, (D): one or a plurality of defect detection optical systems and optical detectors having (B) and (C) for detecting scattered light, and (E): an image processing system for detecting a defect existing in the proximity of the sample of the inspection object sample using (D).

In particular, according to the present invention, in order to solve the problems described hereinabove, there is provided an optical filtering device including a shutter array wherein shutter patterns are formed in a two-dimensionally arrayed relationship on an optically opaque thin film produced on a SOI wafer and the SOI wafer is removed at portions thereof on the lower side of the shutter patterns to form perforation portions while working electrodes are formed at the remaining portion of the SOI wafer, a glass substrate having electrode patterns formed on the surface thereof and having the shutter array mounted thereon, and a power supply section for supplying electric power to the electrode patterns formed on the glass substrate and the working electrodes of the SOI wafer, wherein the electric power to be supplied from the power supply section to the electrode patterns and the working electrodes is controlled to cause the shutter patterns formed in the two-dimensionally arrayed relationship to carry out opening and closing movements with respect to the perforation portions, and wherein the shutter patterns have a protrusion at an end portion thereof.

Further, according to the present invention, in order to solve the problems described hereinabove, there is provided a defect inspection apparatus including illuminator which illuminates an inspection object substrate, detection optical unit including an optical filtering device which blocks scattered light from a portion of the inspection object substrate which is not desired to be detected as a defect, and detects scattered light from the portion of the inspection object substrate which is not blocked by the optical filtering device, signal processing unit which processes a signal obtained by the detection of the scattered light by the detection optical unit to detect a defect of the inspection object substrate, and outputting unit which outputs information of the defect detected by the signal processing unit, wherein, the optical filtering device of the defect inspection apparatus including a shutter array which has shutter patterns formed in a two-dimensionally arrayed relationship on an optically opaque thin film produced on a SOI wafer and working electrodes formed on remaining portion of the SOI wafer which is removed at portions lower sides of the shutter patterns to form perforation portions, a glass substrate having electrode patterns formed on the surface thereof and having the shutter array mounted thereon, and a power supply section for supplying electric power to the electrode patterns formed on the glass substrate and the working electrodes of the SOI wafer, wherein the electric power to be supplied from the power supply section to the electrode patterns and the working electrodes being controlled to cause the shutter patterns formed in the two-dimensionally arrayed relationship to carry out opening and closing movements with respect to the perforation portions.

Further, according to the present invention, in order to solve the problems described hereinabove, there is provided a defect inspection method including illuminating an inspection object substrate, blocking with an optical filtering device, scattered light from a portion of the inspection object substrate which is not desired to be detected as a defect among scattered light from the illumination inspection object substrate, and detecting scattered light which is not blocked by the optical filtering device, processing a signal obtained by the detection of the scattered light to detect a defect of the inspection object substrate with a processor, and outputting information of the detected defect from an outputting unit, wherein in the step of blocking, the scattered light from the portion of the inspection object substrate which is not desired to be detected as a defect being carried out such that controlling electric power to be supplied to working electrode patterns to drive shutter patterns, which can carry out opening and closing movements with respect to perforation portions, to close a desired one or more of the shutter patterns to block the scattered light, the shutter patterns are formed in a two-dimensionally arrayed relationship on an optically opaque thin film on a SOI wafer as a shutter array and the working electrodes are formed on the SOI wafer at perforation portions which are processed by removing portions of the SOI wafer which are under portions lower sides of the shutter patterns, and the electrode patterns are formed on a surface of a glass substrate on which the shutter array is mounted.

With the invention of the present application, an optical filtering device which is electrically safe and can change the light blocking region at a high speed using a simple and easy system can be provided.

Further, with the invention of the present application, an inspection method and an inspection apparatus of the optical type which is high in defect detection sensitivity using an optical filtering device which is electrically safe and can change the light blocking region at a high speed using a simple and easy system can be provided.

BRIEF DESCRIPTION OF THE DRAWINGS

FIG. 2B is a plan view of a SOI region illustrating a closed state of the unit micro shutter.

FIG. 2C is a plan view of the SOI region in a state in which the unit micro shutter is open.

FIG. 2D shows a shape of the unit micro shutter and is a plan view of a glass substrate with wiring patterns illustrating a state in which light blocking patterns are formed on an upper face and wiring patterns are formed on a lower face of the glass substrate.

FIG. 15C is a table illustrating a state of a power supply switch for driving the micro shutter array according to the modification at different points of time.

FIG. 16A is a block diagram showing a general configuration of an optical system and an optical filtering device for confirming an open/closed state of each shutter of the optical filtering device.

FIG. 16B is a sectional view of the unit micro shutter showing a configuration wherein the closed state of a shutter is observed by the optical system.

DESCRIPTION OF THE PREFERRED EMBODIMENTS

An optical filtering device which can change a light blocking region and an optical filtering method which uses the optical filtering device according to the present invention are described with reference to the drawings.

Figure 1:
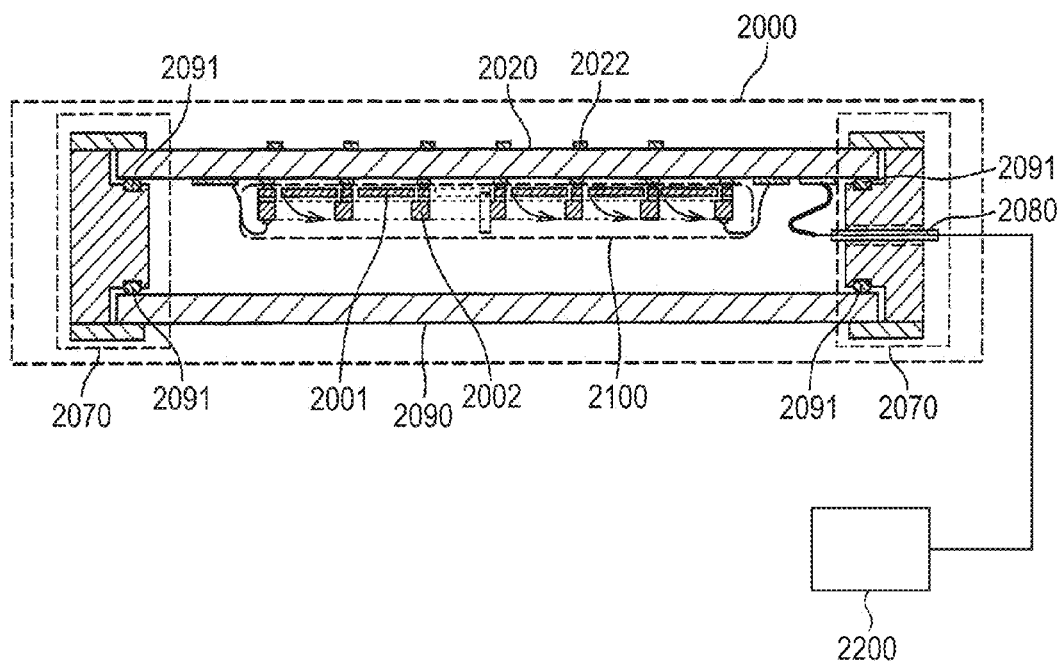
FIG. 1 is a diagram illustrating a form of an embodiment of an optical filtering device which uses a micro shutter array according to the present invention.

An example of an optical filtering device 2000 which uses a micro shutter array according to the present invention is described with reference to FIG. 1.

The optical filtering device 2000 has a micro shutter array 2100, a glass substrate 2020 with a wiring pattern on which wiring patterns 2022 are formed, and a power supply member (including a connector) 2080. When the optical filtering device 2000 operates, a high voltage of DC is applied to an electrode region. Therefore, in order to reduce the risk of occurrence of an electric shock accident by contact of a hand or the like with the electrode region while the optical filtering device 2000 has a function as a shutter array of the transmission type, the optical filtering device 2000 preferably includes a packaging member 2070 and a transmission light glass member 2090. Further, in order to prevent sticking or a failure in opening or closing action caused by moisture of the micro shutters, the packaging member 2070 preferably includes an airtightness holding member 2091 such as an O-snap ring. It is to be noted that, in order to allow the micro shutter array 2100 in the optical filtering device 2000 to carry out an opening or closing action, a power supply 2200 including a driving controlling circuit is connected to the optical filtering device 2000 through the power supply member 2080.

Description of the micro shutter array 2100 is given below with reference to FIGS. 2A to 2D.

Figure 2A:
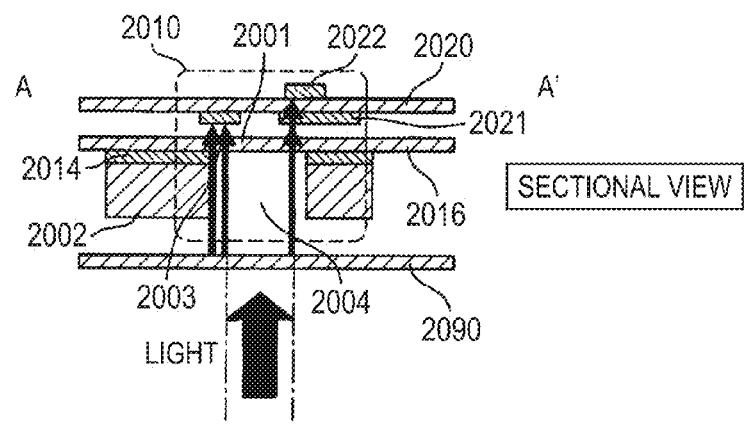
FIG. 2A is a sectional view of a unit micro shutter.

A region surrounded by a broken line 2010 in FIG. 2A represents a single micro shutter. The single micro shutter 2010 includes an optically opaque shutter 2001, a working electrode 2002, a suspension 2003, and an aperture 2004. However, also a portion, in the proximity of the shutter 2001, of a wiring pattern 2021 formed on the shutter 2001 side of the glass substrate 2020 with a wiring pattern and a portion, in the proximity of the shutter 2001, of a light blocking pattern 2022 formed on the opposite side of the glass substrate 2020 with a wiring pattern to the shutter 2001 contribute to an action of the micro shutter 2010. Therefore, in the following description, also the portions mentioned are described.

FIG. 2B is a plan view of an SOI region in a state in which the shutter 2001 of the micro shutter 2010 is closed, and FIG. 2C is a plan view in another state in which the shutter 2001 is open. FIG. 2A is a sectional view taken along line A-A of FIG. 2B. As shown in FIG. 2B, the shutter 2001 connects to the suspension 2003 in the proximity of the center of the suspension 2003 such that it is integrated with the suspension 2003. Therefore, as the suspension 2003 is twisted in a perpendicular direction to the longitudinal direction thereof, the shutter 2001 integrated therewith is opened or closed. In this state, no twist occurs with the SOI region 2016. Therefore, at portions 2003-1 and 2003-2 in the proximity of the opposite ends in the longitudinal direction of the suspension 2003 which are connecting portions between the suspension 2003 and the SOI region 2016, the variation in torsional stress caused by the twist suddenly becomes great. Consequently, the possibility that the portions in the proximity of the opposite ends of the suspension 2003 may be broken is high. Therefore, the portions in the proximity of the opposite ends of the suspension 2003 are preferably formed so as to be continuously thicker so that the torsional stress appearing in the proximity of the opposite ends of the suspension 2003 may vary moderately.

Figure 2E:
FIG. 2E is a sectional view showing a configuration of the SOI region which configures the unit micro shutter.
Figure 2F:
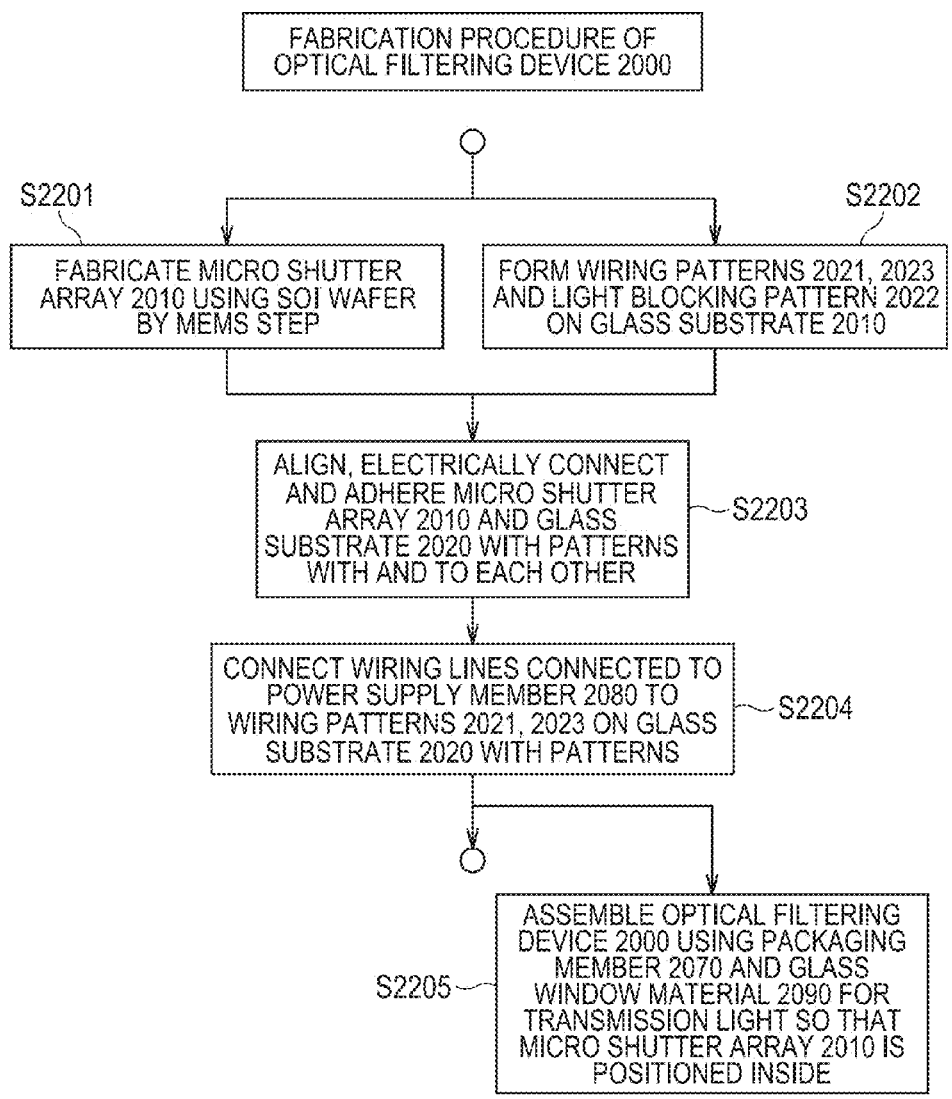
FIG. 2F is a flow chart illustrating a fabrication procedure of the optical filtering device.
Figure 2G:
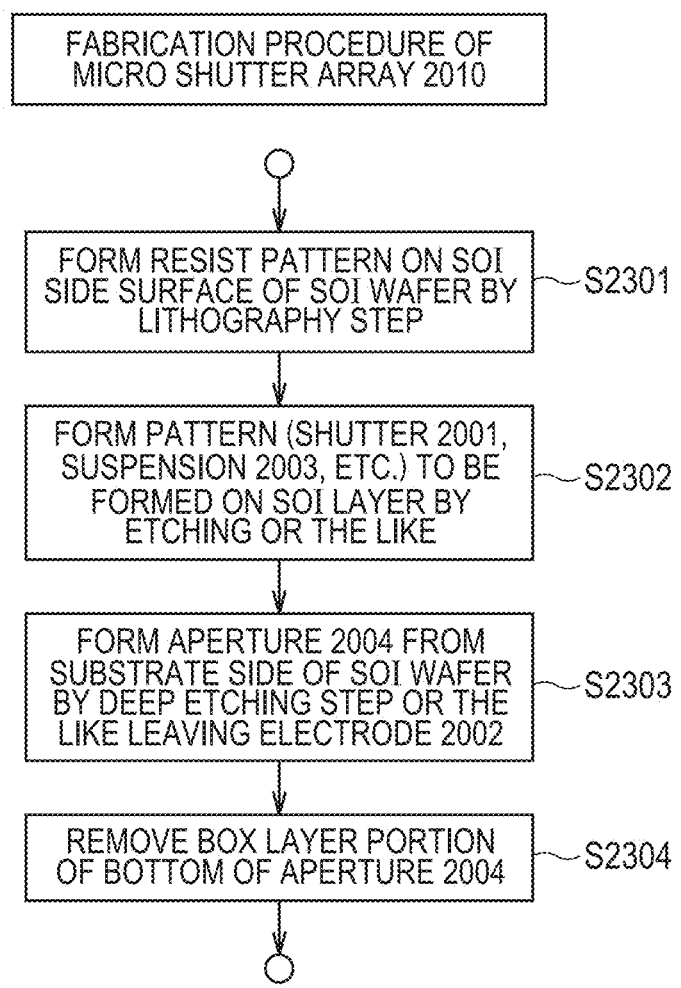
FIG. 2G is a flow chart illustrating a fabrication procedure of the micro shutter array.

Now, the single micro shutter structure and a fabrication method for the same are described with reference to FIGS. 2A, 2B and 2G.

The micro shutter array is fabricated using an SOI (Silicon on Insulator) wafer 201. The SOI wafer 201 is structured such that an oxide insulating film (BOX layer: Buried Oxide layer) 2014 and a surface Si film (hereinafter referred to as SOI region) 2016 are formed on a Si substrate 2012 as shown in FIG. 2E. The shutter 2001 and the suspension 2003 are fabricated by patterning resist of the SOI region 2016 using a technique such as lithography (S2301) and carrying out etching (S2302) to form incision portions 2006 and 2007.

Then, deep reactive-ion etching (deep RIE) is carried out from the side of the Si substrate 2012 to form the aperture 2004 while part of the Si substrate 2012 is left as the working electrode 2002 as shown in FIG. 2A (S2303). At this time, since the depth of the groove which can be etched or a groove in a state in which a face of the working electrode 2002 on the aperture 2004 side is inclined is formed depending upon the apparatus, processing by deep RIE may be carried out after the Si substrate portion is shaved thinner. Further, the SOI wafer 201 is etched from the Si substrate 2012 side to remove a portion of the BOX film 2014 on the bottom of the aperture 2004 (S2304). The micro shutter is prepared by the foregoing process.

Now, a fabrication procedure of the optical filtering device 2000 is described with reference to FIG. 2F.

An SOI wafer is processed by an MEMS procedure of a lithography or etching technique to form the micro shutter 2010 (S2201). Further, by an MEMS procedure such as a lithography or etching technique or by such a method as application, a light blocking pattern 2022 is formed on the top face of the glass substrate 2020 with a wiring pattern and wiring patterns 2021 and 2023 are formed on the bottom face of the glass substrate 2020 with a wiring pattern as shown in FIG. 2D (S2202). At this time, in order to avoid appearance of leak light, the light blocking pattern 2022 and the wiring patterns 2021 and 2023 are formed such that the positions of pattern recessed portions 2027 of the wiring pattern 2021 formed on the bottom face of the micro shutter 2010 and the light blocking patterns 2022 formed on the top face of the micro shutter 2010 are substantially in register with each other. Then, the micro shutter array 2100 and the glass substrate 2020 with a wiring pattern formed on the SOI wafer are aligned with each other and then are electrically connected and adhered to each other (S2203). Further, wiring lines connected to the power supply member 2080 are individually connected to the wiring patterns 2021 and 2023 on the glass substrate 2020 with a wiring pattern (S2204).

Although the optical filtering device 2000 may be configured in such a manner as described above, taking reduction of the risk of an electric shock accident into consideration as described above, preferably the optical filtering device 2000 is assembled (S2205) using the packaging member 2070 and the transmission light glass member 2090, more preferably in a dry atmosphere. Then, in order to reduce the influence of the external humidity, the airtightness holding member 2091 such as an O-snap print may be interposed between the packaging member 2070 and the glass substrate 2020 with a wiring pattern and transmission light glass member 2090 as shown in FIG. 1.

Now, a positional relationship between the shutter 2001 and the wiring patterns 2021 and 2023 and light blocking pattern 2022 is described.

In order to fabricate a portion to be used as the shutter 2001 and the suspension 2003 using an SOI wafer, it is necessary to form such incision portions 2006 and 2007 as shown in FIGS. 2B and 2C at an SOI region on the SOI wafer by etching or laser processing or else by EB (Electron Beam) processing. However, even in such a state in which the shutter 2001 is closed as shown in FIG. 2B, light passes through the incision portions. If light passing through the incision portions 2006 and 2007 is outputted as it is from the optical filtering device 2000, then this makes noise and makes a cause of deteriorating a performance of the optical filtering device 2000.

Therefore, in order to prevent light having passed through the incision portions 2006 and 2007 from being outputted from the optical filtering device 2000, in the optical filtering device according to the present invention, wiring patterns are formed in the following manner. In particular, wiring patterns are formed at positions on the glass substrate 2020 with a wiring pattern opposing to the incision portions 2006 and 2007 of the SOI region 2016 so that light (indicated by a thick arrow mark in FIG. 2A) having passed through the incision portions 2006 and 2007 of the SOI region 2016 are blocked.

However, since the shutter 2001 and the wiring pattern 2021 on the glass substrate 2020 with a wiring pattern may have a potential difference therebetween, the shape is devised so that short-circuiting may not be caused by contact between the shutter 2001 and the wiring pattern 2021. In particular, protrusions 2008 are left at end portions of the shutter 2001 as shown in FIG. 2B so that, when the shutter 2001 is excessively pivoted toward the glass substrate 2020 with a wiring pattern, only the protrusions 2008 may serve as portions which may possibly contact with the glass substrate 2020 with a wiring pattern. Then, in the regions on the glass substrate 2020 with a wiring pattern side with which the protrusions 2008 may possibly contact, wiring pattern recessed portions 2027 are formed as shown in FIG. 2D. By this, it is possible to avoid occurrence of short-circuiting also when the protrusions 2008 are brought into contact with the glass substrate 2020 with a wiring pattern. However, in this state, there is the possibility that leak light may appear through the incision portion 2006 at portions in the proximity of the protrusions 2008. Therefore, the metallic pattern (light blocking pattern) 2022 for blocking light is formed on a face of the glass substrate 2020 with a wiring pattern on the opposite side to the side on which the wiring patterns 2021 of the glass substrate 2020 with a wiring pattern are formed. From the foregoing, both of avoidance of short-circuiting by contact of the wiring lines on the shutter glass and blocking of leak light from the incision portion 2006 are achieved.

Now, a structure of the SOI region 2016 of the micro shutter 2010 is described with reference to FIG. 3A. The micro shutter 2010 includes micro shutters formed on the SOI region shown in FIG. 2B and arrayed in rows and columns.

Figure 3A:
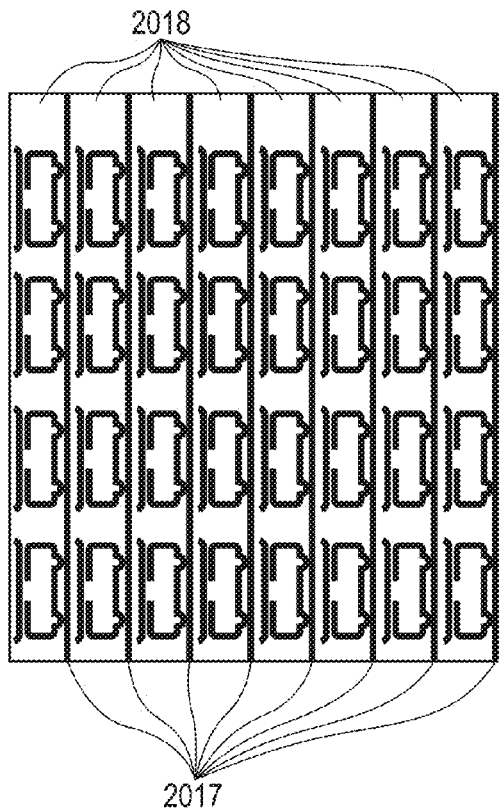
FIG. 3A is a plan view of the SOI region of the micro shutter array as viewed from above.

In the micro shutter array shown in FIG. 3A, the micro shutters in each of shutter columns 2018 extending along the column direction are placed in an electrically conducting state to each other while the micro shutters in each of shutter rows extending along the row direction are placed in a non-conducting state by grooves 2017 formed by engraving the SOI region 2016 until the BOX film 2014 can be seen therethrough. As hereinafter described, by devising the voltages to be applied to wiring lines for establishing conduction along the row direction, an arbitrary shutter in the array can be opened and closed.

Figure 3B:
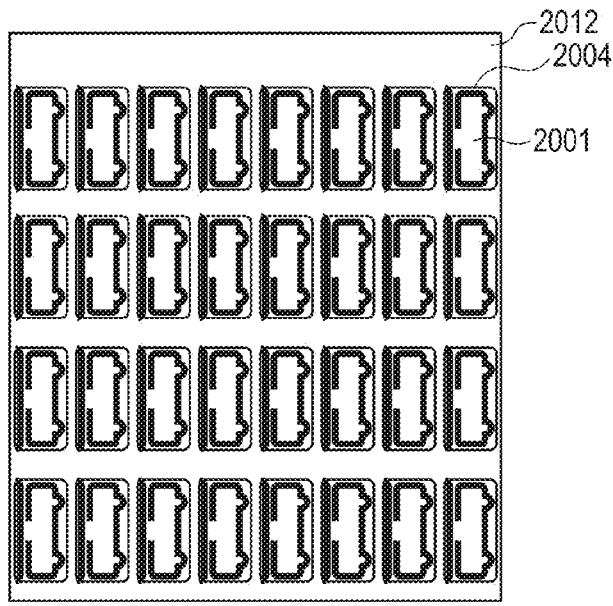
FIG. 3B is a plan view of the SOI region of the micro shutter array as viewed from below.

Now, the structure of the Si substrate 2012 side of the micro shutter 2010 is described with reference to FIG. 3B. The apertures 2004 formed in the Si substrate 2012 are juxtaposed in rows and columns at pitches at which the micro shutters are arrayed in rows and columns. The apertures 2004 are formed by carrying out deep RIE for the Si portion 2012 from the Si substrate 2012 side to form perforations and removing portions of the oxide insulating film BOX film 2014 on the bottom of the apertures 2004 of the Si substrate 2012 by such means as etching. Therefore, the shutters 2001 formed in the SOI region 2016 can be seen from the bottom face side of the SOI wafer 201.

Figure 4:
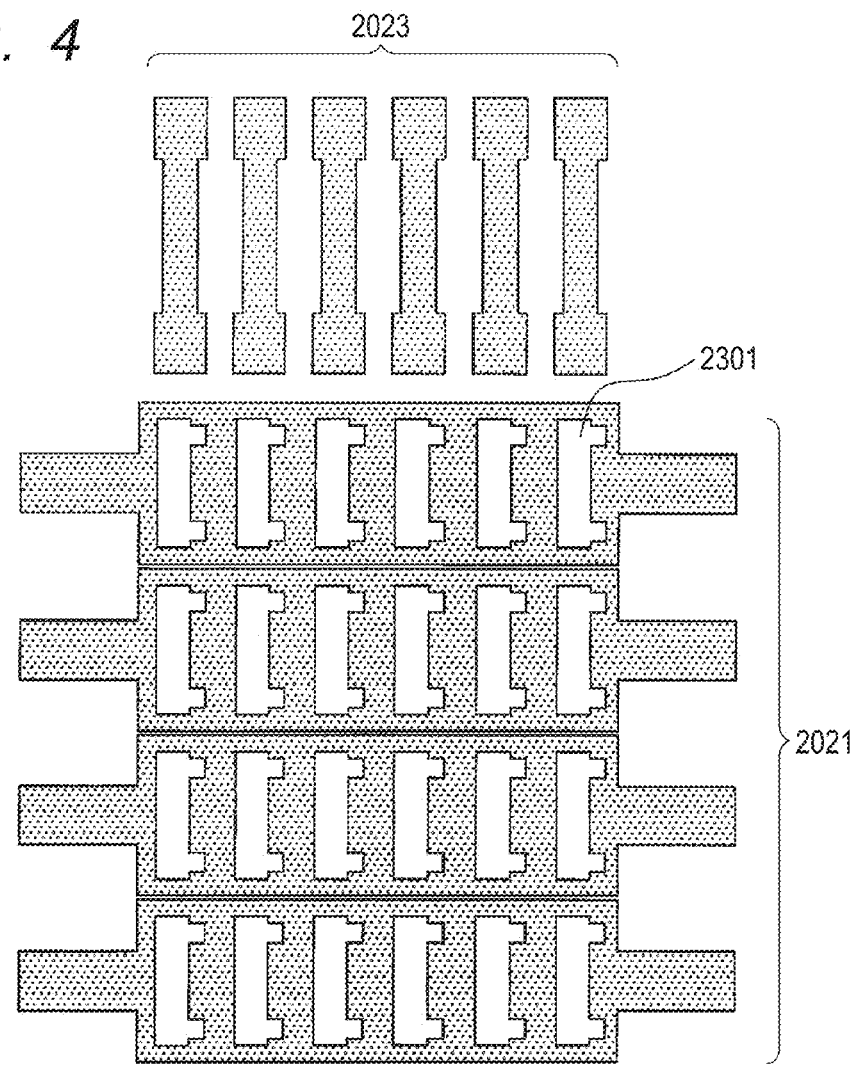
FIG. 4 is a plan view of glass with wiring patterns showing a wiring line shape fabricated on the lower face of the glass with wiring patterns of the micro shutter array.

Now, the wiring lines fabricated on the bottom face of the glass substrate 2020 with a wiring pattern are described with reference to FIG. 4.

On a face of the glass substrate 2020 with a wiring pattern on the side on which the micro shutter array 2100 is mounted, the wiring patterns 2021 and 2023 for supplying electric power of two systems for operating the shutters 2001 formed in the SOI region 2016 are formed. Meanwhile, the light blocking patterns 2022 which do not involve power distribution are formed on the face on the opposite side to the side on which the micro shutter array 2100 is mounted. FIG. 4 shows the face of the glass substrate 2020 with a wiring pattern on the side on which the micro shutter array 2100 is mounted while the light blocking patterns 2022 formed on the face on the opposite side are not shown.

The wiring patterns 2023 are used to supply a potential to the columns (in the upward and downward direction of FIG. 4) of the shutter array. The wiring patterns 2021 are utilized to place a shutter 2001 in a closed state into a latched closed state. The wiring patterns 2021 include apertures 2301 a little smaller than those of the shutters 2001 such that, when the shutters 2001 are in an open state, light passing through the shutters 2001 passes therethrough. The wiring patterns 2021 and 2023 and the light blocking patterns 2022 engraved to form the shutters 2001 are preferably provided with desired patterns by forming a chromium film by approximately 10 nm on a glass substrate, forming a film of gold or aluminum by 50 nm, preferably by more than 100 nm and then carrying out a photolithographic step to etch the gold or aluminum and the chromium in order. This is because, although gold or aluminum is a material convenient to obtain a desired light blocking pattern, by forming a thin chromium film intermediately, it is intended to enhance the close contactness with glass which is liable to be insufficient.

It is to be noted that, in the present embodiment, the glass substrate 2020 with a wiring pattern may be used as an optical device of the transmission type. In this instance, as a method for etching the wiring patterns 2021 and 2023 and the light blocking patterns 2022, it is important to apply wet etching. This is because, if pattern formation by dry etching is carried out, then a large number of very small damages appear on a glass substrate as a base material and such very small damages not only serve as a scattering source of light but also cause degradation of the light transmission factor which is critical to the optical device of the transmission type. Therefore, although titanium, titanium nitride or the like is sometimes used for the enhancement of the close contactness between films in a semiconductor or the like, those films which assume dry etching are not suitable for pattern formation on the glass substrate 2020 with a wiring pattern in the present embodiment.

Now, a sectional structure of the optical filtering device 2000 is described with reference to FIGS. 5A to 5C.

In the optical filtering device 2000, such unit shutters 2010 as described hereinabove with reference to FIG. 2A are arrayed in XY directions like a lattice. FIG. 5C is a plan view of the micro shutters 2010 formed on the SOI wafer 201. FIG. 5A is a view of the micro shutters 2010 of FIG. 5C mounted on the optical filtering device 2000 as viewed from a section taken along line A-A' of FIG. 5C, and FIG. 5B shows a view as viewed from a section taken along line B-B' of FIG. 5C.

In this configuration, the wiring patterns 2023 and the SOI regions 2016 are fixed to each other so as to be conducted with each other by conductive bonding agent 2028. The sizes of the conductive bonding agents 2028 and 2028' can be made uniform to some degree by using a semi-automatic die bonder or dispenser.

By fixing the wiring patterns 2023 and the SOI regions 2016 in such a positional relationship as in FIG. 5, the conductive bonding agents 2028 and 2028' play a role also of spacers for preventing the glass substrate 2020 with a wiring pattern and the shutters 2001 from contacting with and attracting each other. Although the distance between the glass substrate 2020 with a wiring pattern and the SOI region 2016 formed by the conductive bonding agents 2028 and 2028' is controlled to approximately 15 to 35 μm, more preferably the distance is controlled to 20 to 25 μm.

It is to be noted that, although the invention disclosed in JP-A-2000-352943 (Patent Document 7) is available as an invention similar to that of the present embodiment, it is described with reference to FIGS. 2A to 5C that the invention is different from that of the present embodiment.

In the invention disclosed in Patent Document 7, an electrode for latching a shutter is provided just above an aperture 2004 as shown in FIG. 3 of Patent Document 7. In the FIG. 3, also an annotation that ITO (Indium Tin Oxide) is used in a device of the backlight type and Al is used in a device of the reflection type is appended to the figure.

The invention which can be utilized as an optical device of the light transmission type similarly as in the present embodiment corresponds to a device of the backlight type from between the two types. It is estimated that the optical device functions as a device which uses ITO for the metal electrode and transmits visible rays therethrough.

On the other hand, in the present embodiment, no electrode exists just above the aperture 2004 as shown in FIG. 2A. This is because a metal which does not transmit light therethrough is used for the electrode so that the light blocking rate becomes high when the shutter is closed.

If a metal electrode which does not transmit light therethrough exists just above the aperture 2004, then the device does not function as an optical device of the light transmission type. In other words, the invention disclosed in Patent Document 7 and the invention of the present embodiment are different in three-dimensional structure of the device.

It is to be noted that, in the invention disclosed in Patent Document 7, ITO is used for the metal electrode. In a defect inspection apparatus for a semiconductor in which the optical filtering device 2000 of the invention of the present embodiment is used, in order to assure the defect detection sensitivity, usually illumination light of ultraviolet to deep ultraviolet wavelengths is used. Since an ITO film does not transmit light particularly of deep ultraviolet wavelengths therethrough, it is appended that the device of the invention disclosed in Patent Document 7 cannot be used alternatively.

It is to be noted that, at present, existence of a transparent metal film which exhibits a high transmittance of deep ultraviolet light and can be formed as a stabilized flattened film is not known. Even if the electrode material is changed in the device structure of the invention disclosed in Patent Document 7, it is difficult at present to implement a function same as that of the present invention.

Separately from the foregoing, the present embodiment has a difference from Patent Document 7. This is described in the following.

It is known that, if a thin film of silicon of a shutter main body or the like contacts in plane with glass or the like, then a sticking phenomenon occurs. Describing this in connection with the present embodiment, the sticking phenomenon is likely to occur in a latched closed state (state in which a shutter is attracted to a glass substrate with a wiring line pattern). Although several different shutters are shown in Patent Document 7, no protrusion is added to any of the shutters. Therefore, even if a tip end of a shutter is brought into contact with a spacer film on an address electrode, if the potential difference between the address electrode and the shutter is still great, then the suspension and the tip end of the shutter serve as a fulcrum while a portion of the shutter in the proximity of the center of gravity serves as a force point and a great warp occurs. Consequently, the portion of the shutter in the proximity of the tip end contacts over a wide area with the spacer film. The adhesive force by sticking increases in response to the contact area. If the adhesive force by sticking is high, then the shutter is place into a state in which it is not removed by electrostatic force, which disables opening and closing of the shutter main body. Or if the shutter is removed by force, then the possibility that the shutter main body may be damaged increases.

On the other hand, the shutter of the present embodiment has a protrusion additionally provided at a tip end thereof. Consequently, the region for contact is restricted to the region of the protrusion. Further, the protrusion portion is formed small to obtain a structure wherein, even if the protrusion region is brought into contact with a glass substrate, no significant warp occurs. In other words, the invention disclosed in Patent Document 7 and the invention of the present embodiment are different from each other in three-dimensional structure of the device.

Figure 5A:
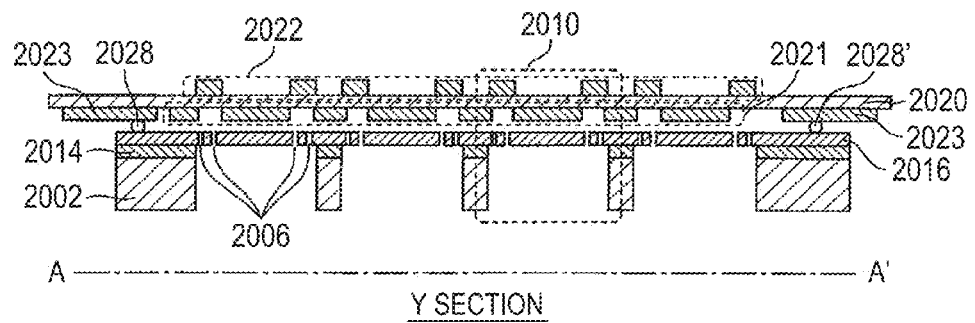
FIG. 5A is a sectional view taken along line A-A' of micro shutters incorporated in the optical filtering device.
Figure 5B:
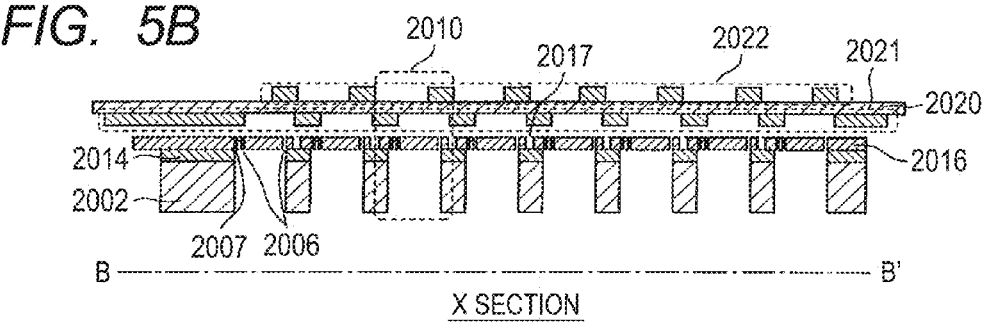
FIG. 5B is a sectional view taken along line B-B' of the micro shutters incorporated in the optical filtering device.
Figure 5C:
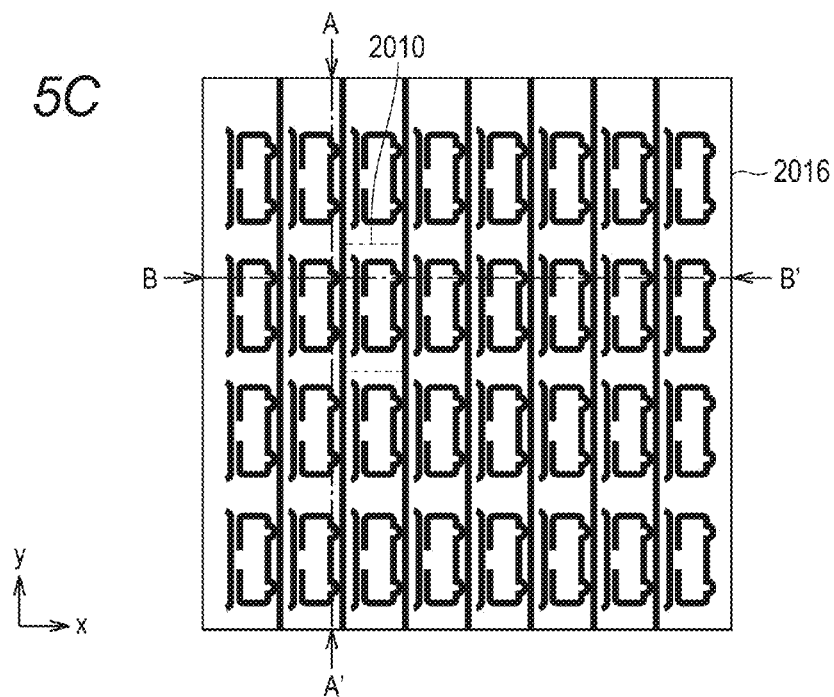
FIG. 5C is a plan view of the micro shutters formed on a wafer 201.

In the description of the embodiment relating to FIGS. 5A and 5B, it is described that the distance between the glass substrate 2020 with a wiring pattern and the SOI region 2016 is controlled to approximately 15 to 35 µm. However, a conductor portion (a wiring line, a shutter or the like) of a different potential is disposed at a very close place in this manner. Therefore, if a high voltage is applied to the conductor portion on the glass substrate 2020 with a wiring pattern or the micro shutter array 2100, even if they are sealed in dry air, there is the possibility that dielectric breakdown may occur to cause discharge, resulting in damage to the conductor portion. Generally, an approximate field strength of dielectric breakdown of dry air is approximately 3 kV/mm. In particular, the distance between the glass substrate 2020 with a wiring pattern and the SOI region 2016 preferably is approximately 20 to 25 µm. Therefore, if the potential difference between the wiring patterns 2021 and 2023 on the glass substrate 2020 with a wiring pattern and the shutter 2001 exceed 60 to 75 V, then there is the possibility that dielectric breakdown may occur. Accordingly, it is essentially required that the absolute value $|\Delta V2|$ of the potential difference between the wiring patterns 2021 and 2023 on the glass substrate 2020 with a wiring pattern and the shutter 2001 is less than 60 V in operation in which the safety is taken into consideration.

Within a range within which the inventors prototyped the device, the potential difference $V_{latch}$ for placing the shutter into a latched state was approximately 40 V. In this instance, it is possible to cause a shutter operation to be carried out without any problem even if the dielectric breakdown described hereinabove is taken into consideration.

It is to be noted that, in the shutter placed in the latched state, the distance thereof from the wiring patterns 2021 and 2023 on the glass substrate 2020 with a wiring pattern decreases. Although depending upon the design, the distance becomes approximately 10 µm at the narrowest place. Accordingly, to rapidly reduce the potential difference to be applied to the shutter placed in the latched state to $V_{itmed}$ hereinafter described with reference to FIG. 7B leads to avoidance of unnecessary dielectric breakdown.

Now, a principle of an action of the unit shutter 2001 is described with reference to FIG. 6A.

Figure 6A:
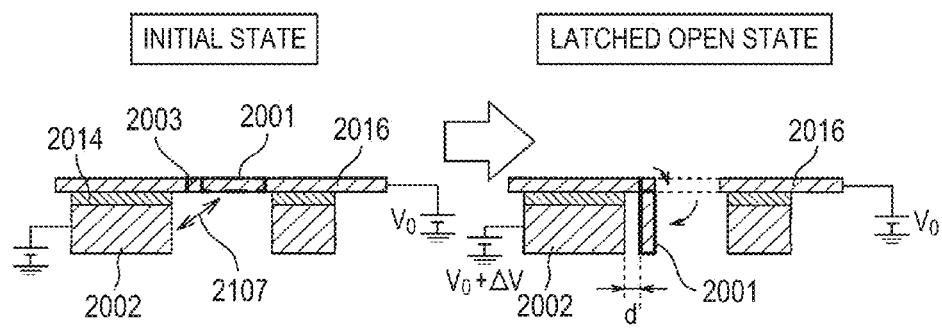
FIG. 6A is a sectional view of the unit micro shutter illustrating an initial state (closed state) and a latched open state of the micro shutter.

First, if, in a state (initial state) in which the shutter 2001 is closed as shown on the left side in FIG. 6A, a potential difference $\Delta V$ is applied between the shutter 2001 and the working electrode 2002 which are connected in an electrically isolated state by the BOX film 2014, then electrostatic attractive force 2107 acts between them. The electrostatic attractive force 2107 increases in proportion to the square of the absolute value $|\Delta V/d|$ of an electric field strength given by the quotient when the potential difference $\Delta V$ is divided by an average distance d (refer to FIG. 6C) between the working electrode 2002 and the shutter 2001. At this time, any of the potentials of the working electrode 2002 and the shutter 2001 is not necessarily equal to the ground potential, but the potential difference described above may be generated relatively. The suspension 2003 is twisted in response to the strength of the force, and the shutter 2001 is opened as shown on the right side in FIG. 6A. At this time, the distance d' between the shutter 2001 and the working electrode 2002 becomes smaller than that at the point of time at which the shutter movement, from the closed state (left side in FIG. 6A; initial state) to open state (right side in FIG. 6A), is started. Therefore, the absolute value $|\Delta V/d'|$ of the electric field strength is higher than the electrostatic attractive force 2107 which acts in a state in which the shutter 2001 is closed.

Since the average distance d between the shutter and the working electrode is reduced by a balance between force by which the suspension 2003 restores from the twist and the attractive force caused by the electric field, the electrostatic attractive force becomes stronger also in a state in which the same voltage is applied. Therefore, if the shutter 2001 is opened once, then even if the potential difference is changed to a lower potential difference $\Delta V'$, the open state of the shutter is maintained (latched open state).

The torsional restoring force of the suspension 2003 increases depending upon the angle of the twist. Here, as the potential difference $\Delta V$ decreases and approaches 0, the torsional restoring force of the suspension 2003 becomes dominant, and the shutter 2001 is closed as the suspension 2003 restores from the twist.

An opening and closing cycle of the shutter 2001 is such as described above.

It is to be noted that the magnitude of the electrostatic attractive force 2107 increases in proportion to the square of the absolute value $|\Delta V/d|$ of the electric field but has no relationship to whether the potential difference $\Delta V$ is in the positive or in the negative. Therefore, in the following, description is given of a case in which the potential difference $\Delta V$ is in the positive.

An operation cycle of the shutter 2001 is described with reference to FIG. 6B.

Figure 6B:
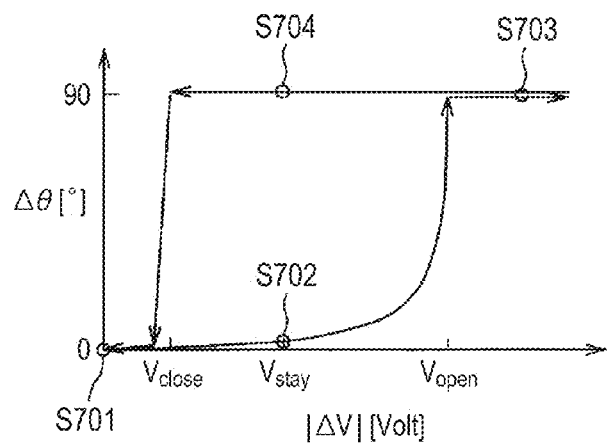
FIG. 6B is a graph illustrating a relationship between a potential difference $\Delta V$ between a shutter and a working electrode and a torsion angle $\Delta \theta$ of a suspension.
Figure 6C:
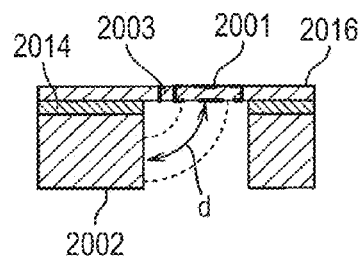
FIG. 6C is a sectional view of the unit micro shutter illustrating an average distance d between the working electrode and the shutter.

In a graph of FIG. 6B, the axis of abscissa indicates the potential difference $\Delta V$ between the shutter 2001 and the working electrode 2002, and the axis of ordinate indicates the torsional angle $\Delta \theta$ of the suspension 2003. If $\Delta \theta$ is almost 0, then the shutter 2001 indicates a closed state, but if $\Delta \theta$ is almost 90, then the shutter 2001 indicates an open state.

In the initial state (S701), the potential difference $\Delta V$ is $\Delta V=0$. Also in a state in which $\Delta V$ is raised from the initial state to $V_{stay}$ (S702), the shutter 2001 remains in a closed state (initial state). IF $\Delta V$ is raised further, then the shutter is opened fully at a point of time at which $\Delta V$ exceeds $V_{open}$ ($\theta \approx 90°$: latched open state). Even if $\Delta V$ is raised further, the state is maintained for a while (S703). Also in a state in which $\Delta V$ is lowered to $V_{stay}$ across $V_{open}$ (S704), the state in which the shutter is open fully (latched open state) is maintained. In other words, even if the potential difference $\Delta V$ is equal, the state in which the shutter is closed (S702) and the state in which the shutter is open (S704) can be implemented. If $\Delta V$ is further lowered and becomes lower than $V_{close}$, then the shutter 2001 is closed. $\Delta V$ is lowered finally to 0 to restore the initial state (S701).

As apparent from the foregoing description, the absolute value $|\Delta V|$ of the potential difference in the initial state (S701) may be any arbitrary potential difference if it is less than $V_{close}$. Meanwhile, $|\Delta V|$ in an intermediate state (S702, S704) may be an arbitrary potential difference which is not excessively proximate to $V_{close}$ and $V_{open}$, and $|\Delta V|$ in the fully open state (S703) may be a potential difference exceeding $V_{open}$.

Now, an action for compulsorily closing the shutter 2001 is described with reference to FIGS. 7A to 7C.

Figure 7A:
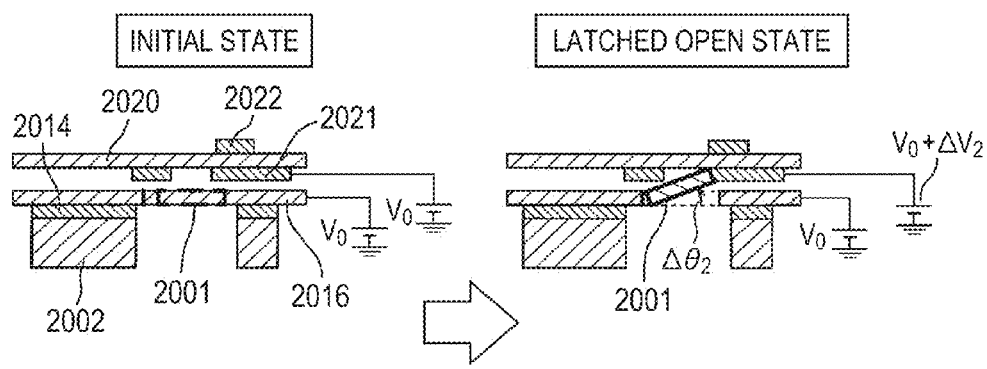
FIG. 7A is a sectional view of the unit micro shutter illustrating the initial state (closed state) and a latched closed state of the micro shutter.

First, if, in such a state (initial state) as illustrated on the left side in FIG. 7A, a potential difference $\Delta V2$ is applied between the shutter 2001 and the wiring pattern 2021 on the glass substrate 2020 with a wiring pattern, then electrostatic attractive force 2207 acts between them. Here, the electrostatic attractive force 2207 increases in proportion to the square of the absolute value $|\Delta V2/d2'|$ of an electric field strength obtained by dividing the potential difference $\Delta V2$ by the distance d2' (refer to the figure of the closed state on the left side in FIG. 7C). The suspension 2003 is twisted in response to the strength of the force, and the shutter 2001 is pivoted toward the glass substrate 2020 with a wiring pattern. The maximum angle $\Delta \theta_{max}$ of the pivotal motion is an angle at which the protrusions 2008 of the shutter 2001 almost contacts with the glass substrate 2020 with a wiring pattern. The state in which the shutter 2001 is pivoted to almost $\Delta \theta_{max}$ is hereinafter referred to as latched closed state.

Similarly as in the case in which the potential difference $\Delta V$ is applied between the shutter 2001 and the working electrode 2002, the distance d2' between the shutter 2001 and the wiring pattern 2021 (refer to a figure of the latched closed state on the right side in FIG. 7C) is smaller than the distance d2 between the shutter 2001 and the wiring pattern 2021 (refer to a figure of the initial state on the left side in FIG. 7C) at a point of time when the shutter movement, from closed state (initial state) to open state, is started. Therefore, the absolute value $|\Delta V2/d2'|$ of the electric field strength is higher than $|\Delta V2/d2|$. Further, if the shutter 2001 is placed into the latched closed state once, then even with a smaller potential difference $\Delta V2'$ ($\Delta V2 > \Delta V2'$), the latched state is maintained. If the potential difference $\Delta V2$ is further lowered to substantially 0, then the force for restoring the suspension 2003 from the twist becomes dominant, and the shutter 2001 returns to the initial state (left side in FIG. 7A).

Now, an operation cycle of the shutter 2001 is described with reference to FIG. 7B.

Figure 7B:
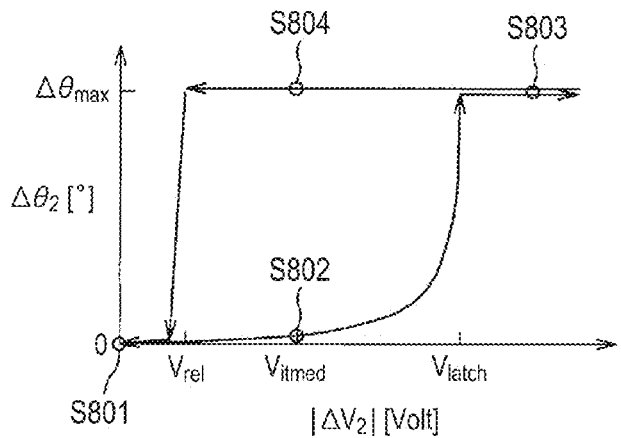
FIG. 7B is a graph illustrating a relationship between a potential difference $\Delta V_2$ from a wiring line produced on the lower face of the glass with wiring patterns and a torsion angle $\Delta \theta_2$ of the suspension.

The axis of abscissa of a graph of FIG. 7B is the potential difference $\Delta V2$ between the shutter 2001 and the wiring pattern 2021, and the axis of ordinate is the twist angle $\Delta \theta 2$ of the suspension 2003. However, the twisting direction is opposite to that in the case of FIG. 6A.

Figure 7C:
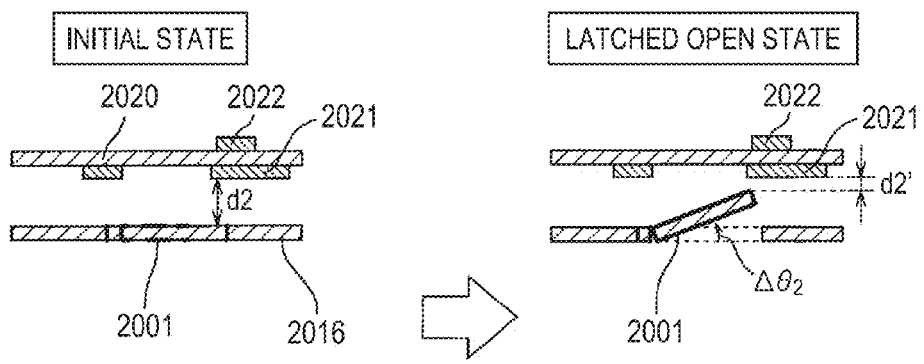
FIG. 7C is a sectional view of the unit micro shutter illustrating a distance between a wiring line fabricated on the lower face of the glass with wiring patterns and a macro shutter in the initial state (closed state) and the latched closed state of the shutter.

If $\Delta \theta 2$ is almost equal to 0, then this indicates that the shutter 2001 is in the closed state (state on the left side in FIG. 7C), but if $\Delta V2$ is almost equal to $\Delta \theta_{max}$, then this indicates that the shutter 2001 is in a compulsorily closed (latched closed) state (state on the right side in FIG. 7C).

In the initial state (S801), the potential difference $\Delta V$ is $\Delta V=0$. Also in a state in which $\Delta V2$ is raised from $\Delta V=0$ to $V_{itmed}$ (S802), the shutter 2001 remains in an almost closed state (state on the left side in FIG. 7C). If $\Delta V2$ is raised further, then the shutter enters a latched closed state (state on the right side in FIG. 7C) ($\Delta \theta \approx 90°$) at a point of time at which $\Delta V2$ exceeds $V_{latch}$. Even if $\Delta V2$ is raised further, the state is maintained for a while (S803). Also in a state in which $\Delta V2$ is lowered from the raised potential to $V_{itmed}$ across $V_{latch}$ (S804), the latched closed state of the shutter 2001 is maintained. In other words, even if the potential difference $\Delta V2$ is equal, it is possible to implement the closed state (S802) and the latched closed state (S804) of the shutter. If $\Delta V2$ is further lowered and becomes lower than $V_{rel}$, then the shutter 2001 is released into a closed state. $\Delta V2$ is lowered finally to zero to restore the initial state (S801).

As apparent from the foregoing description, the absolute value $|\Delta V|$ of the potential difference in the initial state (S801) may be any arbitrary potential difference only if it is less than $V_{rel}$, and $|\Delta V|$ in an intermediate state (S802, S804) may be an arbitrary potential difference which is not excessively proximate to $V_{rel}$ and $V_{latch}$. Further, $|\Delta V|$ in the fully open state (S803) may be a potential difference exceeding $V_{latch}$.

Now, a method of opening any other shutter than a desired shutter 2001 with the desired shutter 2001 held closed is described with reference to FIGS. 8A to 8F.

Figure 8A:
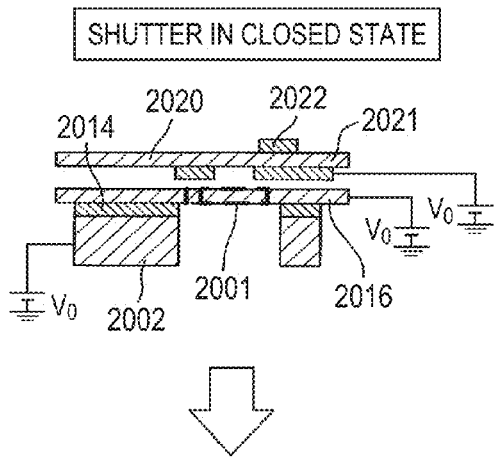
FIG. 8A is a sectional view of the unit micro shutter illustrating a relationship in potential among a wiring line fabricated on the lower face of the glass with wiring patterns, a micro shutter and a working electrode in the initial state (closed state) of the shutter.
Figure 8B:
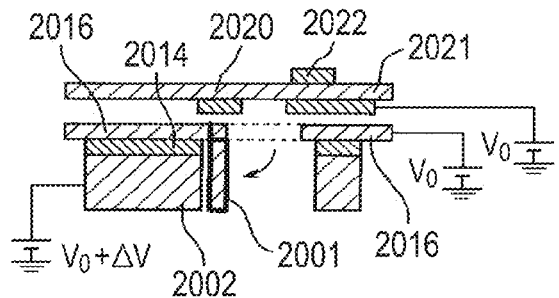
FIG. 8B is a sectional view of the unit micro shutter illustrating a relationship in potential among the wiring line fabricated on the lower face of the glass with wiring patterns, the micro shutter and the working electrode in the latched open state of the shutter.

First, if the noticed shutter 2001 is in a closed state (S802 of FIG. 8F) as shown in FIG. 8A, then the shutter can be opened as shown in FIG. 8B (latched open state: S703' of FIG. 8F) by applying the potential difference $\Delta V$ to the working electrode 2002 as described hereinabove with reference to FIGS. 6A and 6B. However, since the potential difference of $\Delta V=V_{itmed}$ is generated between the shutter 2001 and the wiring pattern (electrode) 2021 on the glass substrate 2020 with a wiring pattern, the shutter 2001 is acted upon not only by the force tending to open the shutter 2001 described hereinabove with reference to FIGS. 6A to 6C but also by the force tending to attract the shutter 2001 toward the glass substrate side described hereinabove with reference to FIGS. 7A to 7C. Therefore, as the potential difference $\Delta V$ for opening the shutter 2001, $V'_{open}$ more than $V_{open}$ is required as shown in FIG. 8F.

Figure 8C:
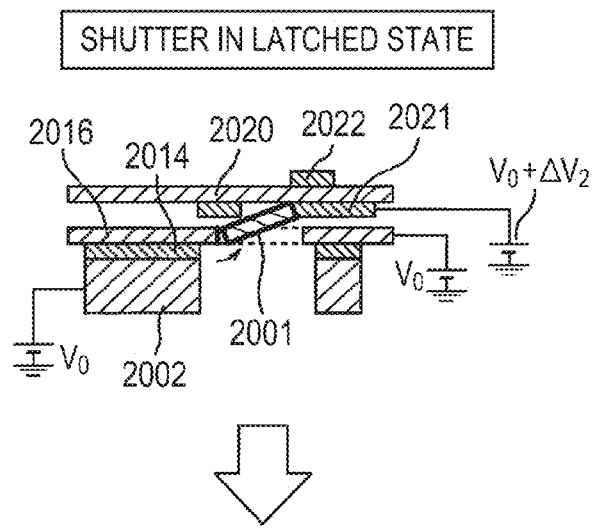
FIG. 8C is a sectional view of the unit micro shutter illustrating a relationship in potential among the wiring line fabricated on the lower face of the glass with wiring patterns, the micro shutter and the working electrode in the latched closed state of the shutter.
Figure 8D:
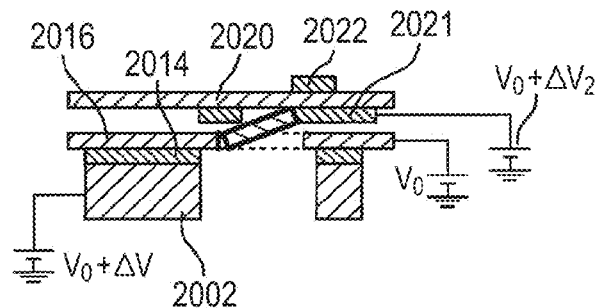
FIG. 8D is a sectional view of the unit micro shutter illustrating a relationship in potential among the wiring line fabricated on the lower face of the glass with wiring patterns, the micro shutter and the working electrode in the latched closed state of the shutter.
Figure 8E:
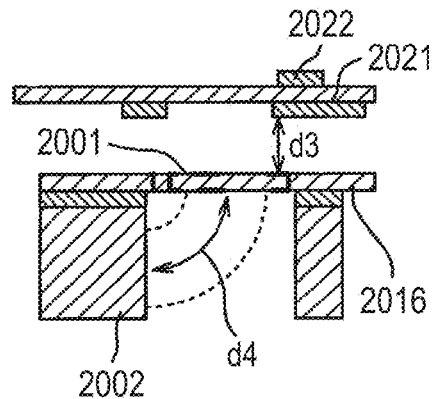
FIG. 8E is a sectional view of the unit micro shutter illustrating a distance between a micro shutter and a wiring line and a working electrode which are fabricated on the lower face of the glass with wiring pattern in the initial state (closed state) of the shutter.
Figure 8F:
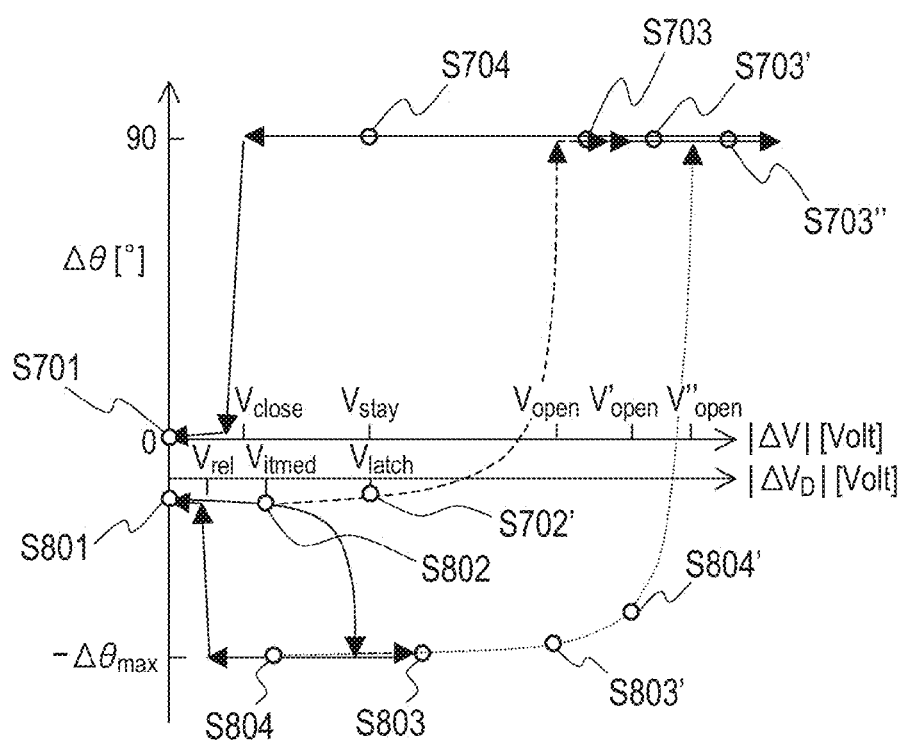
FIG. 8S is a graph illustrating a relationship between a potential difference $\Delta V$ between the shutter and the wiring line and working electrode fabricated on the lower face of the glass with wiring pattern and the torsion angle $\Delta \theta$ of the suspension.

On the other hand, if the noticed shutter 2001' is in the latched closed state (S803 or S804 of FIG. 8F) as shown in FIG. 8C, then even if the potential difference $\Delta V$ is applied to the working electrode 2002, the shutter 2001' can be left closed (S804' of FIG. 8F). This is because the distance d3 (refer to FIG. 8E) between the wiring pattern 2021 and the shutter 2001' is overwhelmingly short in comparison with the distance d4 between the shutter 2001' and the working electrode 2002. Consequently, although the force acting upon the shutter 2001' increases, in the direction toward the wiring pattern 2021, in proportion to the square of $|V2/d3|$ and, in the direction toward the working electrode 2002, in proportion to the square of $|\Delta V/d4|$, since d3<<d4, even if $\Delta V2 < \Delta V$, $|V2/d3| >> |\Delta V/d4|$. Therefore, the force by which the shutter 2001' is attracted by the working electrode 2002 does not act effectively.

It is to be noted that, when the potential difference $\Delta V$ is increased to $V''_{open}$ across $V'_{open}$, force higher than the force tending to attract the shutter 2001 to the side of the glass substrate 2020 with a wiring pattern described hereinabove with reference to FIGS. 7A to 7C acts between the working electrode 2002 and the shutter 2001. Consequently, the shutter 2001 is attracted to the side of the working electrode 2002 and opened (latched open). Therefore, the potential difference $\Delta V$ of the shutter 2001 should be set and operated within a range of $V'_{open} < \Delta V < V''_{open}$.

Here, the working electrode 2002 is placed in an equal potential state in all shutters on the micro shutter array 2100. Therefore, all of those shutters which are to be closed are placed in the latched closed state in advance, and after the potential difference $\Delta V$ is applied to the working electrode 2002 to open all of those shutters 2001 which are not in the latched closed state, the potential difference to be applied to the working electrode 2002 is lowered to such a degree that the shutters 2001 are not closed so that the opened shutters 2001 are maintained in the open state (in the latched open state). At this time, the shutter 2001' in the latched state may be returned to the closed state (initial state) by setting ΔV2 to ΔV2=0.

When the shutters in the overall micro shutter 2010 are to be closed, the potential difference to be applied to the shutters 2001, working electrodes 2002 and wiring pattern 2021 is set to 0.

Figure 9:
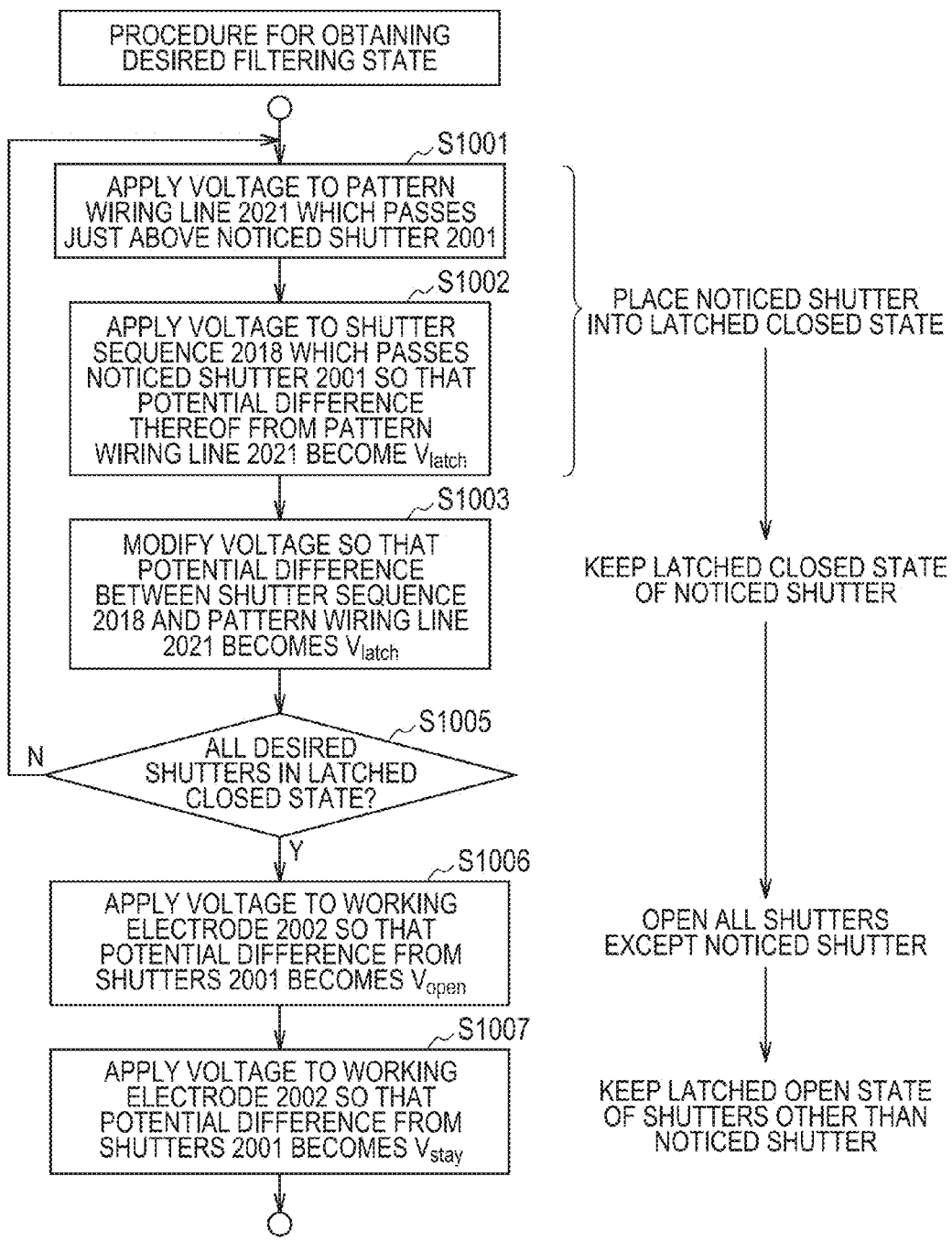
FIG. 9 is a flow chart illustrating a procedure for opening and closing a desired micro shutter.

A setting flow for obtaining a desired filtering state of the optical filtering device 2000 according to the present invention is illustrated in FIG. 9.

First, a voltage is applied to the wiring pattern 2021 which passes just above the noticed shutter 2001 (S901), and a voltage is applied to the shutter column 2018 which passes the aimed shutter 2001 so that the potential difference thereof from the wiring pattern 2021 may become equal to $V_{latch}$ (S902) thereby to place the noticed sutter 2001 into a latched closed state. Thereafter, the voltage is modified so that the potential difference between the shutter column 2018 and the wiring pattern 2021 may become equal to $V_{itmed}$ (S903) to maintain the latched closed state of the noticed shutter 2001.

The procedure at S901 to S903 described above is repeated until all desired shutters are placed into the latched closed state (S905).

After all desired shutters are placed into the latched closed state, a voltage is applied to the working electrode 2002 so that the potential difference thereof from each shutter 2001 may become equal to $V_{open}$ (S906) thereby to open all shutters other than the noticed shutter. Further, the voltage applied to the working electrode 2002 is adjusted so that the potential difference thereof from each shutter 2001 may become equal to $V_{stay}$ (S907) to maintain the state in which the shutters other than the noticed shutter are open (latched open state), thereby ending the setting for obtaining the desired filtering state.

Figure 10A:
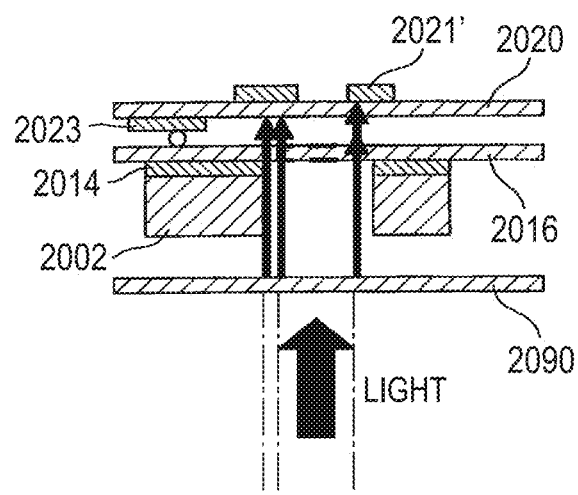
FIG. 10A is a sectional view of the unit micro shutter showing a wiring line of the glass substrate with wiring patterns which has a function of blocking leak light through an incision portion of the shutter.

Now, a modification to the glass substrate 2020 with a wiring pattern in the optical filtering device 2000 which uses the micro shutter array of the present invention is described with reference to FIGS. 10A and 10B.

The wiring lines of the glass substrate 2020 with a wiring pattern have a function of compulsorily placing the shutters 2001 into the closed state and another function of blocking leak light from the incision portions (2006 and 2007 in FIG. 2B). Accordingly, the wiring line regions may be provided at any position only if the wiring lines can compulsorily place the shutters 2001 into the closed state. In the present modification, a compulsorily closing wiring pattern 2021' is formed on a face of the glass substrate 2020 with a wiring pattern on the opposite side to the micro shutter array 2100 to integrate the wiring patterns 2021 and 2022 (light blocking patterns) in the configuration shown in FIG. 2A. In FIGS. 10A and 10B, like elements denoted by like reference characters to those in FIG. 2 indicate like configurations.

Figure 10B:
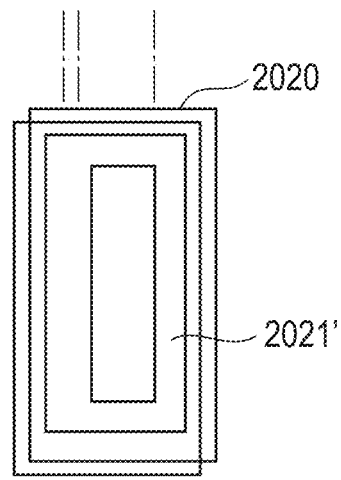
FIG. 10B is a plan view of the unit micro shutter showing the glass substrate with wiring patterns and the wiring patterns formed on the glass substrate.

In FIG. 10B, the glass substrate 2020 with a wiring pattern and the compulsorily closing wiring pattern 2021' formed on the glass substrate 2020 with a wiring pattern (micro shutter array 2100) are shown.

According to the present modification, since the compulsorily closing wiring pattern 2021' is formed on the face of the glass substrate 2020 with a wiring pattern on the opposite side to the micro shutter array 2100, a short-circuiting accident by contact of the shutter 2001 with the compulsorily closing wiring pattern 2021' can be prevented. Further, a region in which light is blocked by the compulsorily closing wiring pattern 2021' and the light blocking pattern 2022 shown in FIG. 2A may be formed on the glass substrate 2020 with a wiring pattern without dividing them from each other. Thus, such alignment of the wiring pattern 2021 formed on the lower side (micro shutter array 2100 side) of the glass substrate 2020 with a wiring pattern with the light blocking pattern (light blocking pattern) 2022 formed on the upper side of the glass substrate 2020 with a wiring pattern as illustrated in FIG. 2A is not required. Therefore, simplification and facilitation of the wiring line formation process are expected.

It is to be noted that, although it has been described that, according to the present embodiment, the shutter 2001 is formed by forming incisions on the SOI region of an SOI wafer, the light blocking property by the shutter 2001 may be improved by forming a metal film of aluminum, gold or the like in a reduced thickness on the SOI region.

Although a shutter opening and closing motion is described above using only a potential difference, in the following, an embodiment wherein a voltage is applied to the wiring patterns 2021 and 2023 on the glass substrate 2020 with a wiring pattern and the shutter 2001 is described particularly with reference to FIGS. 11A and 11B.

First, a base state 1 is a state in which all potentials are zero and is an initial state upon power on to the device of the present embodiment. In the base state 1, the shutter 2001 is in a closed state (state on the left side in FIG. 7A). Then, a stable state (S1101) is a state in which |5 V is applied to the wiring patterns 2021 and 2023 and the shutter 2001, and in the stable state (S1101), the absolute value $|\Delta V_2|$ of the potential difference is 0 V and the shutter is in a closed state. Then, a reference state 1 (S1102) is a state in which the voltage to be applied to the wiring patterns 2021 and 2023 is changed from −5 V to +5 V from the stable state (S1101). In the reference state 1 (S1102), the absolute value $|\Delta V_2|$ of the potential difference is 10 V and the shutter 2001 is in a closed state.

Then, an intermediate state 1 (S1103) is a state in which the voltage to be applied to the shutter 2001 is changed from −5 V to −20 V from the reference state 1 (S1102). In the intermediate state 1 (S1103), the absolute value $|\Delta V_2|$ of the potential difference is 25 V and the shutter 2001 is in a closed state.

Then, a transition level (S1104) is a state in which the voltage to be applied to the wiring patterns 2021 and 2023 is changed from +5 V to +20 V from the intermediate state 1 (S1103). In the transition level (S1104), the absolute value $|\Delta V_2|$ of the potential difference is 40 V and the shutter 2001 transits from the closed state to the latched closed state (state on the right side of FIG. 7A). Then, an intermediate state 2 (S1105) is a state in which the voltage to be applied to the wiring patterns 2021 and 2023 is changed from +20 V to +5 V from the transition level (S1104). In the intermediate state 2 (S1105), the absolute value $|\Delta V_2|$ of the potential difference is 25 V and the shutter 2001 is in the latched closed state.

Then, a reference state 2 (S1106) is a state in which the voltage to be applied to the shutter 2001 is changed from −20 V to −5 V from the intermediate state 1 (S1103). In the reference state 2 (S1106), the absolute value $|\Delta V_2|$ of the potential difference is 10 V and the shutter 2001 is in the latched closed state.

Further, the stable state (closed state: S1101) is restored by changing the voltage to be applied to the wiring patterns 2021 and 2023 from +5 V to −5 V from the reference state 2 (S1106).

The foregoing is the embodiment of the voltage value to be applied to the wiring patterns 2021 and 2023 on the glass substrate 2020 with a wiring pattern and the shutter 2001 in the shutter closing operation cycle in the shutter opening and closing operation cycle.

It is to be noted that, as can be recognized also from the description given hereinabove with reference to FIGS. 11A and 11B, if the voltage to be applied to the shutter 2001 is changed from −20 V to −5 V from the intermediate state 1

(S1103), then the absolute value $|\Delta V_2|$ of the potential difference is 10 V. Therefore, the shutter 2001 remains in the closed state and the reference state 1 (S1102) is restored. On the other hand, if the voltage to be applied to the shutter 2001 is changed from −5 V to −20 V from the reference state 2 (S1106), then the absolute value $|\Delta V_2|$ of the potential difference is 25 V. Therefore, the shutter 2001 remains in the latched closed state, and the intermediate state 2 (S1105) is restored. In other words, the reference state 1 (S1102) and the intermediate state 1 (S1103), and the intermediate state 2 (S1105) and the reference state 2 (S1106), are pairs of states which can be exchanged and between which the state can transit.

Figures 11A, 11B:
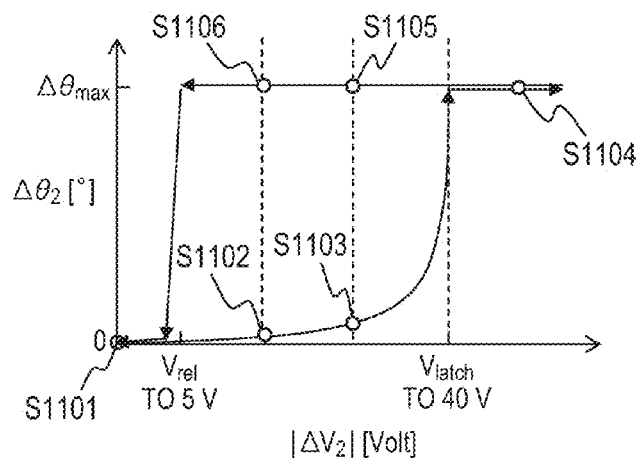
FIG. 11A is a graph illustrating a potential difference $\Delta V_2$ between a wiring line and a shutter on the glass substrate with wiring patterns and a torsion angle $\Delta \theta_2$ of the suspension.
FIG. 11B is a table illustrating a potential of a wiring line and a potential of a shutter on the glass substrate with wiring patterns and a relationship between the potential difference $\Delta V_2$ between the potentials and a state of the shutter.

As can be recognized from the description of FIGS. 11A and 11B, the shutter does not transit from the latched closed state to the closed state without passing the reference state 2 (S1106). It is possible to utilize this characteristic so that the shutters included in the overall region in which light is to be blocked transit from the closed state to the latched closed state.

Figure 12:
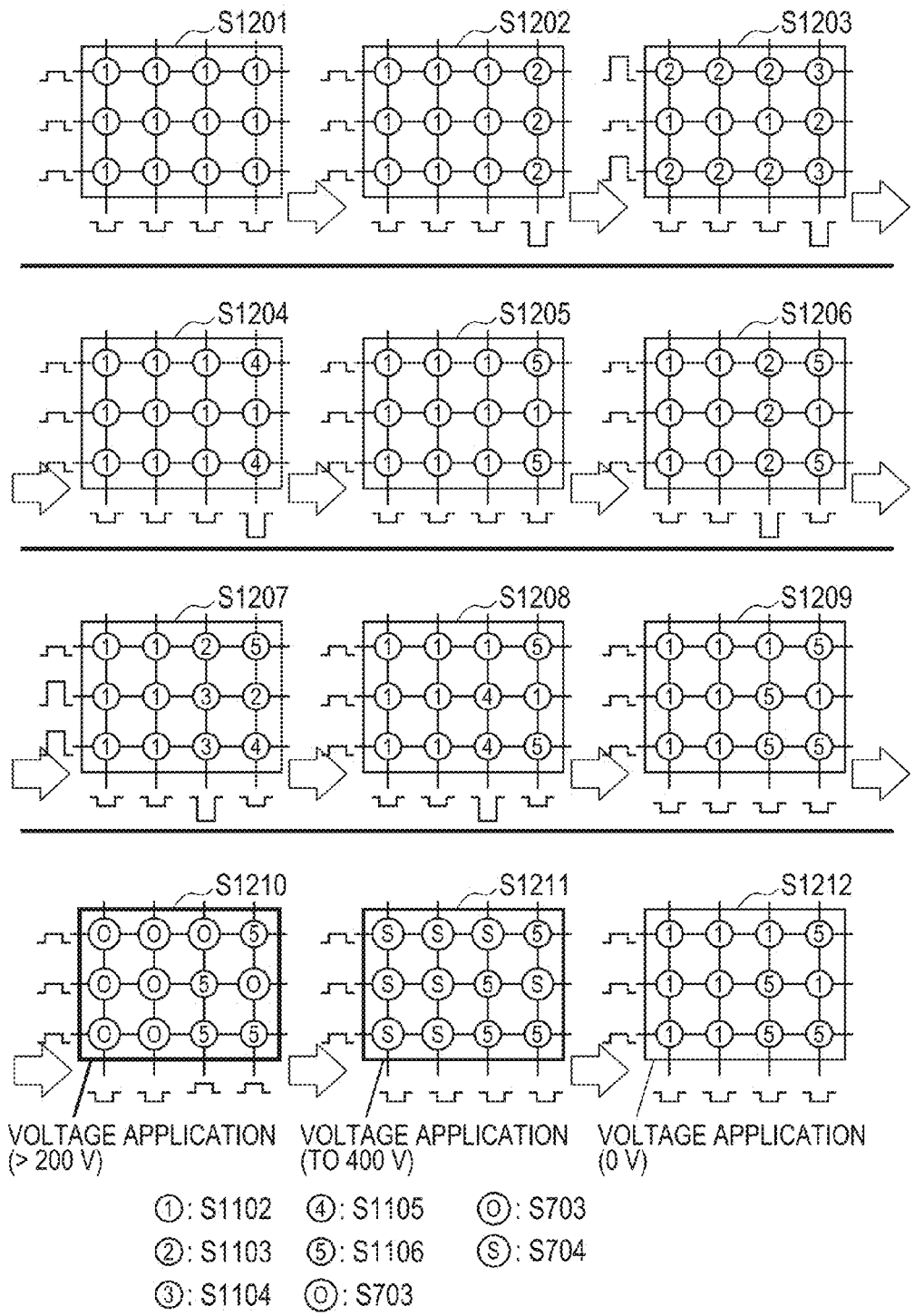
FIG. 12 is a view illustrating an example of a procedure for opening and closing a desired shutter in the micro shutter array.

FIG. 12 illustrates a procedure for causing the shutters 2001 included in the overall region in which light is to be blocked to transit from the closed state to the latched closed state. As shown in FIGS. 3A, 3B and 4, the shutters juxtaposed in the column direction are in a mutually electrically conducting state and are in a conducting state to the wiring patterns 2021 on the glass plate 2020 with a wiring pattern juxtaposed in the row direction. As can be recognized from the description of FIG. 11B, even if one of them is placed into a high voltage stage ($V_{A2}$, $V_{B2}$), the transition from the closed state to latched closed state does not occur. However, if both of them are simultaneously placed into a high voltage state with different polarities, then the transition from the closed state to latched closed state occurs. If the latched closed state is established once, then even if both of them are placed into a low voltage state ($V_{A1}$, $V_{B1}$), the latched closed state continues.

Therefore, in FIG. 12, the shutter columns in which the shutters are electrically connected are successively selected from the right and placed into a high voltage state ($V_{A2}$), and the rows of wiring line patterns on the glass substrate 2020 with a wiring pattern juxtaposed in the row direction formed at upper portions above the shutters included in the region in which light is to be blocked are selected and placed into a high voltage state ($V_{B2}$). As a result, the shutters 2001 included in the region in which light is to be blocked are placed into the latched closed state (state of 3: S1104 or 4: S1105 in FIG. 12). Such operation is successively repeated from S1201 to S1212 to cause all shutters 2001 included in the desired light blocking region to transit into the latched closed state.

After all shutters in the desired light blocking region are placed into the latched closed state, a high voltage (typically 200 V or more) is applied as a voltage corresponding to $V_{OPEN}$ illustrated in FIG. 6B to the working electrode 2002 so that all of the shutters in the closed state are placed into the latched open state (refer to FIG. 6A). Thereafter, even if the voltage to be applied to the working electrode 2002 is lowered to an intermediate voltage (typically approximately 40 V) as a voltage corresponding to $V_{STAY}$ illustrated in FIG. 6B, the shutters 2001 having been placed into the latched open state once maintains the latched open stage. By the foregoing, light blocking in a desired region using the optical filtering device 2000 of the present invention is implemented.

Further, if the voltage to be applied to the working electrode 2002 when the shutter 2001 is in the latched open state is set to −5 V as the voltage corresponding to $V_{CLOSE}$ illustrated in FIG. 6B, then the shutter 2001 and the working electrode 2002 come to have an equal potential. Consequently, no more electrostatic attractive force acts between the shutter 2001 and the working electrode 2002, and the shutter 2001 restores the initial closed state (left side in FIG. 6A) by the restoring force against the twist of the suspension 2003. During the sequence of closing, latch opening and closing operations of the shutter 2001, the voltage applied to the shutter 2001 is −5 V.

It is to be noted that S1102 to S1106 and S703, S704 illustrated in FIG. 12 are the initial state (closed state) and the latch closed state described hereinabove with reference to FIG. 11A and the latched open state described hereinabove with reference to FIG. 6, respectively.

Now, an embodiment of mounting of the controlling power supply system for controlling the light blocking state of the optical filtering device 2000 of the present invention is described with reference to FIGS. 13 and 14A to 14C.

Figure 13:
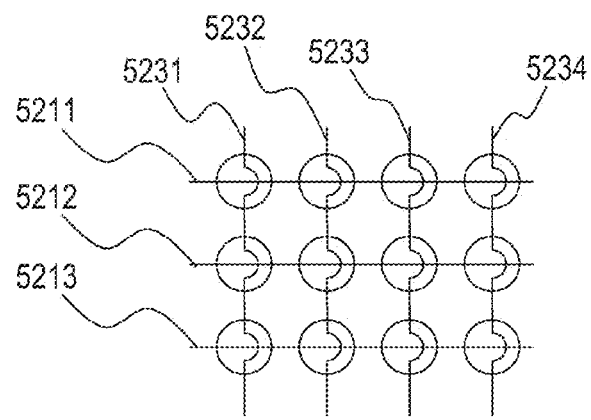
FIG. 13 is a diagram illustrating a subject in mounting of hardware for applying a desired voltage to micro shutter sequences and wiring line sequences on the lower face of the glass with wiring patterns.

As described hereinabove also with reference to FIG. 12, since the state of each shutter 2001 is controlled using control signals for the column and row directions, it is necessary to apply a number of mutually different signals equal to the number of signal lines for the column and row directions, basically equal to the number of all signal lines. In particular, in the case of a shutter array wherein 4×3 shutters indicated by round marks 1301 in FIG. 13 are arrayed, four signal lines 5231 to 5234 juxtaposed in the row direction and three signal lines 5211 to 5213 juxtaposed in the column direction, namely, totaling 4+3=7 signal lines, are provided. Meanwhile, in the case of another shutter array wherein 100×40 shutters are arrayed, 100+40=140 signal lines are provided as latch controlling signal lines. To those signal lines, it is necessary to apply signals which are basically different from each other. Therefore, for example, a dedicated IC which outputs 7 or 140 signals may be fabricated, or D/A outputs for 7 signals or 140 signals may be prepared.

Figure 14A:
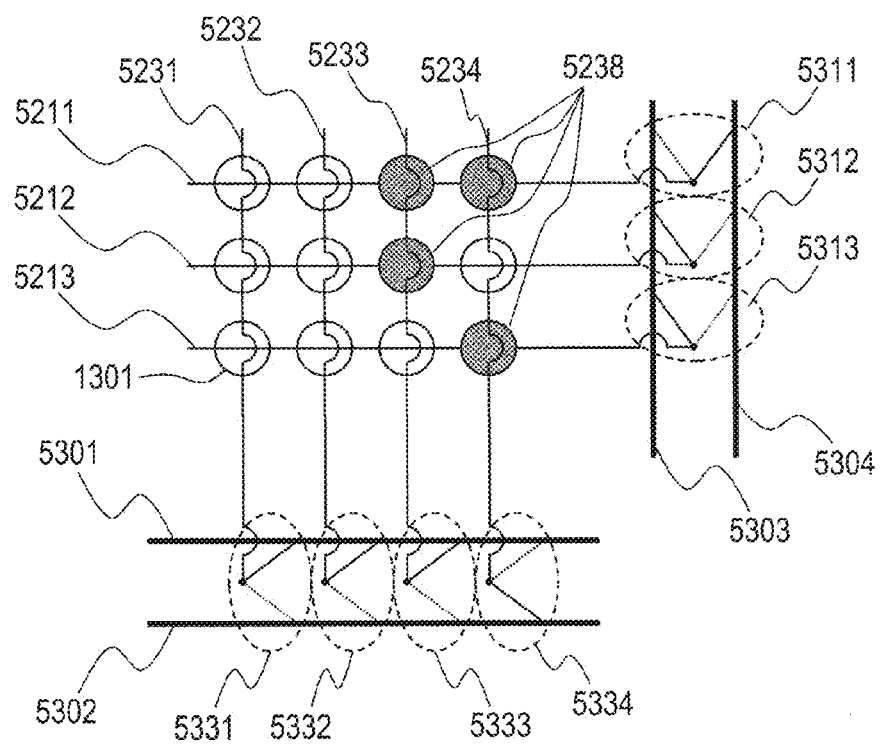
FIG. 14A is a circuit diagram illustrating a connection relationship between the micro shutter array and a driving power supply.
Figures 14B, 14C:
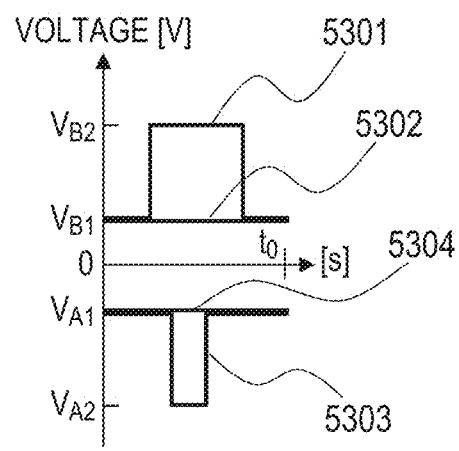
FIG. 14B is a graph illustrating a power supply voltage for driving the micro shutter array.
FIG. 14C is a table illustrating a state of a power supply switch for driving the micro shutter array at different points of time.

However, since similar signals are applied simultaneously to the individual wiring lines, a method of using switch sequences and signal outputs in combination can be incorporated more easily. Therefore, this is described with reference to FIGS. 14A to 14C. FIG. 14A illustrates a relationship between an array of shutters indicated by round marks 1301 and switch sequences 5311 to 5313 and 5331 to 5334. FIG. 14B is a graph illustrating a relationship between a state transition signal source output (5301 to 5303) and a voltage output (5302 and 5304) in a stable state. FIG. 14C is a table which illustrates states of connection between the switches 5311 to 5313 and 5331 to 5334 and the signal lines 5301 to 5304 within certain periods of time (period of time from 0 to $t_0$ and period of time from $t_0$ to $2 \times t_0$). An embodiment wherein the switch sequences (5331 to 5334 in the row direction and 5311 to 5313 in the column direction) and the state transition signal source outputs (5301 and 5303) as well as the voltage outputs (5302 and 5304) in the stable state are used as controlling power supplies for driving the shutter array.

Since the shutter array is a sequence of shutters which have opening and closing characteristics which are generally very similar to each other, it is possible to apply implementation wherein a single application voltage is used for each shutter column if the application voltage is selected suitably. The present embodiment is such a system as just described.

An operation sequence of the controlling power supply system for placing desired shutters 5238 into a latched state is described.

The shutter sequences 5231 to 5234 and the wiring line sequences 5211 to 5213 are electrically connected to switches 5331 to 5334 and 5311 to 5313, respectively. The switches 5311 to 5313 can change over the signal lines 5303 and 5304 and the switches 5331 to 5334 can change over the signal lines 5301 and 5302.

Such a periodical signal as illustrated in FIG. 14B flows along the signal lines 5301 to 5304 within a period $t_0$. The potentials $V_{A1}, V_{A2}, V_{B1}$ and $V_{B2}$ in FIG. 14B are selected so as to satisfy $V_{rel}<|V_{B1}-V_{A1}|<V_{latch}$, $V_{rel}<|V_{B2}-V_{A1}|<V_{latch}$, $V_{rel}<|V_{B1}-V_{A2}|<V_{latch}$ and $|V_{B2}-V_{A2}|>V_{latch}$ similarly to those described hereinabove with reference to FIGS. 11A and 11B. Here, it is essential that, after 5301 changes from $V_{B1}$ to $V_{B2}$, 5303 changes to $V_{A2}$ once and then returns to $V_{A1}$, whereafter 5301 changes from $V_{B2}$ to $V_{B1}$.

Now, a procedure for placing the desired shutters 5238 into a latched state is described with reference to the Table of FIG. 14C.

First, within a period from time 0 to time $t_0$, the switches 5311 to 5313 and 5331 to 5334 are changed over so as to be connected to signal lines indicated in the column 1401 at the center in the table. Similarly, within another period from time $t_0$ to time $2 \times t_0$, the switches 5311 to 5313 and 5331 to 5334 are changed over so as to be connected to signal lines indicated in the right side column of the table. Consequently, all desired shutters 5238 are placed into a latched state.

In the present control method, if a certain fixed voltage is applied, then state transition between the closed state and the latched closed state of the shutters does not occur with a signal line for a shutter column which does not directly participate in the latch closed state. In this instance, in the case of the present cycle, the signal line for the shutter column is 5212 within the time period from 0 to $t_0$ but is 5213, 5231 and 5232 within the time period from t0 to $2 \times t_0$. Further, the certain fixed voltage is a voltage which maintains, where the shutter column is latched already, the latched closed state, but maintains, where the shutter column is in the mere closed state, the closed state. Control of a switch sequence is used together so that a necessary control signal is applied only to a shutter sequence which directly relates to the latched closed state thereby to implement latch control of the shutters 1301. It is to be noted that, in order to cancel the latched closed state of all shutters, the switches 5311 to 5313 are connected to the signal line 5304 and the switches 5331 to 5334 are connected to the signal line 5302 and then the signal to be supplied to the signal line 5302 set to $V_{A1}$ to implement the cancellation of the latched closed state.

Figure 15A:
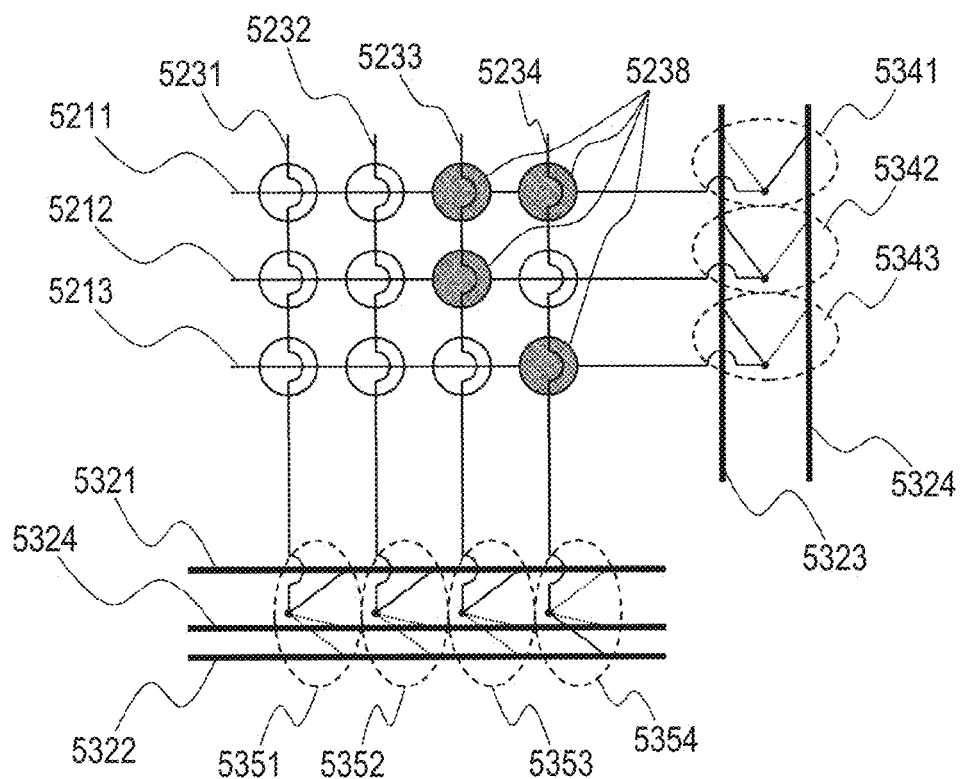
FIG. 15A is a circuit diagram illustrating a modification to the connection relationship between the micro shutter array and the driving power supply.

Now, an embodiment wherein switch sequences and voltage outputs in a stable state are used as control power supplies for driving the shutter array is described with reference to FIG. 15. The present embodiment is an embodiment which implements latch control of the shutters by utilizing only fixed power supplies and switch sequences.

An operation sequence of the control power supply system for placing a desired shutter 5238 into a latched state is described.

Figure 15B:
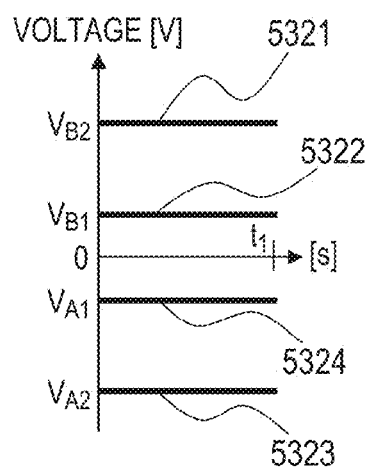
FIG. 15B is a graph illustrating a power supply voltage for driving the micro shutter array according to the modification.

The shutter sequences 5231 to 5234 and the wiring line sequences 5211 to 5213 are electrically connected to the switches 5351 to 5354 and 5341 to 5343, respectively. The switches 5341 to 5343 can change over the signal lines 5323 and 5324 and the switches 5351 to 5354 can change over the signal lines 5321, 5322 and 5324. To the signal lines 5321 to 5324, a fixed voltage is supplied as a signal in a period $t_0$ as illustrated in FIG. 15B. The potentials $V_{A1}, V_{A2}, V_{B1}$ and $V_{B2}$ in FIG. 15 are selected so as to satisfy $V_{rel}<|V_{B1}-V_{A1}|<V_{latch}$, $V_{rel}<|V_{B2}-V_{A1}|<V_{latch}$, $V_{rel}<|V_{B1}-V_{A2}|<V_{latch}$ and $|V_{B2}-V_{A2}|>V_{latch}$ similarly to those described hereinabove with reference to FIG. 14.

Now, a procedure for latching a desired shutter 5238 is described with reference to a table of FIG. 15C. The viewpoint of FIG. 15C is similar to that of FIG. 14C. Within periods from 0 to $t_1$, $t_0$ to $2 \times t_1$ and $2 \times t_1$ to $3 \times t_1$, the switches are changed over so as to be connected to the signal lines specified in the table. By this procedure, all desired shutters 5238 are placed into a latched state. By connecting the switches to the signal lines indicated in the column of $3 \times t_1 \sim$, the latched closed state can be maintained. It is to be noted that, by connecting the switches 5341 to 5343 and 5351 to 5354 to the signal line 5324, the latched closed state of all shutters is canceled.

Now, multi-functioning of the optical filtering device 2000 is described with reference to FIG. 16.

In the optical filtering device 2000 of the present invention, even if a shutter 2001 is attracted to the glass substrate 2020 with a wiring pattern or damaged, it is possible to apply a desired voltage unless the shutter 2001 is brought into contact with the working electrode 2002 or the wiring pattern 2021 to cause short-circuiting. In other words, mere supervision of the application voltage fails to manage the opening or closing state of the shutter 2001.

Therefore, a two-dimensional spatial filter system 32 which includes an optical filtering device 2000 and an expansion observation system 3210 for confirming an open or closed state of a shutter is configured (refer to FIG. 16A).

Figure 16C:
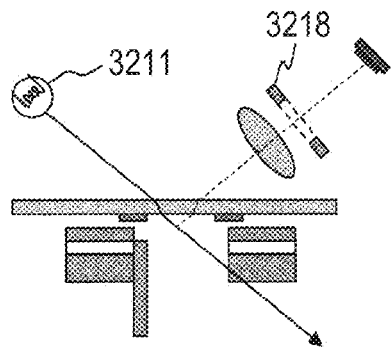
FIG. 16C is a sectional view of the unit micro shutter showing a configuration wherein the latched open state of the shutter is observed by the optical system.

The expansion observation system 3210 is configured at least from a lighting system 3211, a lens 3212, a camera 3213 and a diaphragm 3218. The camera 3213 is installed at a position conjugate with the shutter 2001 through the lens 3212. If reflected light 3214 from a noticed shutter 2001 arrives at the camera 3213 and the noticed shutter 2001 looks bright (FIG. 16B), then it is decided that the shutter 2001 is in a closed state. However, if no reflected light is received and the noticed shutter 2001 looks dark, then it is decided that the shutter 2001 is in an open state (FIG. 16C).

Figure 16D:
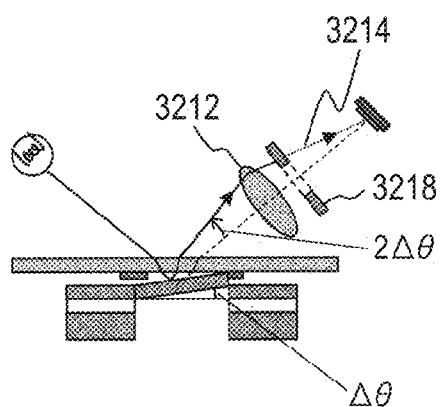
FIG. 16D is a sectional view of the unit micro shutter illustrating a state in which reflected light from a shutter is blocked by a diaphragm in the configuration wherein the latched closed state of the shutter is observed by the optical system.

Here, since the shutter 2001 which is in the latched closed state is inclined by $\Delta\theta$ with respect to a maximum angle $\Delta\theta_{max}$ as shown in FIG. 16D, directly reflected light is reflected in a direction displaced by $2 \times \Delta\theta$ from that from any other portion than the shutter. In the optical filtering device 2000, it is significant to actually measure an operating characteristic of the shutter 2001, and it is necessary to decide whether the shutter 2001 is in the closed state or in the latched closed state. Therefore, the aperture size of the diaphragm 3218 is changed to cause the camera 3213 to pick up an image to carry out state decision.

Figure 16E:
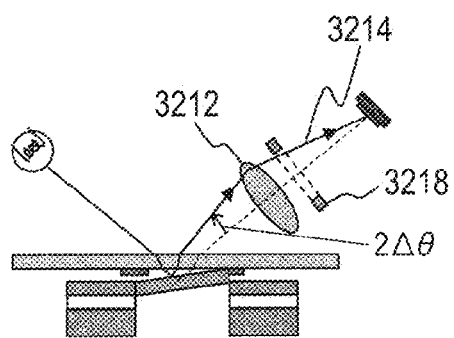
FIG. 16E is a sectional view of the unit micro shutter illustrating a state in which reflected light from the shutter passes through an aperture of the diaphragm and is detected by a camera in the configuration wherein the latched closed state of the shutter is observed by the optical system.

If the opening of the diaphragm 3218 is so small that reflected light from the shutter 2001 in the latched closed state does not enter the lens 3212, then the shutter 2001 looks completely dark (FIG. 16D). On the other hand, if the aperture 3219 of the diaphragm 3218 is made greater so that reflected light from the shutter 2001 in the latched closed state may arrive at the camera 3213, then the shutter 2001 looks bright (FIG. 16E). Therefore, the aperture 3219 of the diaphragm 3218 is made greater first, and an image by light reflected by the surface of the shutter 2001, condensed by the lens 3212 and transmitted through the aperture 3219 is picked up by the camera 3213. Then, the open or closed state of the shutter 2001 is decided from the bright or dark state of the position of the shutter 2001. Then, the aperture 3219 of the diaphragm 3218 is made smaller, and an image by light reflected by the surface of the shutter 2001, condensed by the lens 3212 and transmitted through the aperture 3219 is picked up by the camera 3213. Then, it is decided from the bright or dark state of the position of the shutter 2001 whether the shutter 2001 is in the closed state or in the latched closed state. It is to be noted that, where the open or closed state of the shutter 2001 is not confirmed, preferably the lighting system 3211 is extinguished or blocked so that illumination light may not be irradiated upon the optical filtering device 2000.

Figure 17A:
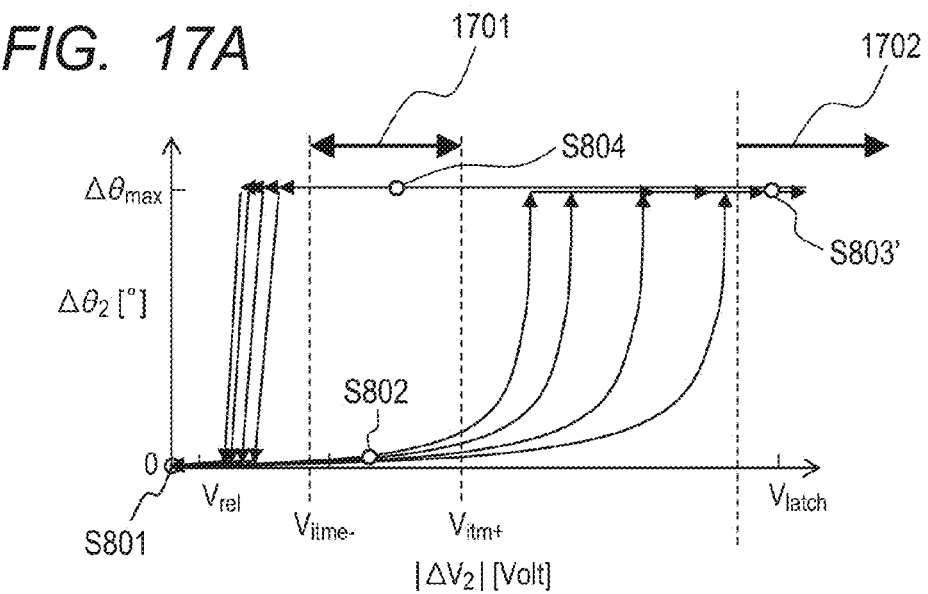
FIG. 17A is a graph illustrating a relationship between the potential difference $\Delta V_2$ and the torsion angle $\Delta \theta 2$ of the suspension of each of the shutters belonging to the optical filtering device and illustrating a cause of difference in opening/closing operation characteristic with respect to a potential difference between each shutter and a wiring line formed on the glass substrate with wiring patterns.
Figure 17B:
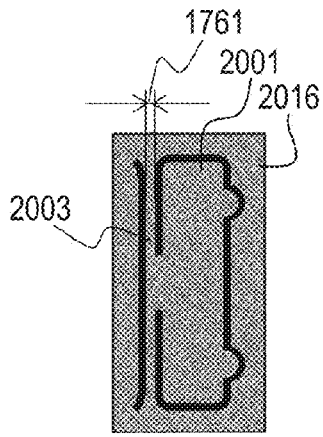
FIG. 17B is a plan view of a shutter formed on the SOI region.
Figure 17C:
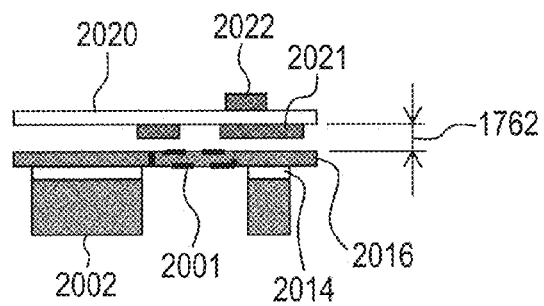
FIG. 17C is a sectional view of the unit micro shutter illustrating a distance between the glass substrate with wiring patterns and the SOI region.

A cause by which a dispersion occurs with the potential difference $\Delta V_2$ necessary for transition between the closed state and latched closed state of the shutter 2001 is described with reference to FIGS. 17A to 17C. Such a width 1761 of the suspension 2003 of the shutter 2001 as shown in FIG. 17B disperses among the shutters due to occurrence of a dispersion in the photolithographic step or the etching step of the MEMS. The range of the dispersion generally is approximately 10% with respect to the entire width 1761.

While, in the shutter array relating to the optical filtering device 2000 of the present embodiment, force of restoring the suspension 2003 from twist is utilized to restore the closed state of the shutter 2001, this restoring force against twist increases in inverse proportion to the sectional area of the suspension 2003. If the width 1761 of the suspension 2003 disperses to vary the sectional area of the suspension 2003, then also the restoring force of the suspension 2003 against twist varies, resulting in occurrence of a dispersion in the operation characteristic of the suspension 2003.

On the other hand, in each of the shutters 2001, transition between the closed state and the latched closed state occurs by generation of force which increases in proportion to the electrostatic force based on the potential difference appearing between the shutter 2001 and the wiring pattern 2021 formed on the glass substrate 2020 with a wiring pattern. Here, the electrostatic force generated between the shutter 2001 and the wiring line formed on the glass substrate 2020 with a wiring pattern increases in proportion to the square of the distance of a gap between the shutter 2001 and the glass substrate 2020 with a wiring pattern. Therefore, the potential difference upon transition from the closed state to the latched closed state disperses depending upon the dispersion of the gap distance between the shutter 2001 and the glass substrate 2020 with a wiring pattern.

The foregoing is a cause by which a dispersion for each shutter occurs with the operation potential difference in relation to the opening and closing state of each shutter 2001.

Figure 18:
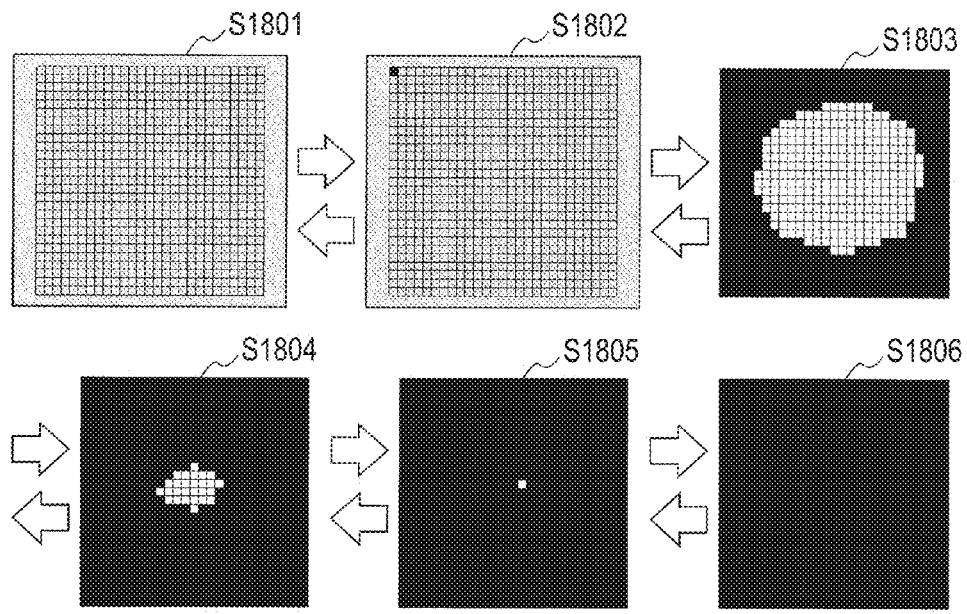
FIG. 18 is plan views of the optical filtering device illustrating a state in which the shutters of the optical filtering device are successively closed.

Although a dispersion of the operation characteristic of each shutter is fundamental, since shutters having opening and closing characteristics very similar to each other are originally juxtaposed over the overall shutter array, if the application voltage is selected suitably, then there is no necessity to change the application voltage for each shutter column. Therefore, an embodiment of a GUI for confirming a voltage characteristic in opening and closing of shutters included in the optical filtering device 2000 to set an application voltage is described with reference to FIGS. 18 and 19A to 19B.

If the potential difference between the shutter 2001 and the working electrode 2002 is gradually increased, then no state variation occurs for a while (S1801 in FIG. 18), and then only one shutter 2001 is opened first (S1802). Then, the number of shutters 2001 which are opened increases gradually, and finally, all of the shutters 2001 which are enabled for opening and closing operation are opened (S1803). If the potential difference is decreased from this state, then no state variation appears for a while similarly, and then only one shutter is closed first at a certain potential difference (S1804). Then, the number of shutters which are closed increases gradually (S1805), and finally, all shutters are closed (S1806). Here, necessary for the operation of the entire shutters are two potential differences including (1) the potential difference $V'_{stay}$ with which all of the open shutters are open stably and (2) the potential difference $V'_{open}$ with which all shutters are opened as described hereinabove also with reference to FIGS. 8A to 8E. In order to determine them, (A) the potential difference $V_{open}$ with which the shutters begin to open, (B) the potential difference $V'_{open}$ with which all shutters are opened and (C) the potential difference $V'_{close}$ with which the shutters begin to close are actually measured. (1) is determined from (A) and (C), and (2) is the value of (B).

Figure 19A:
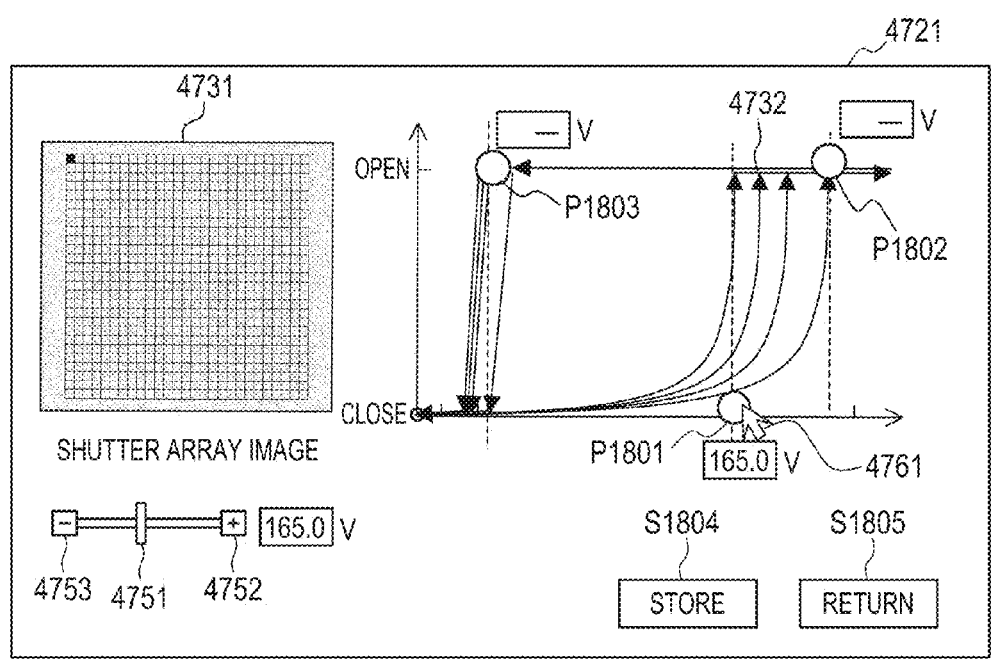
FIG. 19A is a front view of a user interface for setting a voltage for controlling a shutter array of the optical filtering device on a screen image in which an image of the shutter array observed by a camera of an expansion optical system and a relationship between the potential difference between a driving electrode and a shutter and the rotational angle of the shutter and illustrating a state in which one micro shutter cannot keep the latched open state any more.

FIG. 19A shows an example of a user interface 4721. On the user interface 4721, an image 4731 of the shutter array and a graph 4732 indicative of a relationship between the potential difference between the working electrode 2002 and the shutter 2001 and a pivotal angle of the shutter 2001 are displayed. On the user interface 4721, also a potential difference setting button 4751 for setting a potential difference between the working electrode 2002 and the shutter 2001, a storage button P1804 for storing a result of the setting, and a button P1805 for clearing the displayed contents to restore the initial state are displayed. By dragging the potential difference setting button 4751 of the user interface 4721 rightwardly or depressing a + button 4752, the difference between voltages to be applied to the shutter 2001 and the working electrode 2002, namely, the potential difference between the shutter 2001 and the working electrode 2002, is increased. On the interface, the image 4731 of the shutter array outputted from the camera 3213 of the expansion observation system 3210 for confirming the open or closed state of the shutters is displayed.

If the potential difference between the shutter 2001 and the working electrode 2002 comes to a certain level, then one of the shutters 2001 is opened and the shutter portion looks dark. Here, by clicking a button of P1801 on the graph 4732, (A) the potential difference $V_{open}$ with which a shutter begins to open is recorded.

Figure 19B:
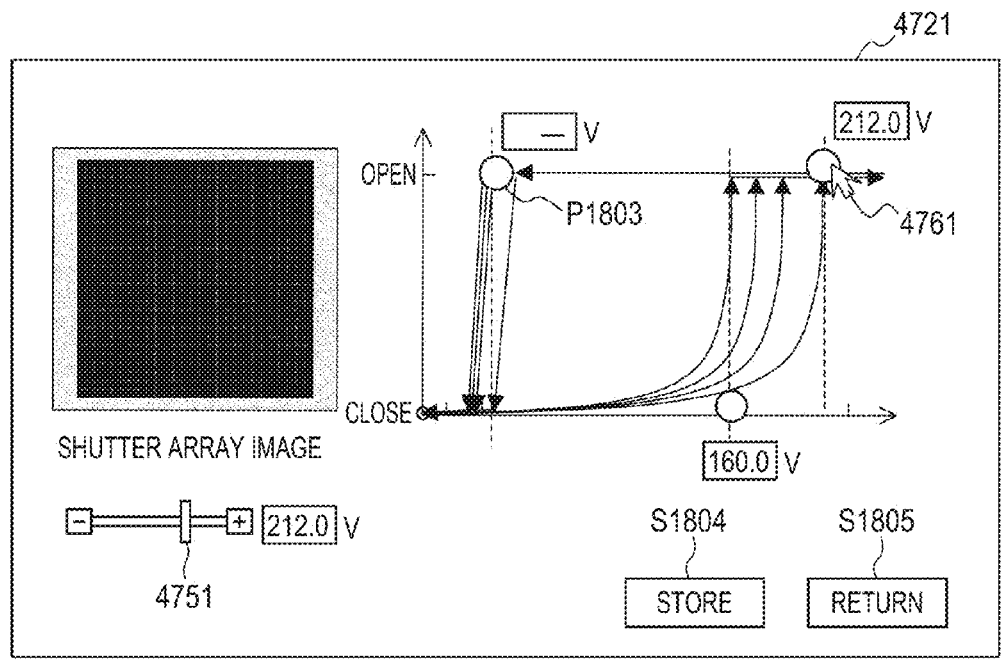
FIG. 19B is a front view of a user interface for setting a voltage for controlling a shutter array of the optical filtering device on a screen image in which an image of the shutter array observed by a camera of an expansion optical system and a relationship between the potential difference between a driving electrode and a shutter and the rotational angle of the shutter and illustrating a state in which all micro shutters are in the latched open state.
Figure 19C:
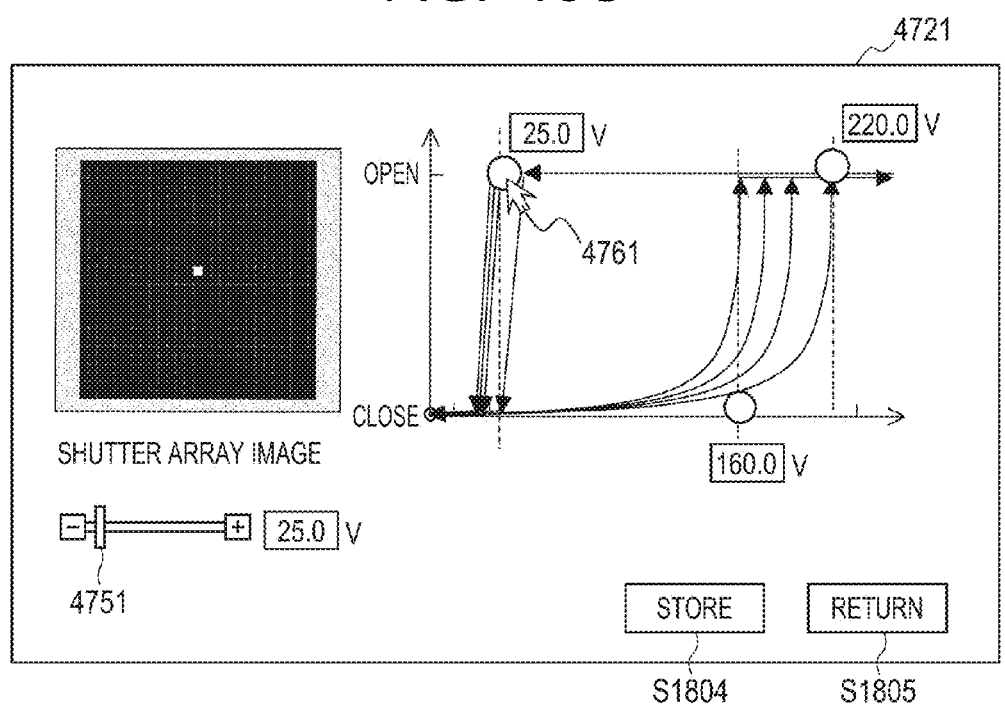
FIG. 19C is a front view of a user interface for setting a voltage for controlling a shutter array of the optical filtering device on a screen image in which an image of the shutter array observed by a camera of an expansion optical system and a relationship between the potential difference between a driving electrode and a shutter and the rotational angle of the shutter and illustrating a state in which the potential difference is set to 25 V and all micro shutters are in the latched open state.

At a point of time at which the potential difference setting button 4751 or the + button 4752 is operated further to increase the potential difference until all shutters are opened and the shutter portions come to look dark, a button of P1802 is clicked on the graph 4732 to record (B) the potential difference $V'_{open}$ with which all shutters are opened (FIG. 19B). If the potential difference setting button 4751 is dragged leftwardly or a − button 4753 is depressed from the point of time to gradually decrease the application potential difference between the shutter 2001 and the working electrode 2002, then the state in which all shutters are open exhibits no variation for a while similarly. Then, if the potential difference decreases to a certain potential difference, then one shutter closes first. Therefore, at this point of time, a button of P1803 is clicked on the graph 4732 to record (C) the potential difference $V'_{close}$ with which the shutters begin to close (FIG. 19C). $V'_{stay}$ of (1) described hereinabove is selected from within the range from $V'_{close}$ of (C) to $V_{open}$ of (A), and as $V'_{open}$ of (2), the value of (B) is selected as it is.

By the procedure described above, the voltages with which the shutters operate and which are applied to the shutter column are selected.

Now, an embodiment in which an optical filtering device which uses the micro shutter array according to the present invention is applied to an inspection apparatus is described with reference to FIG. 21A.

Embodiment 1

Figure 21A:
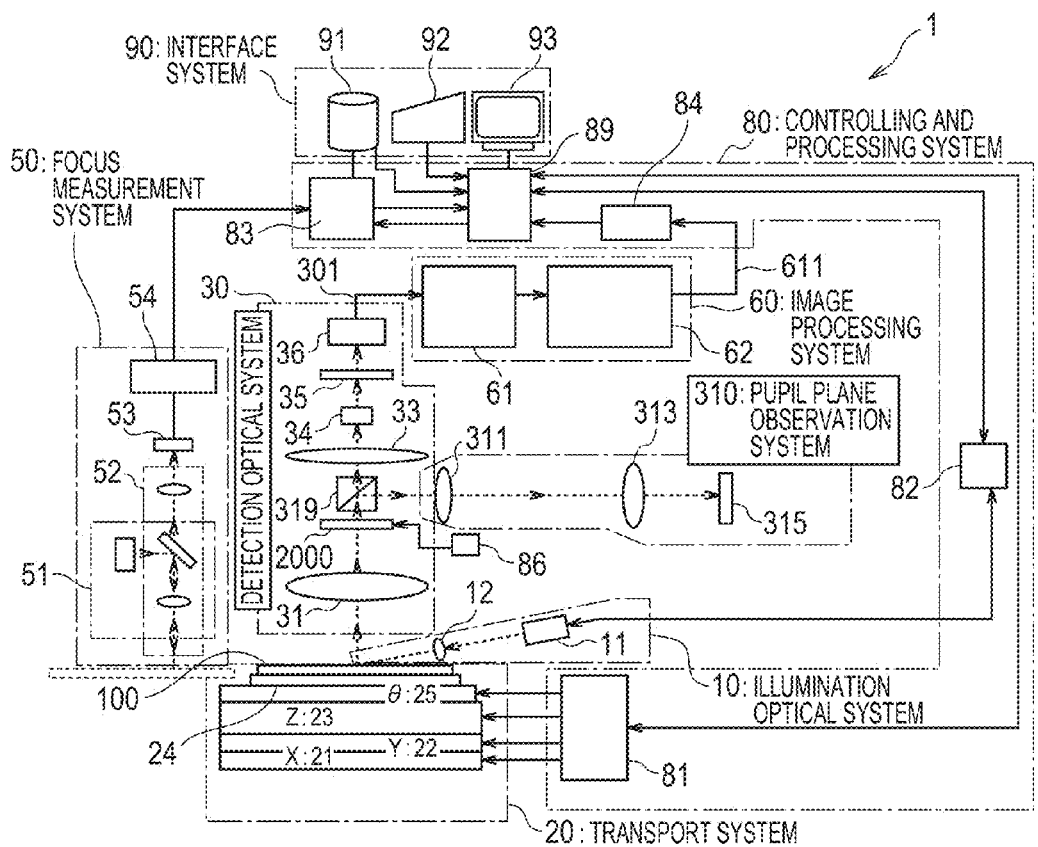
FIG. 21A is a block diagram showing a general configuration of an inspection apparatus which includes an optical filtering device in which a micro shutter array in a first embodiment and inspects a wafer having a pattern formed therein in a dark field.

A block diagram of an inspection apparatus 1 to which an optical filtering device which uses a micro shutter array according to an embodiment 1 is applied is shown in FIG. 21A.

The inspection apparatus 1 includes an illumination optical system 10, a substrate transport system 20, a detection optical system 30, a focus measurement system 50, an image processing system 60, a controlling and processing system 80, an interface system 90, and a pupil plane observation system 310.

The illumination optical system 10 includes a laser light source 11 and a lens 12 for beam shaping. Light emitted from the laser light source 11 is suitably shaped by the lens 12 and illuminates an inspection object substrate 100. In the present embodiment, the illumination optical system 10 illuminates a linear region on the inspection object substrate (semiconductor wafer: substrate) 100 which is elongated in one direction.

The substrate transport system 20 includes an X stage 21, a Y stage 22, a Z stage 23, a substrate chuck 24, and a θ stage 25. Further, a point light source 109 is placed in a neighboring relationship with the substrate chuck 24 at a height substantially equal to that of the wafer surface.

The detection optical system 30 includes an objective lens 31, an optical filtering device 2000, an imaging lens 33, an optical sensor 35, and an A/D conversion unit 36. By using a sensor of the integration type (TDI (Time Delay Integration) sensor) as the optical sensor 35, an inspection can be carried out at a higher speed. A polarizing filter 34 may be interposed between the imaging lens 33 and the optical sensor 35. In FIG. 21A, a diagram of a configuration which includes the polarizing filter 34 is shown.

The pupil plane observation system 310 includes a half mirror 319, lenses 311 and 313 and an area sensor 315 so that a light intensity distribution on the Fourier transform plane of the objective lens can be observed. The half mirror 319 transmits therethrough part of light condensed by the objective lens 31 and transmitted through the optical filtering device 2000 from within scattered light from the substrate 100 illuminated by the illumination optical system 10 and introduces the part of the light toward the imaging lens 33. Further, the pupil plane observation system 310 reflects the remaining light so as to be introduced toward the pupil plane observation system 310.

The focus measurement system 50 includes an illumination optical system 51, a detection optical system 52, an optical sensor 53, and a focus shift calculation processing unit 54.

The image processing system 60 includes an inter-adjacent die image positional displacement information calculation unit 61, and a data processing unit 62 which uses an inter-die difference image to carry out a defect decision and detection process. The inter-adjacent die image positional displacement information calculation unit 61 and the data processing unit 62 each include a memory having a capacity sufficient to store image data.

The controlling and processing system 80 at least includes a transport system controlling unit 81 for controlling the substrate transport system 20, an illumination light source controlling unit 82, and a sensor controlling unit 83 for synchronizing the first detection optical system 30 and a second detection optical system 40 with each other to acquire an image. The controlling and processing system 80 further includes a defect information processing unit 84 for carrying out a merge process and a classification process of defect information 600 outputted from the first image processing system 60 and a second image processing system 70. The controlling and processing system 80 further includes a control unit 89 for controlling the entire controlling and processing system 80. In FIG. 21A, also a power supply unit 86 including a control circuit for the optical filtering device 2000 is shown.

The interface system 90 at least includes a data accumulation section 91 for accumulating defect information 650 processed by and outputted from the controlling and processing system 80. The interface system 90 further includes an inputting section 92 for carrying out inspection condition setting and controlling process information inputting, and a display section 93 for displaying the defect information 650 and displaying the controlling process information.

Figure 21B:
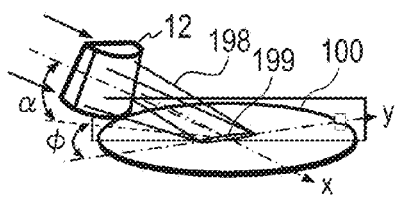
FIG. 21B is a perspective view illustrating a relationship between an aspherical lens for illuminating a linear region on the surface of a wafer on the one hand, and the wafer on the other hand.
Figure 21C:
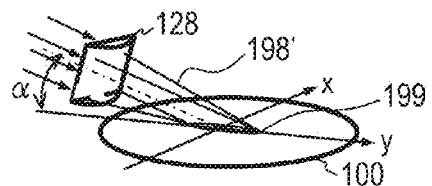
FIG. 21C is a perspective view illustrating a relationship between a cylindrical lens for illuminating a linear region on the surface of a wafer on the one hand, and the wafer on the other hand.

FIGS. 21B and 21C illustrate effects of a cone curved surface lens used as the shaping lens 12 in the present embodiment.

The shaping lens is used where a laser beam is irradiated from a direction rotated by φ with respect to the y-axis direction of the wafer and inclined by an angle α in the x-axis direction as illustrated in FIG. 21B. At this time, if the cone curved surface lens 12 is used, then an on-slit beam 199 having a minor axis in the x-axis direction and a major axis in the y-axis direction can be formed on the wafer 100.

On the other hand, where a laser beam is irradiated in an inclined relationship by an angle α in the z-axis direction from the y-axis direction of the wafer as illustrated in FIG. 21C, an ordinary cylindrical lens 128 is used. Therefore, an on-slit beam 199 having a minor axis in the x-axis direction and a major axis in the y-axis direction can be formed on the wafer 100.

Figure 22:
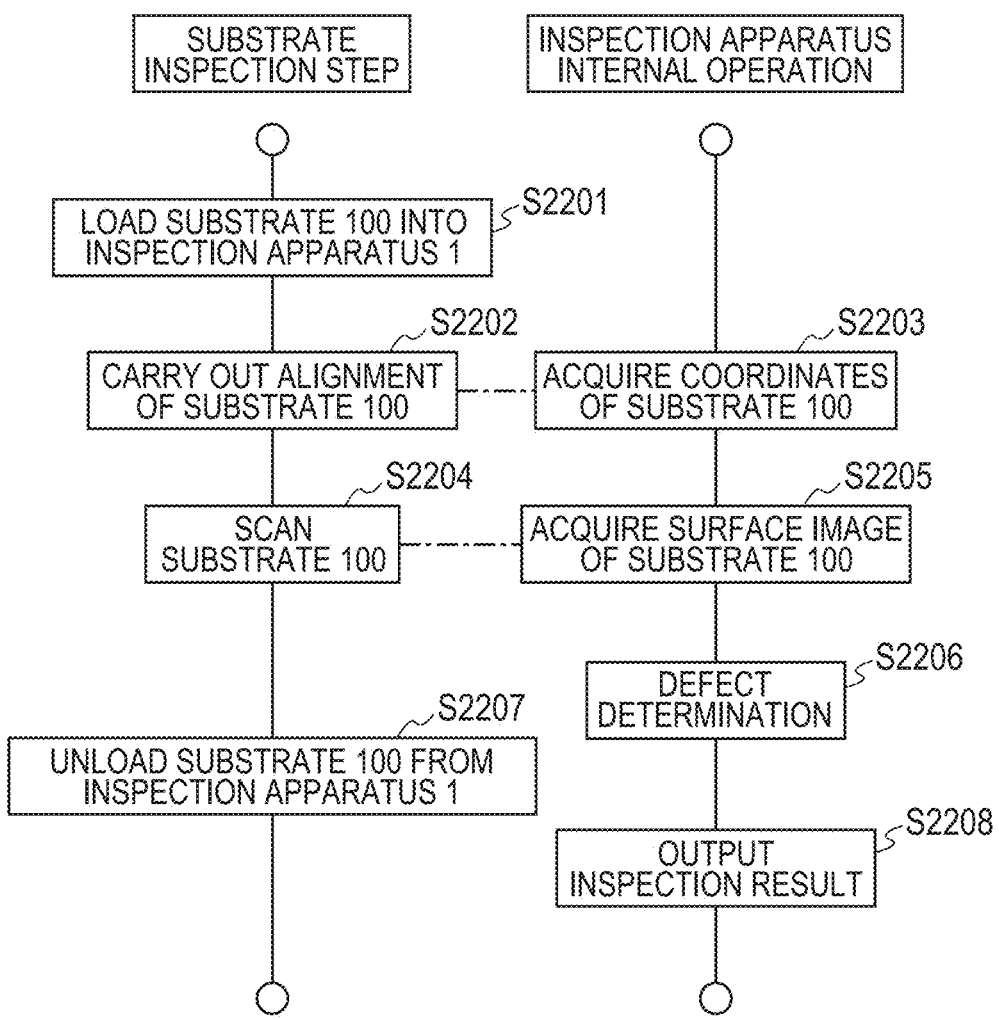
FIG. 22 is a flow chart of a substrate inspection step by an inspection apparatus which includes the optical filtering device which uses the micro shutter array according to the first embodiment.

A flow chart of a substrate inspection procedure in which the inspection apparatus according to the present embodiment is used is shown in FIG. 22.

Figure 20A:
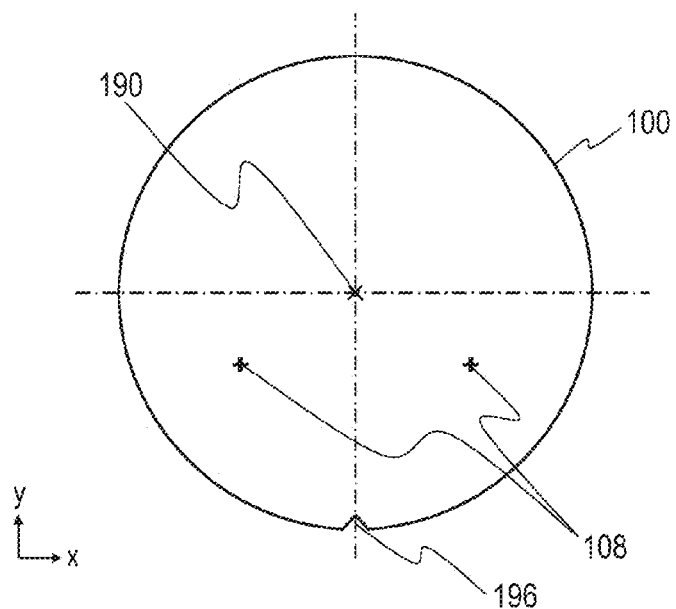
FIG. 20A is a plan view of a wafer in a state in which the position thereof is adjusted upon alignment of the wafer which is carried out before an inspection is started in a general inspection apparatus.

A substrate 100 is loaded into the inspection apparatus 1 (S2201) and held by the substrate chuck 24. The inspection apparatus 1 carries out an alignment operation (S2202) to eliminate an inclination of the substrate 100 and determines wafer origin coordinates 190 (refer to FIG. 20A) (S2203).

Then, the substrate 100 is scanned (S2204) to acquire an optical image 301 in the proximity of the surface of the substrate 100 (S2205). Based on the image thus obtained, a defect decision process (S2206) is carried out to detect presence or absence of a defect or a foreign article in the proximity of the surface of the substrate 100. As a method for the defect decision process, a method of comparing the acquired optical image 301 with a reference image stored in advance and detecting an unmatched portion between the images as a defect is applicable. Also a method of comparing a signal of the optical image 301 with a threshold value signal level set in advance and detecting a portion of the signal having a level higher than the threshold value signal level as a defect is applicable. The process at S2205 and the process at S2206 are executed asynchronously and independently of each other, and immediately after the acquisition of the optical image 301 in the proximity of the surface is completed, the substrate 100 is unloaded from the inspection apparatus 1 (S2207). Then, an inspection result is outputted (S2208).

Figure 23:
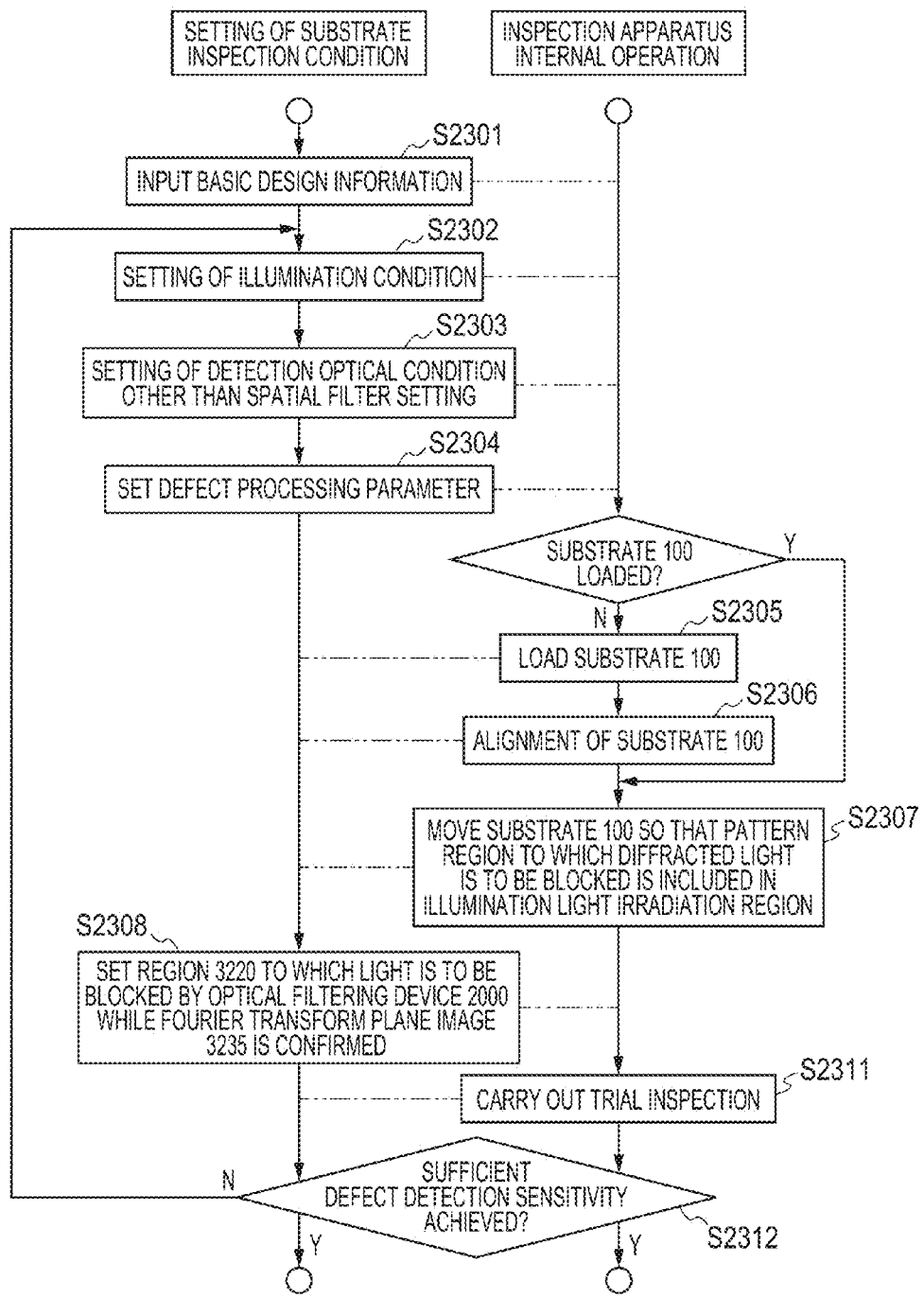
FIG. 23 is a flow chart illustrating a setting method of substrate inspection conditions by the inspection apparatus which includes the optical filtering device which uses the micro shutter array according to the first embodiment.

A setting flow of a substrate inspection condition in which the inspection apparatus according to the present invention is used is shown in FIG. 23.

First, basic design information of an inspection object wafer (substrate 100) such as a die size and an array is inputted from the inputting section 92 (S2301). Then, illumination conditions such as an illumination angle (direction, elevation angle) or illumination polarization is inputted from the inputting section 92 and set (S2302). Further, detection optical conditions (optical magnification, presence or absence of light analysis and so forth) other than spatial filter setting are inputted from the inputting section 92 and set (S2303). Then, a defect process parameter is set (S2304).

Here, if an inspection object wafer 100 is not yet loaded in the apparatus, then a wafer 100 is loaded (S2305) and an alignment operation is carried out (S2306). The inspection object wafer 100 is moved so that a region of the inspection object wafer 100 which includes, from among the patterns on the inspection object wafer 100, that pattern to which diffracted light is to be removed by the spatial filter (optical filtering device 2000) enters the region 199 in which illumination light is to be irradiated (S2307). While a Fourier transform plane image 3235 formed on the pupil plane of the objective lens 31 is observed at this time by the pupil plane observation system 310, a region 3220 to which light is to be blocked is set by the optical filtering device 2000 (S2308).

In the inspection conditions set as described above, the inspection object wafer 100 is subjected to trial inspection (S2311), and if sufficient defect detection sensitivity can be achieved (S2312), then the substrate inspection condition setting is ended. If the defect detection sensitivity is insufficient, then the processing returns to the setting of illumination conditions (S2302) to modify the set conditions.

Now, an operation flow when an inspection object substrate surface is illuminated with a sheet beam to detect an inspection image of the substrate surface using the optical sensor (TDI sensor) 35 is described with reference to FIG. 24.

First, a substrate 100 is loaded into the inspection apparatus 1 and fixed by the polarizing filter 34 (S2401).

Figure 20B:
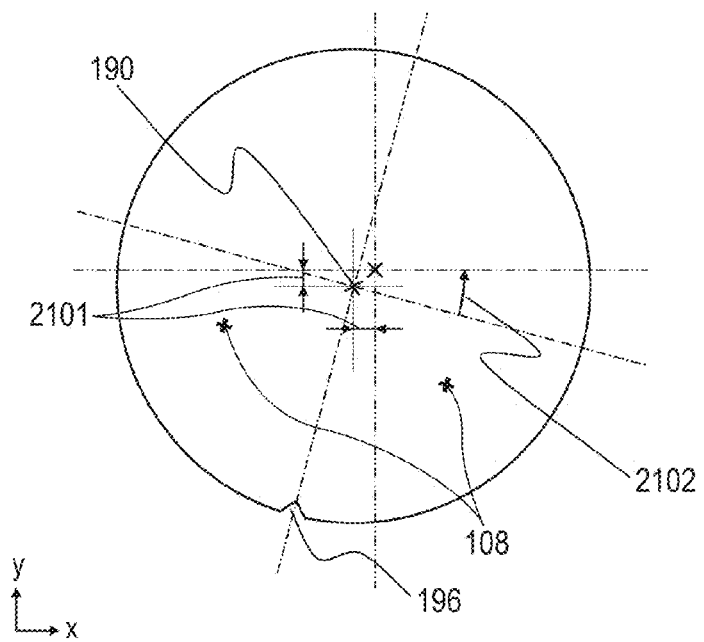
FIG. 20B is a plan view of a wafer in a state before the position thereof is adjusted upon alignment of the wafer which is carried out before an inspection is started in a general inspection apparatus.

Then, alignment marks 108 (refer to FIG. 20B) on the substrate 100 are used to carry out wafer alignment, and an offset 2101 (refer to FIG. 20B) and an inclination 2102 (refer to FIG. 20B) between the coordinates on the substrate 100 and the coordinates on the substrate scanning system are measured (S2402). If the inclination 2102 of the substrate 100 is equal to or greater than an angular threshold value set in advance, then the θ stage 25 is controlled by the transport system controlling unit 81 so that it is rotated in the opposite direction by the inclination 1302 to reduce the inclination to almost zero. Thereafter, alignment of the substrate 100 is carried out again and the offset 2101 between the coordinates on the substrate 100 and the coordinates on the substrate scanning system is measured again. Then, the optical filtering device 2000 is controlled to block light to the region set in advance (S2403).

Thereafter, the X stage 21 is scanned (S2404). The X stage 21 is moved at a substantially uniform speed while a laser beam shaped by the beam shaping lens 12 is irradiated upon the linear region 199 on the substrate 100. A shutter (not shown) of the light source 11 is opened within a range within which the region 199 irradiated by the laser beam shaped by the beam shaping lens 12 remains on the substrate 100 to carry out illumination by the laser beam shaped by the beam shaping lens 12 (S2405). The TDI sensor is rendered operative in synchronism with the scanning of the X stage 21 to acquire a surface image of the substrate 100 collectively (S2406). If one cycle of scanning of the X stage 21 is completed, then the Y stage 22 is moved by a width with which the surface of the substrate 100 can be measured collectively by the optical sensor 35 (S2408) to repetitively carry out scanning of the X stage 21 until a substrate surface image of the overall measurement region on the substrate designated in advance is acquired (S2407). If the acquisition of the substrate surface image of the overall measurement region on the substrate is completed, then the substrate 100 is unloaded (S2409), thereby completing the operation as the inspection apparatus.

Figure 24:
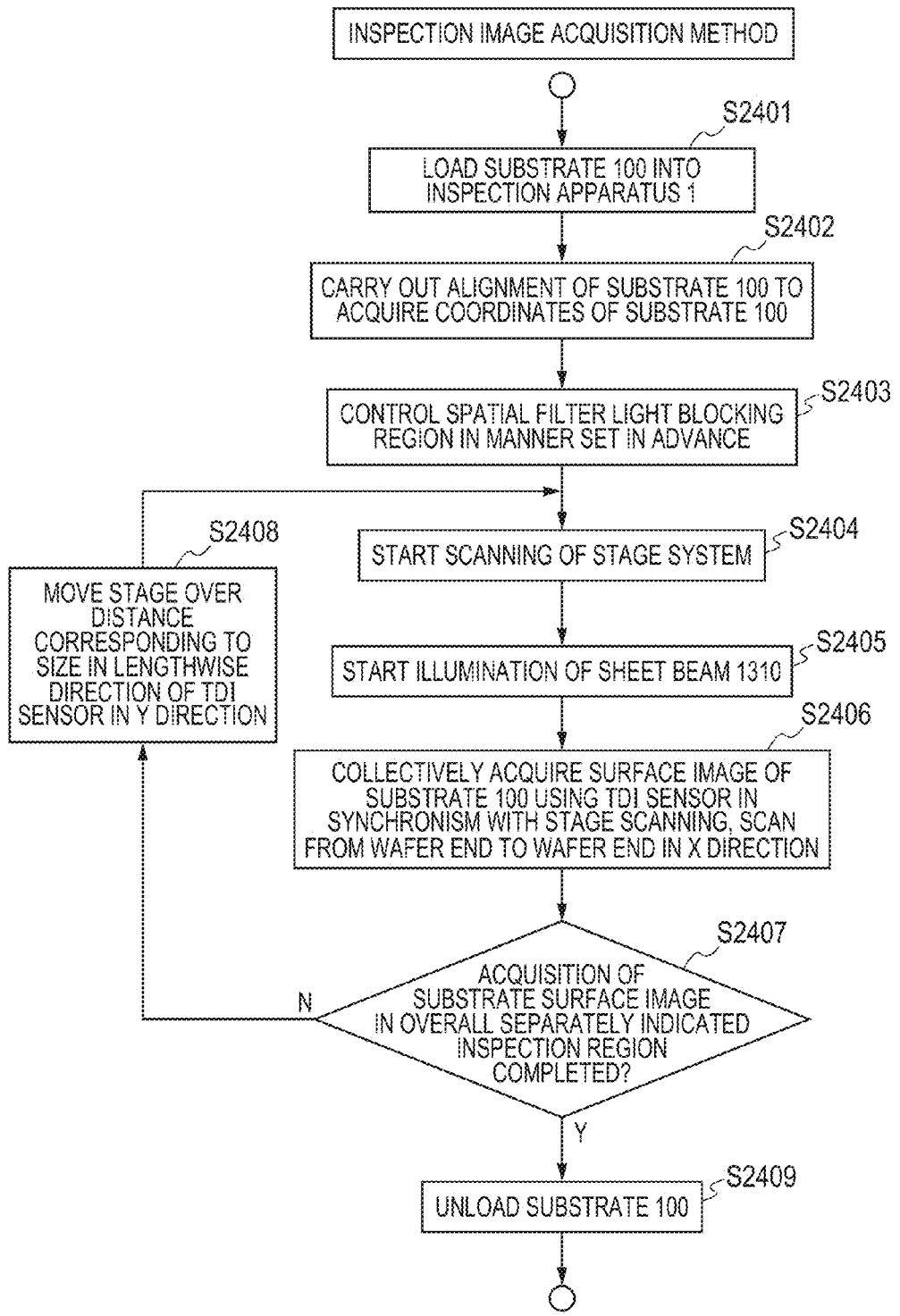
FIG. 24 is a flow chart illustrating a method of picking up an image of the surface of a substrate by the inspection apparatus which includes the optical filtering device which uses the micro shutter array according to the first embodiment.
Figure 25:
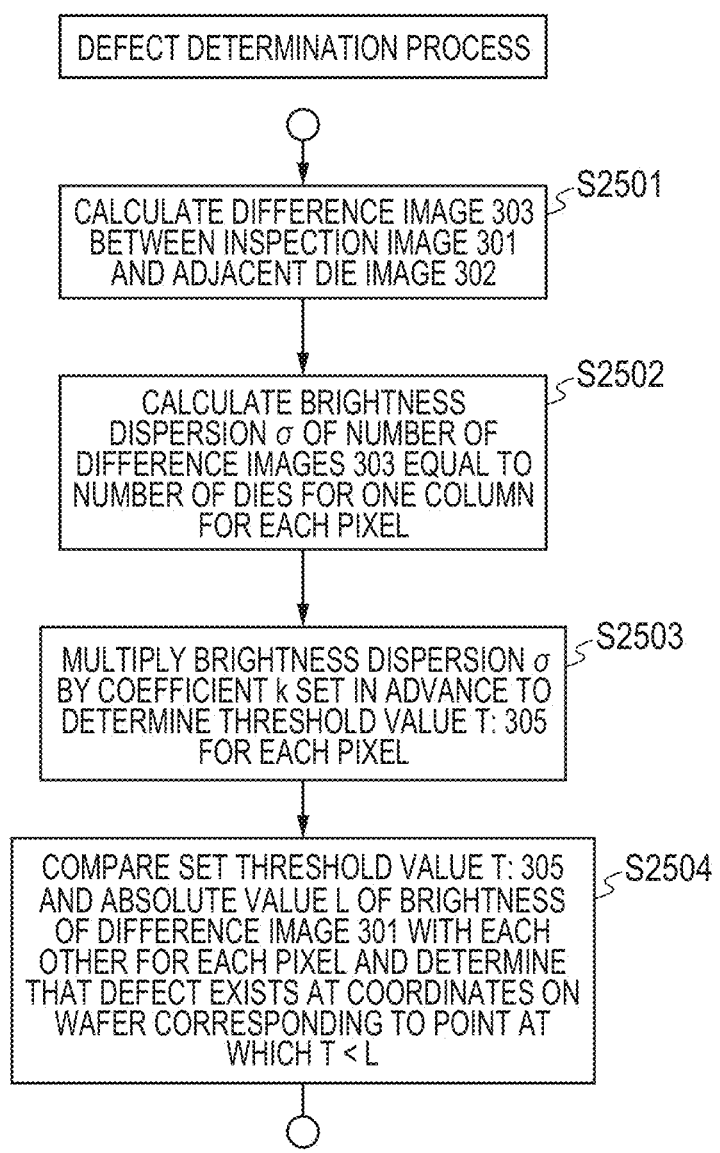
FIG. 25 is a flow chart illustrating a flow of a defect decision process by the inspection apparatus which includes the optical filtering device which uses the micro shutter array according to the first embodiment.

Now, an example of a flow of a defect decision process for detecting a defect using an image of the surface of the substrate 100 acquired collectively at S2406 of FIG. 24 is described with reference to FIGS. 25 and 26A to 26D.

Figure 26A:
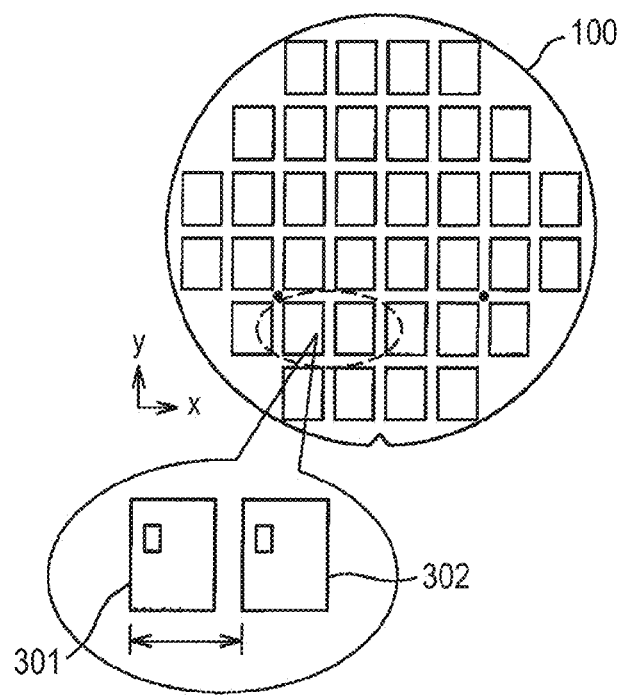
FIG. 26A is a plan view of an inspection object substrate.
Figure 26B:
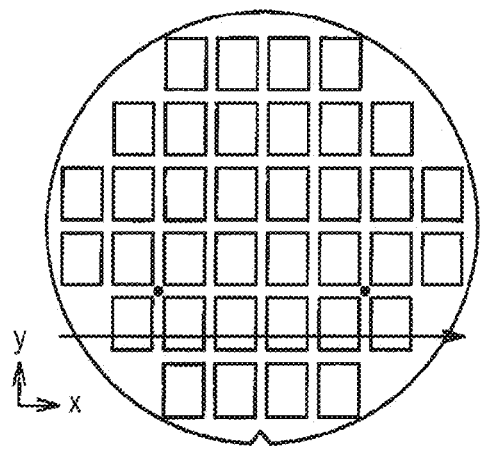
FIG. 26B is a plan view of the inspection object substrate illustrating a direction in which the inspection object substrate is inspected.
Figure 26C:
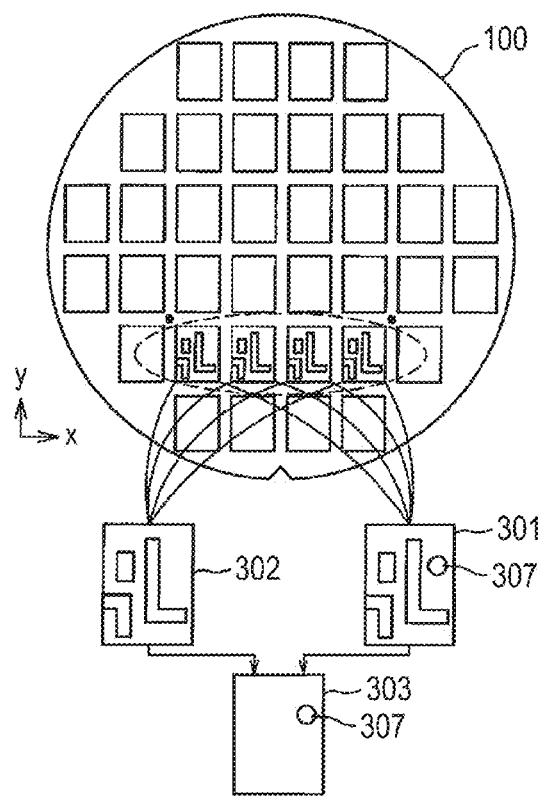
FIG. 26C is a plan view of the inspection object substrate, showing an enlarged pattern formed on each chip thereon.

First, while the X stage 21 is driven by the transport system controlling unit 81 to continuously move the substrate 100 in a direction indicated by an arrow mark in FIG. 26B with respect to the detection optical system 30, the substrate 100 is imaged by the detection optical system 30. From such an inspection image 301 obtained by the imaging as shown in FIG. 26A and an adjacent die image 302 to be used as a reference image, a difference image 303 is calculated using positional displacement information between the optical image 301 and the adjacent die image 302 as shown in FIG. 26C (S2601). This is repeated by a number of times corresponding to one cycle of scanning of the X stage (hereinafter referred to as for one column). A dispersion of the brightness value of the difference image 303 at a place corresponding to the same position in a plurality of dies for one column is calculated for each pixel (S2602).

Figure 26D:
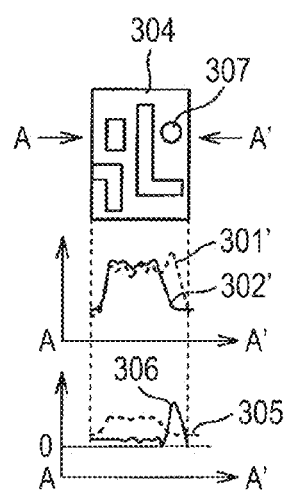
FIG. 26D is a diagram showing an inspection image and illustrating a signal waveform on line A-A' of an inspection image.

At the top in FIG. 26D, an image 304 obtained by overlapping the optical image 301 and the adjacent die image 302 with each other is shown. A graph at a middle stage indicates overlapping display of brightness values of the pixels of the optical image 301 on a line A-A' of the overlapping images on the upper stage and brightness values of the pixels of the adjacent die image 302. A signal waveform 301' of the optical image 301 which includes a defect 307 has a peak value at the portion thereof at which the defect exists with respect to a signal waveform 302' of the adjacent die image 302 which includes no defect 307. If the difference between the brightness values of the pixels of the optical image 301 and the brightness values of the pixels of the adjacent die image 302 is taken, then a waveform signal having a peak 306 at the defective portion like a graph on the lowermost stage in FIG. 26D is obtained.

Thereafter, the brightness value dispersion 304 is multiplied by a coefficient set in advance using the user interface to determine a defect decision threshold value 305 for a noticed pixel (S2603). In the example illustrated in FIG. 26D, at a place at which the difference between the brightness value of a pixel of the inspection image 301 and the brightness value of a corresponding pixel of the adjacent die image 302 is small, the defect decision threshold value 305 is set to a comparatively high value. On the other hand, at a place at which the difference is great, the defect decision threshold value 305 is set to a comparatively low value. Then, the determined defect decision threshold value 305 and the absolute value 306 of the brightness value of the difference image 303 are compared with each other for each pixel (graph at the middle stage in FIG. 26D). If the absolute value of the brightness value of the difference image is higher than the defect decision threshold value 305, then it is decided that a defect exists at the coordinates 307 on the substrate 100 corresponding to the pixel position (S2604). This flow is processed repetitively for an image in an inspection region designated in advance or for all acquired inspection images on the substrate 100 to carry out defect decision and calculate defect coordinates on the substrate 100.

It is to be noted that, in the foregoing description, after a difference image 304 between inter-adjacent die images is determined, a brightness value dispersion is determined, whereafter a threshold value is calculated from the brightness value dispersion and decision of a defect is carried out based on the threshold value. However, a different defect decision method may be used. In particular, such a method that image brightness values of two adjacent images 301 and 302 are adjusted first and a difference image is calculated similarly as in the process described above to carry out defect decision as disclosed in JP-A-2003-83907 (Patent Document 1) may be applied. Or such a method that defect decision is carried out based on data voted to a multidimensional space which has such features as a brightness value or a contrast of an inspection object image and a reference image on the axes thereof as disclosed in JP-A-2003-271927 (Patent Document 3) may be applied. In short, any method may be applied if brightness value information of an inspection image or difference information in brightness value between an inspection image and a reference image is used to carry out defect decision.

Figure 27:
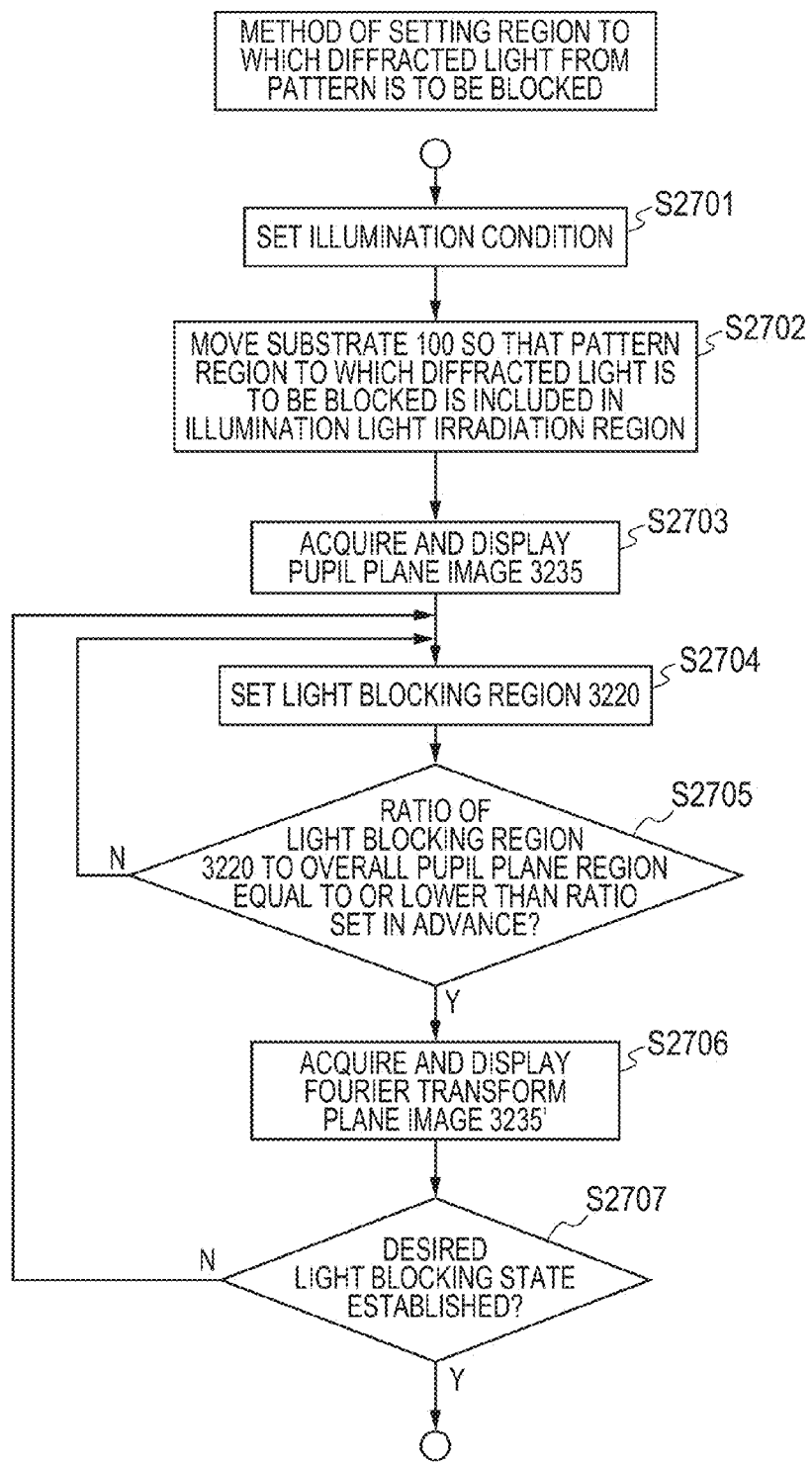
FIG. 27 is a flow chart illustrating a setting method of a spatial filter by the inspection apparatus which includes the optical filtering device which uses the micro shutter array according to the first embodiment.

Now, an embodiment of a flow for blocking diffracted light from a pattern formed in the proximity of the surface of a substrate 100 using the optical filtering device 2000 placed on the Fourier transform plane of the objective lens 31 is described with reference to FIG. 27.

First, illumination conditions to be used for inspection of the substrate 100 are set (S2701). Then, the stage systems are rendered operative to move the substrate 100 so that a pattern region to which refracted light is to be blocked is included in an illumination light irradiation region (S2702). Then, an intensity distribution image 3235 (refer to FIG. 28A) on the Fourier transform plane including diffracted light from the pattern is acquired by the pupil plane observation system 310 (S2703). At this time, all of those shutters 2001 on the optical filtering device 2000 whose opening and closing movements can be carried out normally are in an open state, and the optical filtering device 2000 is in a state in which all light incident to an opening 2004 thereof is transmitted through the optical filtering device 2000. When scattered right from a defective location of the substrate 100 is detected on the pupil plane, comparatively strong diffracted light generated by scattered light from patterns formed regularly on the substrate 100 degrades the detection sensitivity of the scattered light from the defective location. Therefore, in order to detect the scattered light from the defective location with a comparatively high sensitivity, it is effective to block comparatively strong diffracted light generated by scattered light from the patterns on the pupil plane. Based on the idea to detect a defect by blocking such strong diffracted light, the individual shutters 2001 of the optical filtering device 2000 are controlled by the power supply unit 86 to set a light blocking region of the optical filtering device 2000 (S2704).

Here, it is confirmed whether or not the Fourier transform plane is blocked against light exceeding a ratio set in advance (S2705). If the light blocking region is too great, then the resolution of the inspection image is prone to drop and the defect detection sensitivity accordingly drops. S2705 is implemented to prevent this.

Then, in the state in which the individual shutters 2001 of the optical filtering device 2000 are controlled (spatial filters are set), a light intensity distribution on the Fourier transform plane of the objective lens 31 is actually measured in the form of an image by the pupil plane observation system 310 (S2706). Then, it is confirmed that a region to which strong diffracted light has been incident is blocked against light, namely, the region is in a desired light blocking state 3235' (FIG. 18C) (S2702). If the desired light blocking state is established, then the light blocking region setting on the Fourier transform plane is completed. If the desired light blocking state is not established, then the processing returns to S2704, at which setting (adjustment) of the light blocking region of the optical filtering device 2000 is carried out.

Figure 28A:
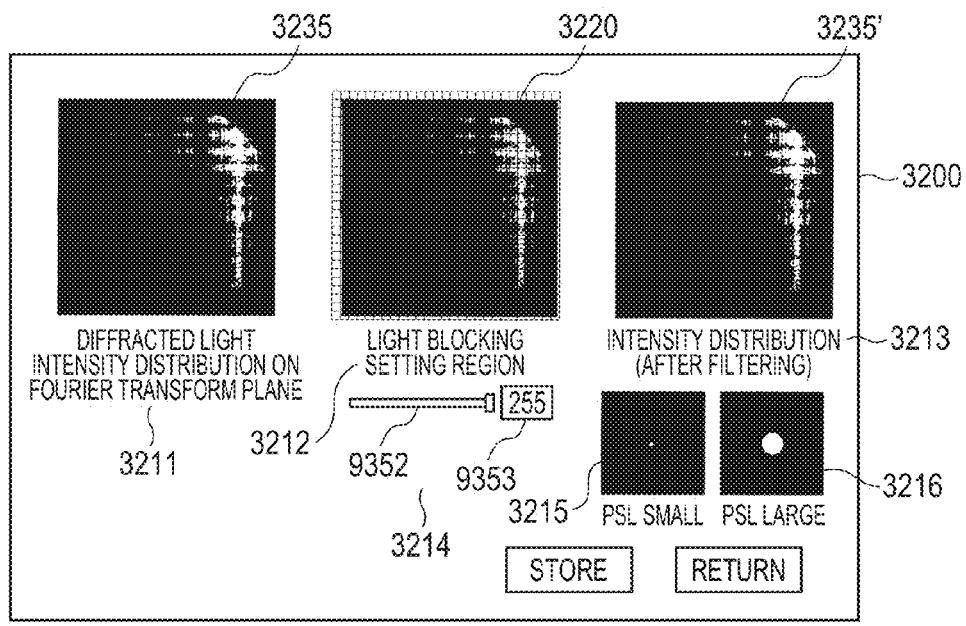
FIG. 28A is a front view of a screen image illustrating a diffracted light intensity distribution on the Fourier transform plane before setting of a spatial filter by the inspection apparatus which includes the optical filtering device which uses the micro shutter array according to the first embodiment.
Figure 28B:
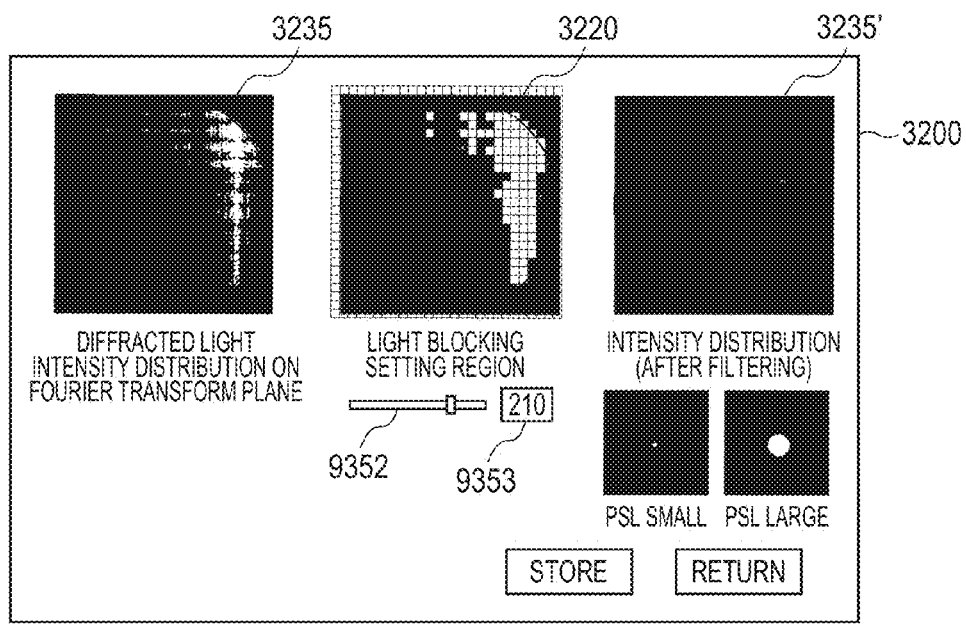
FIG. 28B is a front view showing a spatial filter setting region which is to be blocked against light by the optical filtering device.

FIGS. 28A and 28B show an example of a GUI screen image for light blocking region setting.

FIG. 28A shows the GUI screen image in an initial state. The GUI screen image 3200 includes a region 3211 for displaying an intensity distribution 3235 of diffracted light on the pupil plane from a pattern region set in advance. The GUI screen image 3200 further includes a region 3212 for displaying the intensity distribution 3235 of diffracted light in an overlapping relationship with the light blocking region 3220 of the spatial filtering device (spatial filter) 2000. The GUI screen image 3200 further includes a region 3213 for displaying an intensity distribution 3235' after filtering. Further, as a region 3214 for setting a light blocking threshold value for the diffracted light intensity, a slide bar 9352 and a window 9353 for numerical value inputting. By moving the slide bar 9352 or inputting a numerical value into the window 9353, a light blocking threshold value is set for each diffracted light intensity distribution.

FIG. 28B illustrates a state in which some region is set as a light blocking region. The pixels of the optical filtering device 2000 including those pixels whose brightness value is higher than the light blocking threshold value set in the region 3214 for setting a light blocking threshold value are automatically designated as light blocking region. Then, the light blocking region is displayed in the region 3212 for displaying the intensity distribution 3235 of diffracted light and the light blocking region 3220 of the spatial filter 2000 in an overlapping relationship with each other. Further, in the region 3213 for displaying the intensity distribution 3235' after filtering, the region blocked against light by the spatial filter 2000 is displayed in a painted out state.

It is to be noted that, as regards a setting method to a light blocking region, a desired pixel of the spatial filter 2000 may be clicked using a pointing device such as a mouse such that, simultaneously with turning ON/OFF of setting of a light blocking region, also the painting out is turned ON/OFF in place of setting in the region 3214 for setting the light blocking threshold value described hereinabove. Also it is possible to use this method to set light blocking ON/OFF of each pixel of the spatial filter 2000. The diffracted light intensity distribution 3235' on the Fourier transform plane after light blocking region setting on which the light blocking ON/OFF state of the pixels of the optical filtering device 2000 is reflected is displayed in the region 3213 for displaying the light blocking state 3235' after filtering. If the light blocking region becomes excessively great, then since this gives the fatal impact upon the defect detection accuracy, the setting is carried out with attention paid to this.

It is to be noted that a result of simulation calculation of an inspection image of PSL spheres which are standard defects where a light blocking region being currently set is applied may be indicated as illustrated in FIGS. 28A and 28B. The calculation method is such as follows.

The scattered light distribution on the pupil plane when PSL spheres being sprayed on the substrate 100 are illuminated is calculated in advance including a phase for each illumination condition, and imaging calculation is carried out using Fourier transform and inverse Fourier transform taking the light blocking region into consideration. At this time, since the scattered light distribution differs much depending upon the size of PSL spheres, even if light blocking conditions are same, the magnitude of the influence differs. In the present embodiment, by indicating simulation images 3215 and 3216 of two different kinds of large and small PSL spheres, the influence of the light blocking region being currently set upon the defect inspection sensitivity can be confirmed from a plurality of points of view.

Figure 29:
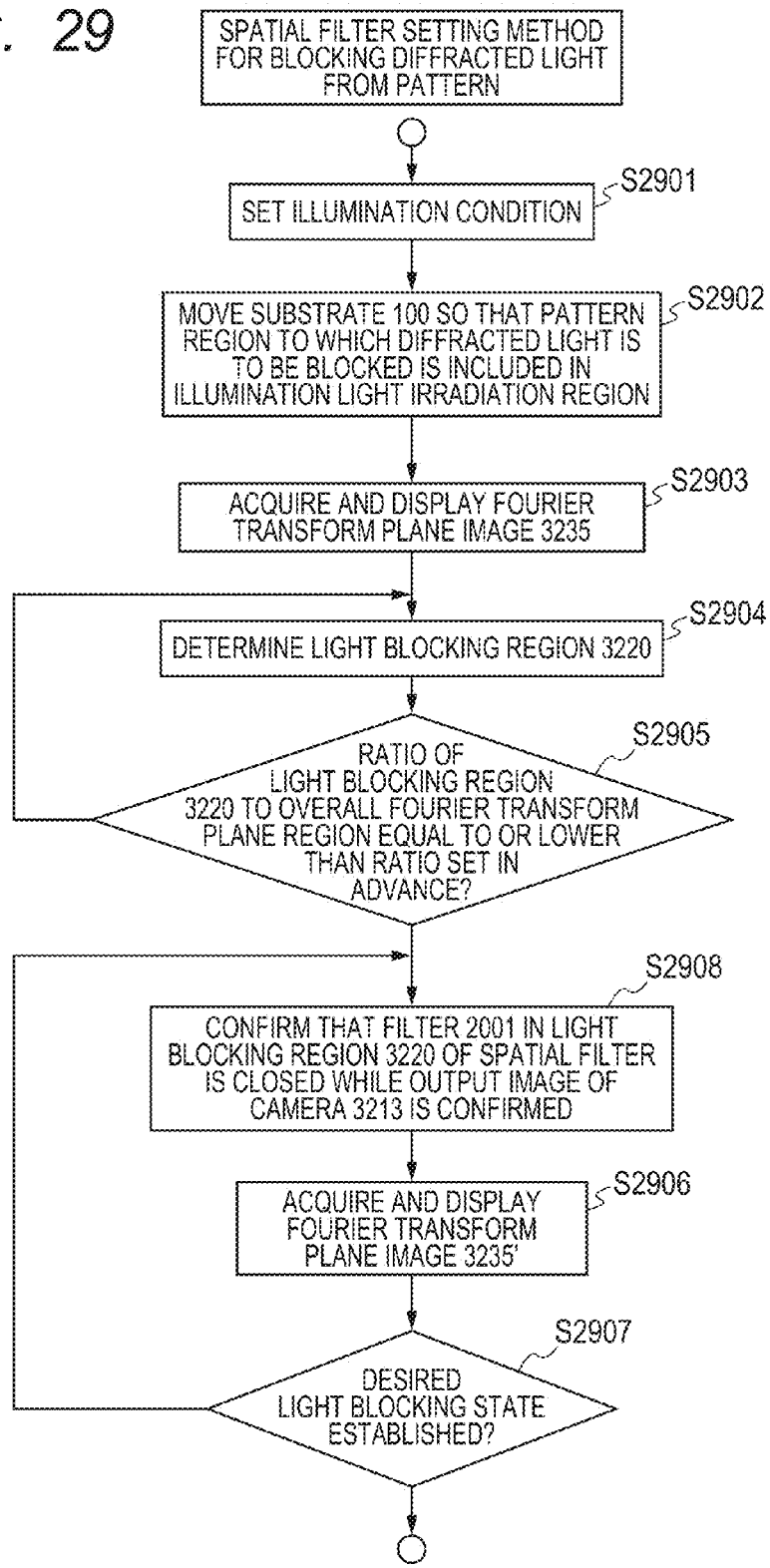
FIG. 29 is a flow chart illustrating a modification to the setting flow of a spatial filter by the inspection apparatus which includes the optical filtering device which uses the micro shutter array according to the first embodiment.

Now, a flow of setting a light blocking region for diffracted light from a pattern formed in the proximity of the surface of the substrate 100 using the two-dimensional filter system 32 according to the present embodiment placed on the Fourier transform plane of the objective lens 31 is described with reference to FIG. 29.

First, illumination conditions to be used for wafer inspection are set (S2901). Then, the stage systems are rendered operative to move the substrate 100 so that a pattern portion to which refracted light is to be blocked is included in the illumination light irradiation region (S2902). A light intensity distribution on the Fourier transform plane including refracted light from the pattern is acquired as an image 3235 (S2903). In order to detect scattered light from a defect of the substrate 100, the individual shutters of the optical filtering device 2000 are controlled by the power supply unit 86 to set a light blocking region 3220 based on the idea to block comparatively strong diffracted light generated by scattered light from the patterns formed regularly on the substrate 100 (S2904). Here, it is confirmed whether or not the Fourier transform plane is blocked against light exceeding a ratio set in advance (S2905). This is because, if the light blocking region is too great, then the resolution of the inspection image is prone to drop and the defect detection sensitivity accordingly drops.

Then, while an output image obtained by imaging an open/closed state of the shutters 2001 of the optical filtering device 2000 by the camera 3213 of the two-dimensional filter system 32 is confirmed, it is confirmed that the filter in the region 3220 of the spatial filter is closed (S2908). The light intensity distribution on the Fourier transform plane is measured as an image 3235' in the state in which the spatial filter is set again and is displayed on the screen (S2906). It is confirmed that strong diffracted light is blocked (S2907), and if the desired light blocking state is established, then the light blocking region setting on the Fourier transform plane is completed. However, if the desired light blocking state is not established, then the procedure beginning with S2908 is repeated until the desired light blocking state is established.

Figure 30:
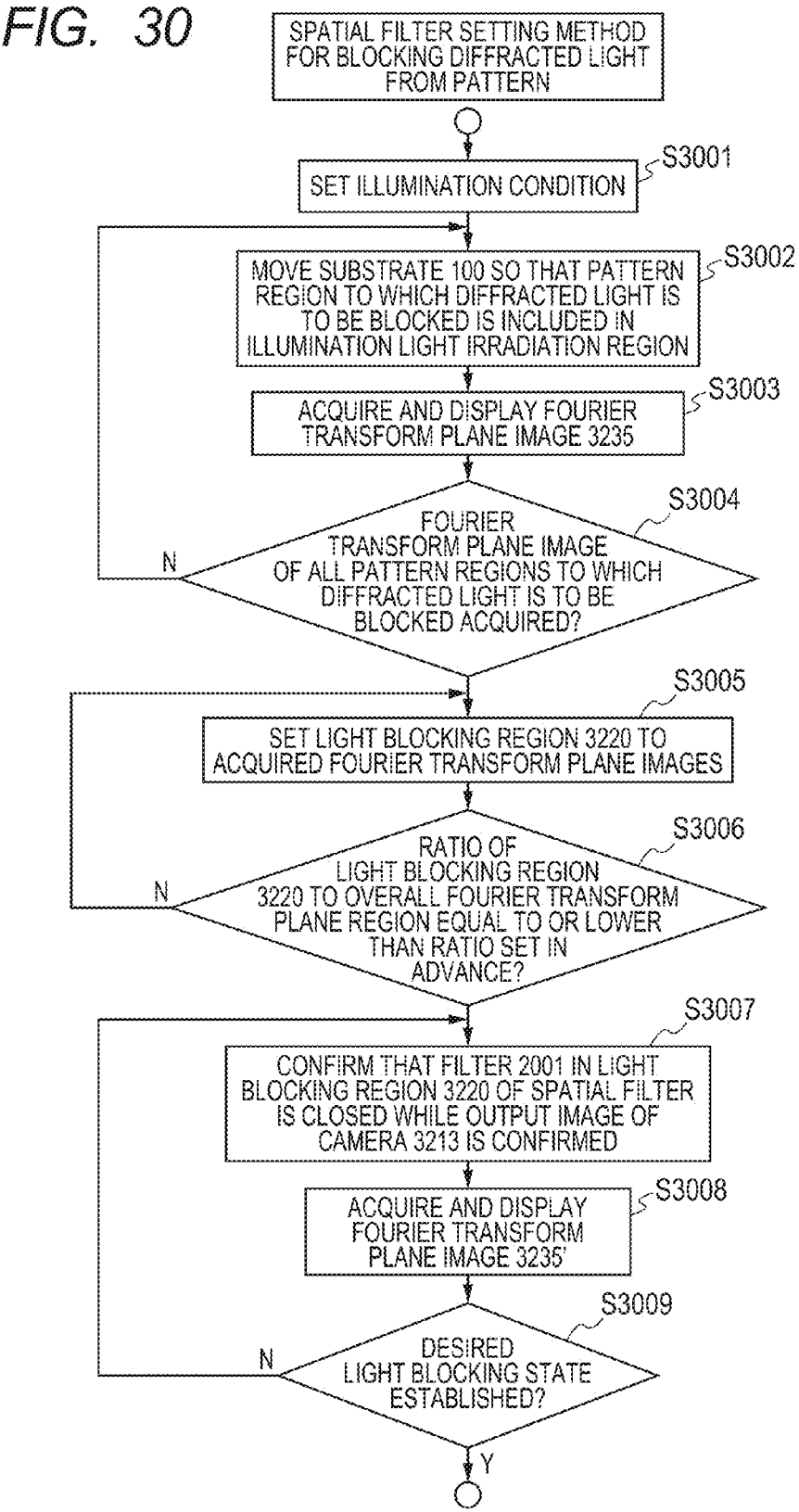
FIG. 30 is a flow chart illustrating a procedure for setting a light blocking region for blocking diffracted light from a pattern using a two-dimensional spatial filter system disposed on the Fourier transform plane of an objective lens in the inspection apparatus which includes the optical filtering device which uses the micro shutter array according to the first embodiment.

Now, a flow of setting a light blocking region, in which refracted light from the patterns formed in the proximity of the surface of the substrate 100 is to be blocked, using the two-dimensional filter system 32 according to the present embodiment installed on the Fourier transform plane of the objective lens 31 is described with reference to FIG. 30.

First, illumination conditions to be used for wafer inspection are set (S3001). Then, the stage systems are rendered operative to move the substrate 100 so that a pattern portion to which refracted light is to be blocked is included in the illumination light irradiation region (S3002). A light intensity distribution on the Fourier transform plane including refracted light from the pattern is acquired as an image 3235 (S3003). Here, a Fourier transform plane image of all pattern portions in which diffracted light is to be blocked is acquired (S3004). If an image of such pattern portions is not acquired, then the procedure at S3001 to S3003 is repeated.

Then, in order to detect scattered light from a defect of the substrate 100, the individual shutters of the optical filtering device 2000 are controlled by the power supply unit 86 to set a light blocking region 3220 based on the idea to block comparatively strong diffracted light generated by scattered light from the patterns formed regularly on the substrate 100 (S3005). At this time, the light blocking region 3220 is set based on the light intensity distribution on the Fourier transform plane obtained previously at S3003.

The light blocking regions obtained by repeating the procedure described above are merged to obtain a provisional light blocking region 3020. Here, it is confirmed whether or not the Fourier transform plane is blocked against light exceeding the ratio set in advance (S3006). This is because, if the light blocking region is too great, then the resolution of the inspection image is prone to drop and the defect detection sensitivity accordingly drops.

Thereafter, while an output image of the camera 3213 is confirmed, it is confirmed that the filters in the region 3220 of the spatial filter are closed (S3007), and a light intensity distribution on the Fourier transform plane is measured as an image 3235' in the state in which the spatial filter is set again and is displayed on the screen (S3008). It is confirmed on the screen image that strong refracted light is blocked, and if a desired light blocking state is established (S3009), then the light blocking region setting on the Fourier transform plane is completed. If the desired light blocking state is not established, then the procedure at S3007 to S3009 is repeated until the desired light blocking state is established.

Figure 31:
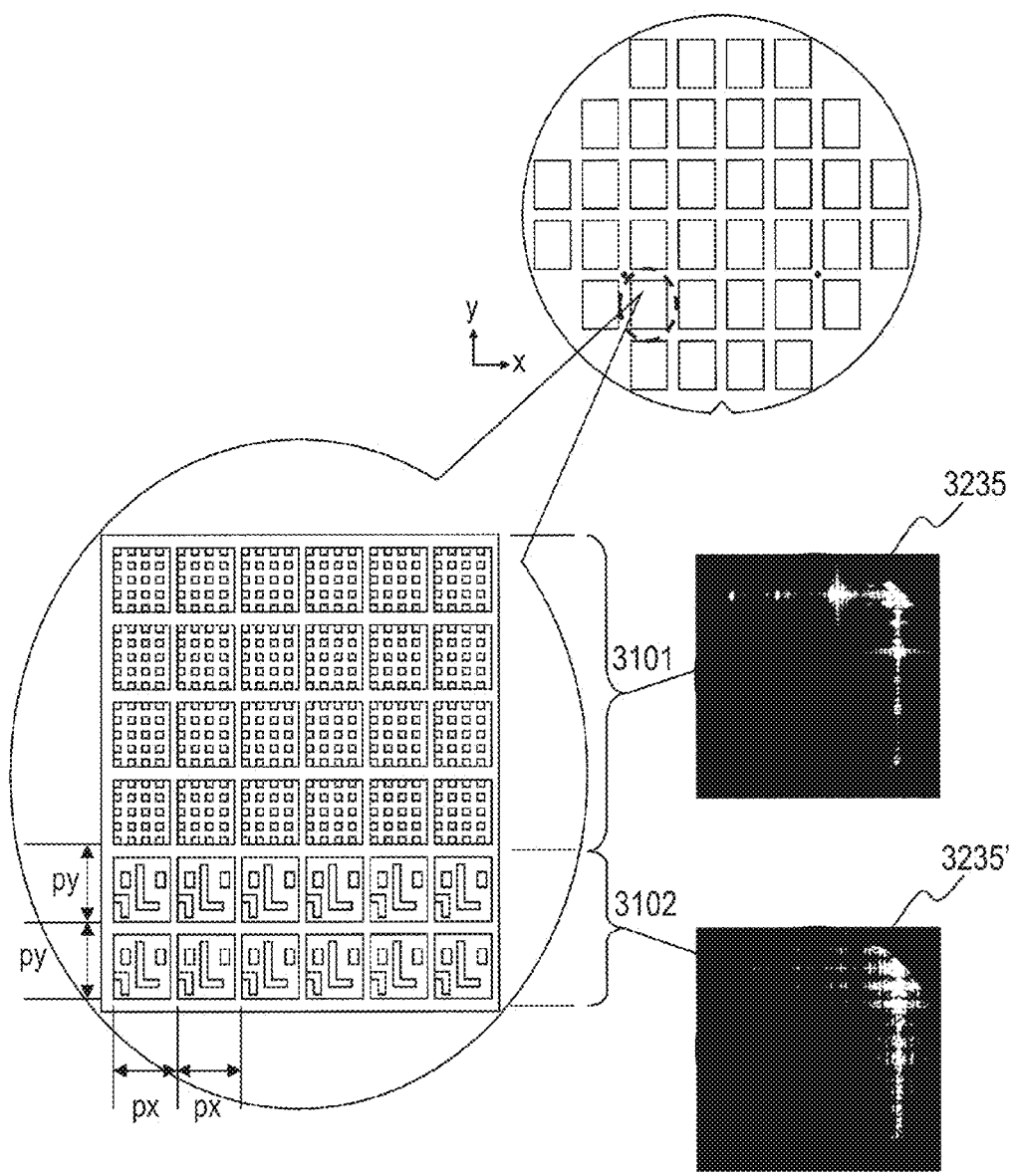
FIG. 31 is a plan view of a wafer illustrating arrangement of dies on a wafer, showing an example of a diffracted light distribution.

FIG. 31 is an image view of arrangement of certain dies of the substrate 100. While similar patterns are elaborated repetitively at pitches (px, py), depending upon a region, similar patterns are elaborated in a finer repetition period at a certain place (3101). At another place, on the other hand, no finer repetition patterns are elaborated (3102). Patterns of the emission direction of diffracted light of light irradiated upon the pattern regions are different from each other, and the intensity distribution of diffracted light from the region 3101 becomes like 3235 while the intensity distribution of diffracted light from the region 3102 becomes like 3235'. Accordingly, also required light blocking patterns are different.

In the following, the present embodiment wherein die regions are divided and light blocking patterns are set to the divided regions to detect a defect in a high sensitivity is described with reference to FIGS. 32A and 32B.

Figure 32A:
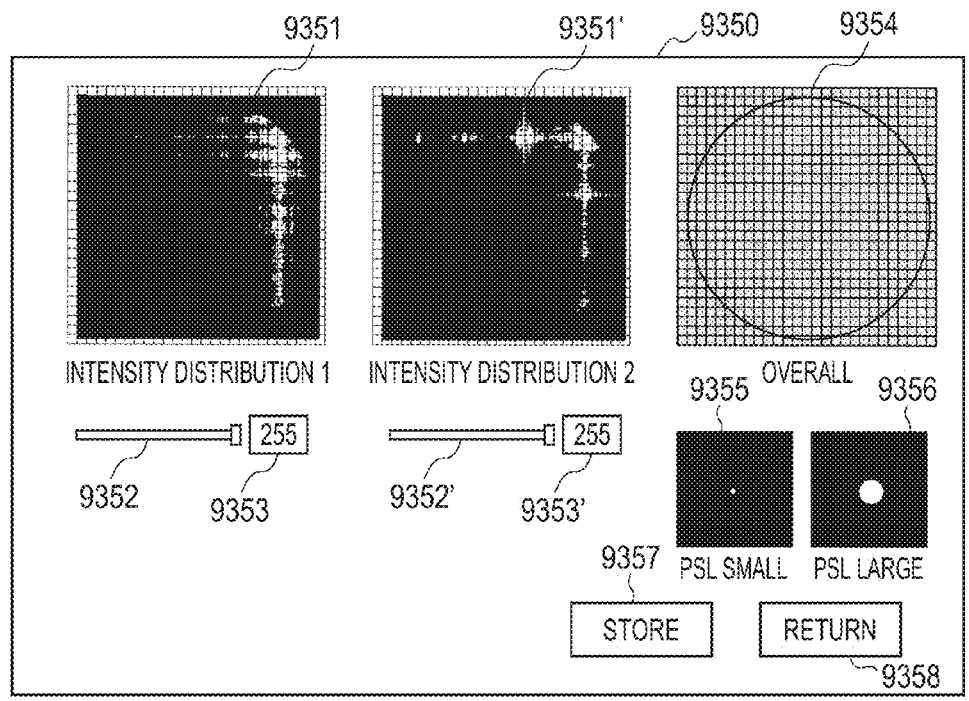
FIG. 32A is a front view of a screen image illustrating a diffracted light intensity distribution on the Fourier transform plane before setting of a spatial filter in a modification to a light blocking region setting user interface for a spatial filter by the inspection apparatus which includes the optical filtering device which uses the micro shutter array according to the first embodiment.

FIG. 32A shows a GUI screen image 9350 for light blocking region setting in an initial state. Intensity distributions 9351 and 9351' of diffracted light on the pupil plane from a plurality of pattern regions set in advance are displayed in an overlapping relationship with a light blocking region of the spatial filter. For each of the diffracted light intensity distributions 9351 and 9351', a light blocking threshold value is set by moving a slide bar 9352 or 9352' or inputting a numerical value into the window 9353 or 9353'. Those pixels of the spatial filter including pixels having a brightness value higher than the light blocking threshold value are automatically designated as a light blocking region. In the case of FIG. 32A, light blocking brightness values at the right end of slide bars 9352 and 9352' indicate maximum light blocking brightness values and indicate a state in which a light blocking region by the spatial film does not substantially exist. Further, in a region 9354, light blocking regions in the overall semiconductor wafer 100 are displayed.

Figure 32B:
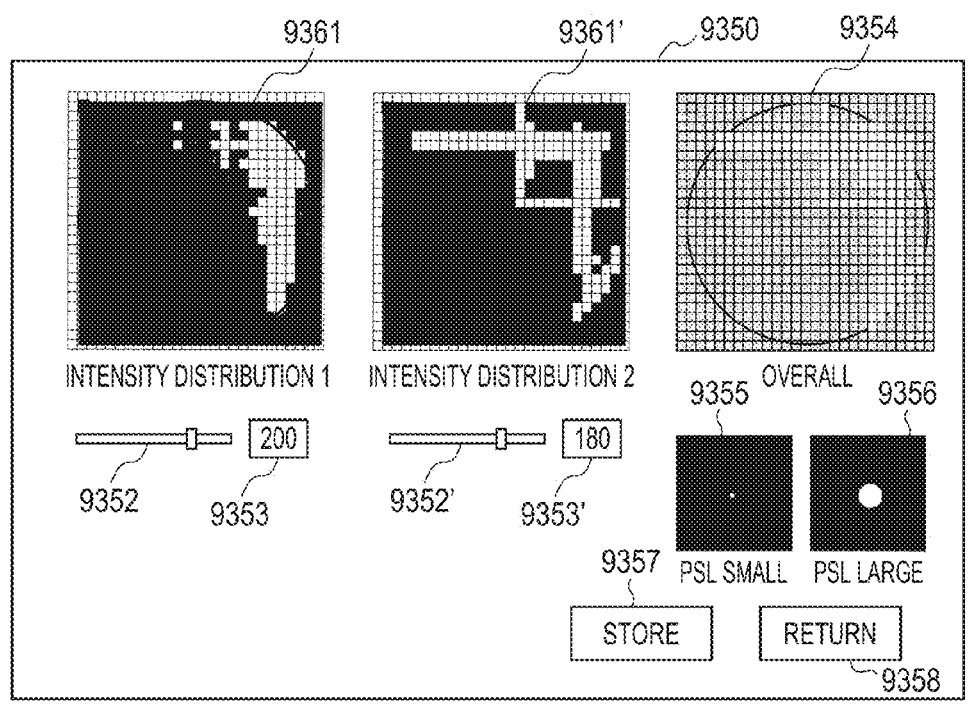
FIG. 32B is a front view of a screen image illustrating a spatial filter setting region to which light is blocked by an optical filtering device in the modification to the light blocking region setting user interface for a spatial filter by the inspection apparatus which includes the optical filtering device which uses the micro shutter array according to the first embodiment.

On the other hand, if the slide bar 9352 or 9352' is moved or a numerical value is inputted to the window 9353 or 9353' to adjust the light blocking threshold value, then the region in which light is blocked is displayed in an overlapping relationship with the intensity distribution of refracted light on the pupil plane like a region 9361 or 9361' shown in FIG. 32B.

It is to be noted that, as regards the light blocking region, if a pixel of a desired spatial filter is clicked using a pointing device such as a mouse, then painting out is turned ON/OFF. Also it is possible to use this method to set light blocking ON/OFF of each pixel.

On the GUI screen image 9350, a light blocking region obtained by merging the light blocking regions 9361 and 9361' set for the individual diffracted light intensity distributions over the overall substrate 100 is displayed in the region 9354 as shown in FIG. 32B. If the light blocking region becomes excessively great, then this has a fatal influence on the defect detection sensitivity. Therefore, the setting is carried out with attention paid to this.

It is to be noted that a result of simulation calculation of an inspection image of PSL spheres which are standard defects when the light blocking region being currently set is applied to the inspection may be indicated in regions 9355 and 9356 as shown in FIGS. 32A and 32B. The calculation is carried out by a method similar to that described hereinabove with reference to FIG. 28.

Further, on the GUI screen image 9350, a storage button 9357 for storing light blocking threshold values set by the slide bars 9352 and 9352' or the windows 9353 and 9353' and corresponding light blocking patterns 9361 and 9361' and a return button 9358 for restoring a state before one operation cycle on the screen image are displayed.

Figure 33:
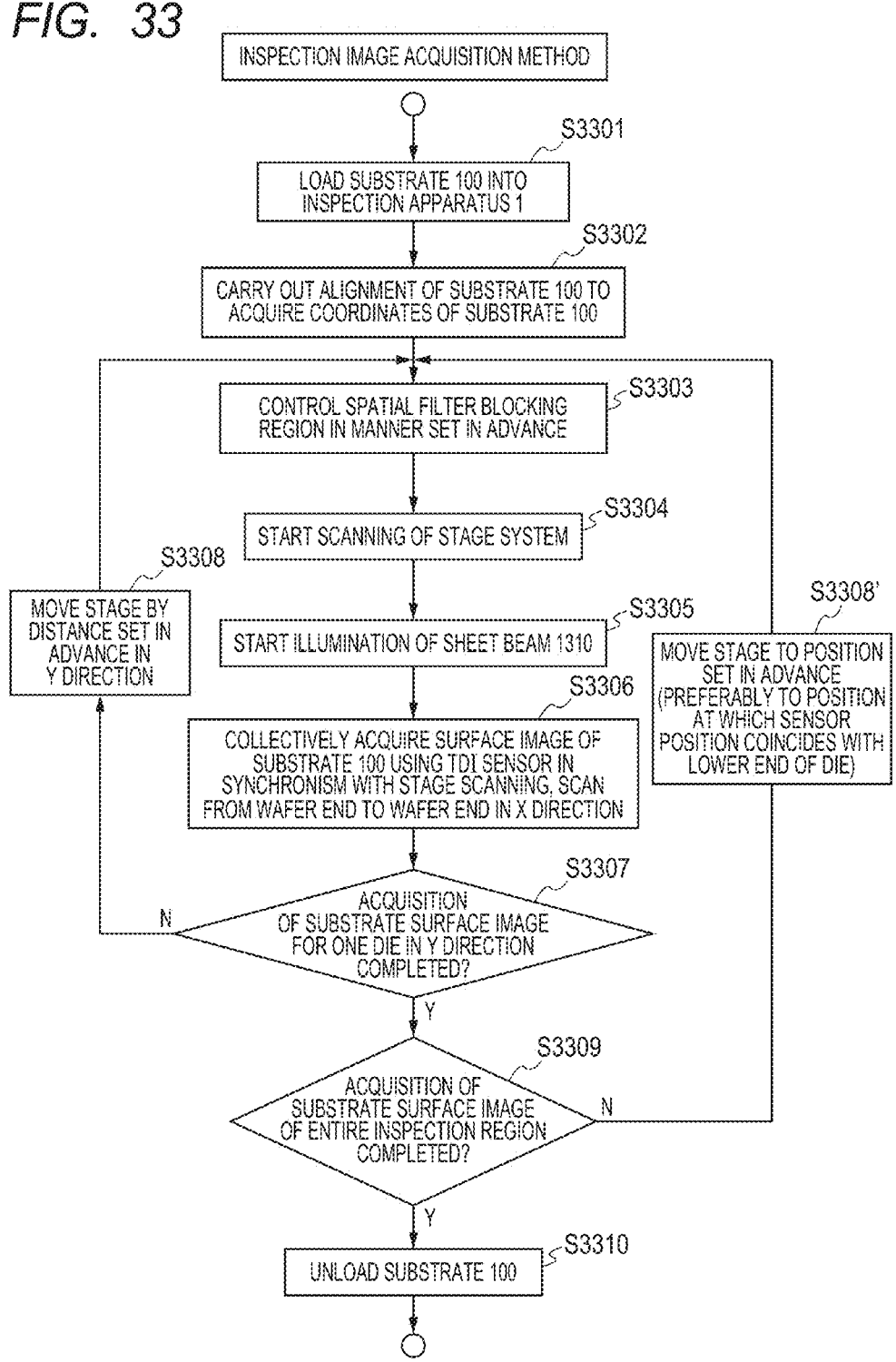
FIG. 33 is a flow chart illustrating another modification to the setting flow of a spatial filter by the inspection apparatus which includes the optical filtering device which uses the micro shutter array according to the first embodiment.

FIG. 33 shows an operation flow when the surface of an inspection object substrate is illuminated with a sheet beam and an inspection image of the substrate surface is detected using a TDI sensor.

First, a substrate 100 is loaded into the inspection apparatus 1 and fixed by a wafer chuck 24 (S3301).

Then, wafer alignment is carried out using the alignment marks 108 (refer to FIG. 20A) on the substrate 100, and the offset 2101 (refer to FIG. 20B) and the inclination 2102 between coordinates on the substrate 100 and coordinates on the substrate scanning system are measured (S3302). If the inclination 2102 is greater than an angular threshold value set in advance, then the θ stage 25 is rotated in the reverse direction by the inclination 2102 so that the inclination may be reduced to almost zero. Thereafter, alignment of the substrate is carried out again and the offset 2101 between the coordinates on the substrate 100 and the coordinates on the substrate scanning system is measured again.

Then, the optical filtering device 2000 is controlled to block light to the region set in advance (S3303). Then, the X stage 21 is scanned (S3304). The X stage 21 is moved substantially at a uniform speed while the sheet beam 198 continues to be irradiated upon the substrate 100. A shutter 13 of the laser light source 11 is opened within a range within which the illumination region 199 on the wafer 100 by the sheet beam 198 is on the substrate 100 and illumination by the sheet beam 198 is carried out (S3305). At this time, the optical sensor (TDI sensor) 35 is rendered operative in synchronism with the scanning of the X stage 21 to collectively acquire a surface image of the substrate 100 (S3306).

After the scanning of the X stage 21 by one cycle is completed, it is checked whether acquisition of a substrate surface image for one die in the Y direction is completed (S3307). If such acquisition is not completed (in the case of NO at S3307), the stage is moved by a distance set in advance in the Y direction (S3308). At this time, since the light blocking region of the spatial filter can be set for each cycle of scanning, where an operation for a different light blocking pattern is to be carried out subsequently, the processing is returned to S3303 to control the optical filtering device 2000 so that the region set in advance is blocked against light. Thereafter, the operations at S3304 to S3307 are executed repetitively.

After acquisition of substrate surface images for one die in the Y direction is completed (in the case of YES at S3307), it is checked whether or not acquisition of a substrate surface image in the overall measurement region on the substrate is completed (S3309). If such acquisition is not completed (in the case of NO at S3309), then the stage is moved to the proximity of a position at which the sensor position is in register with a lower end of a next die in the Y direction (S3308'). Then, the scanning at S3303 to S3309 is carried out repetitively. Here, if acquisition of a substrate surface image over the overall measurement region on the substrate designated in advance is completed (in the case of YES at S3309), then the substrate 100 is unloaded (S3310), thereby ending the operation as the inspection apparatus.

Figure 34:
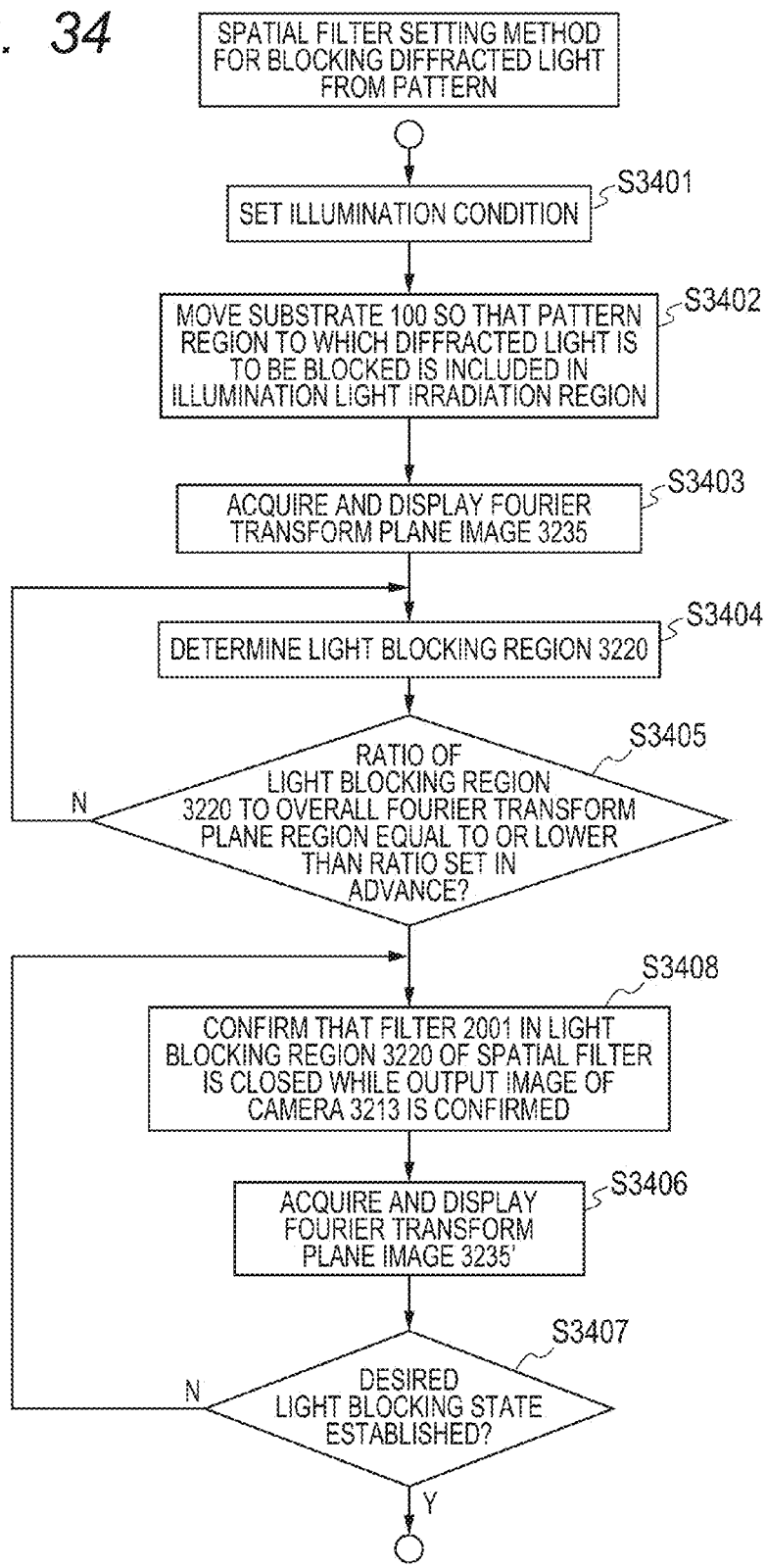
FIG. 34 is a flow chart illustrating an operation flow for carrying out transition from a certain light blocking state to another light blocking state at a high speed in the inspection apparatus which includes the optical filtering device which uses the micro shutter array according to the first embodiment.

Now, a flow for setting a light blocking region with regard to diffracted light from a pattern formed in the proximity of the surface of the substrate 100 using the two-dimensional filter system 32 according to the present embodiment installed on the Fourier transform plane is described with reference to FIG. 34.

First, illumination conditions to be used for inspection of a substrate 100 are set (S3401). Then, the stage system is rendered operative to move the substrate 100 so that a pattern portion to which refracted light is to be blocked is included in the illumination light irradiation region (S3402). A light intensity distribution on the Fourier transform plane including refracted light from the pattern is acquired as an image 3235 (S3403). The acquired image is displayed in the regions 3211 and 3212 on the GUI screen image 3200 as described hereinabove with reference to FIG. 28A, and a slide bar 9352 displayed in the region 3214 is operated on the region 3212 or a numerical value is inputted from a window 9353 for numerical value inputting to set a light blocking region of the optical filtering device 2000 based on the concept to block strong diffracted light (S3404). Here, it is confirmed whether or not the Fourier transform plane is blocked against light exceeding a ratio set in advance to the region 3220 of the optical filtering device 2000 on the screen image in which the light blocking region of the optical filtering device 200 shown in FIG. 28B is set (S3405). This is because, if the light blocking region is too great, then the resolution of the inspection image is prone to drop and the defect detection sensitivity accordingly drops.

Then, while an output image of the camera 3213 is confirmed on the GUI screen image 3200 on which the light blocking region of the optical filtering device 2000 shown in FIG. 28B is set, it is confirmed that the filters in the region 3220 of the optical filtering device 2000 are closed (S3406). Then, in the state in which the optical filtering device 2000 is set, a light intensity distribution on the Fourier transform plane is measured as an image 3235' again and displayed on the screen (S3407). Then, it is confirmed on the GUI screen image 3200 that strong diffracted light is blocked (S3408), and if a desired light blocking state is established (in the case of YES at S3408), then the light blocking region setting on the Fourier transform plane is completed. If a desired light blocking state is not established (in the case of NO at S3408), then the procedure at S3406 to S3408 described above is repeated until a desired light blocking state is established.

A modification to the light blocking region setting method of the optical filtering device 2000 in the present embodiment is described with reference to FIGS. 35A to 35C.

Figure 35A:
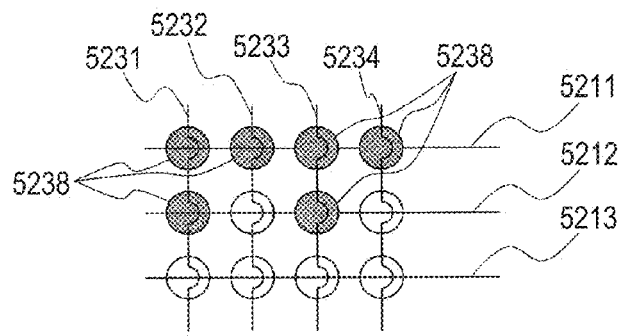
FIG. 35A is a plan view illustrating arrangement of the micro shutter array in the first embodiment.
Figure 35B:
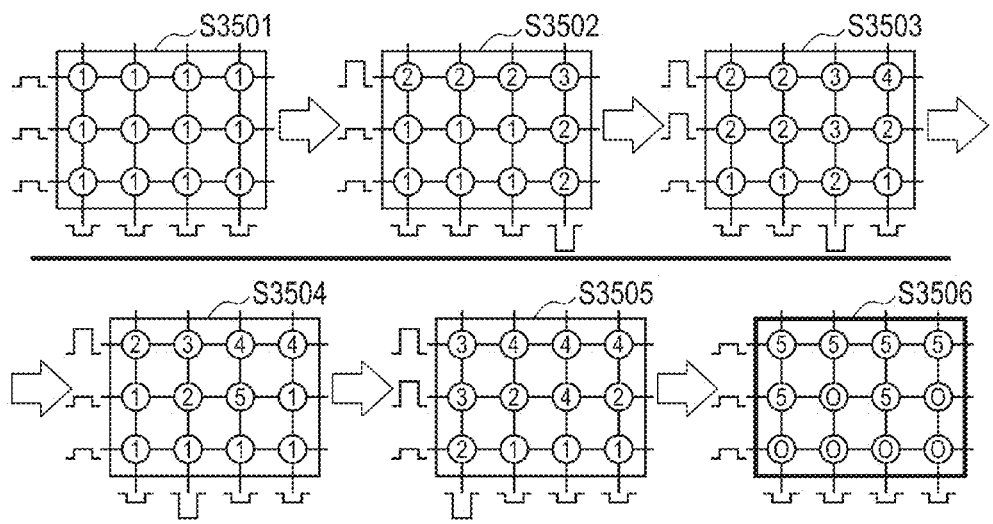
FIG. 35B is a plan view illustrating a flow of forming a desired light blocking state through four intermediate stages by opening all of those shutters (latched open state) in the closed state which remain after desired shutters of the micro shutter array are successively placed from the closed state to the latched closed state in order from the right side.
Figure 35C:
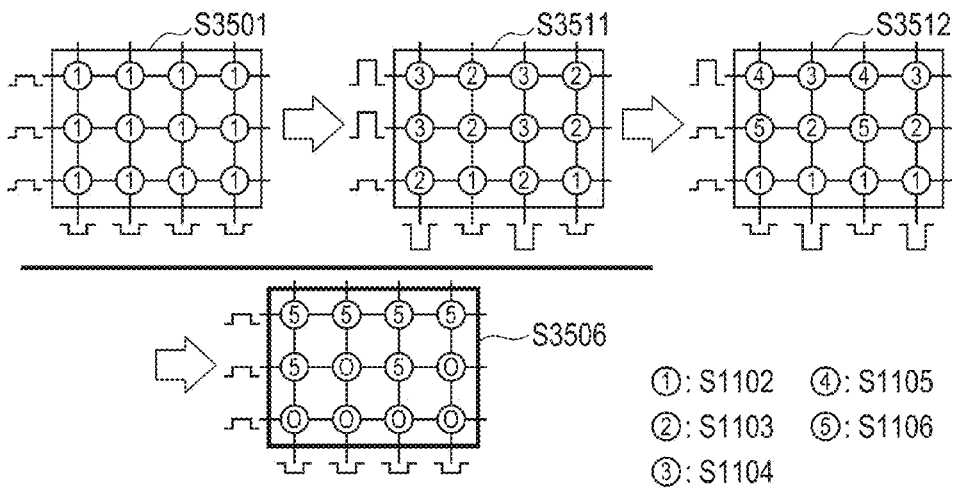
FIG. 35C is a plan view illustrating a flow of forming a desired light blocking state through two intermediate stages by opening all of those shutters (latched open state) in the closed state which remain after desired shutters of the micro shutter array are successively placed from the closed state to the latched closed state in order from the right side.

For example, if the final opening or closing state of the shutters is white (open) and gray (closed) of FIG. 35A, then according to the light blocking region setting method illustrated in FIG. 12, a desired light blocking state is obtained by causing desired shutters to transit from the closed state to the latched closed state in order from the right side in FIG. 35B and then opening all of the remaining shutters in the closed state (to the latched open state).

On the other hand, as described hereinabove with reference to FIGS. 8A to 8F and 11A and 11B, according to the method of the present embodiment, a shutter which is placed into the latched closed state once maintains the latched closed state unless a special process by which the application voltage difference becomes smaller than $V_{rel}$ is carried out. Therefore, where the positional relationship of shutters to be placed into the latch closed state is same like shutters in the first and third columns or shutters in the second and fourth columns from the left in FIG. 35A, it is possible to cause transition of latches from the closed state to latched closed state to be carried out simultaneously for the two columns by setting the potential for the first and third columns in the column direction to a high potential for more than a certain period of time.

If this method is used, then the time for the transition of all shutters included in a desired light blocking region from the closed state to latched closed state can be reduced. More particularly, if the state transition is carried out in such an order as S3511→S3512→S3506, then by the procedure illustrated in FIG. 35B, the final latched closed state is obtained through four intermediate stages. However, by the method illustrated in FIG. 35C, the final latched closed state is obtained through two intermediate stages. Therefore, it can be recognized that the state transition time is reduced.

Figure 36:
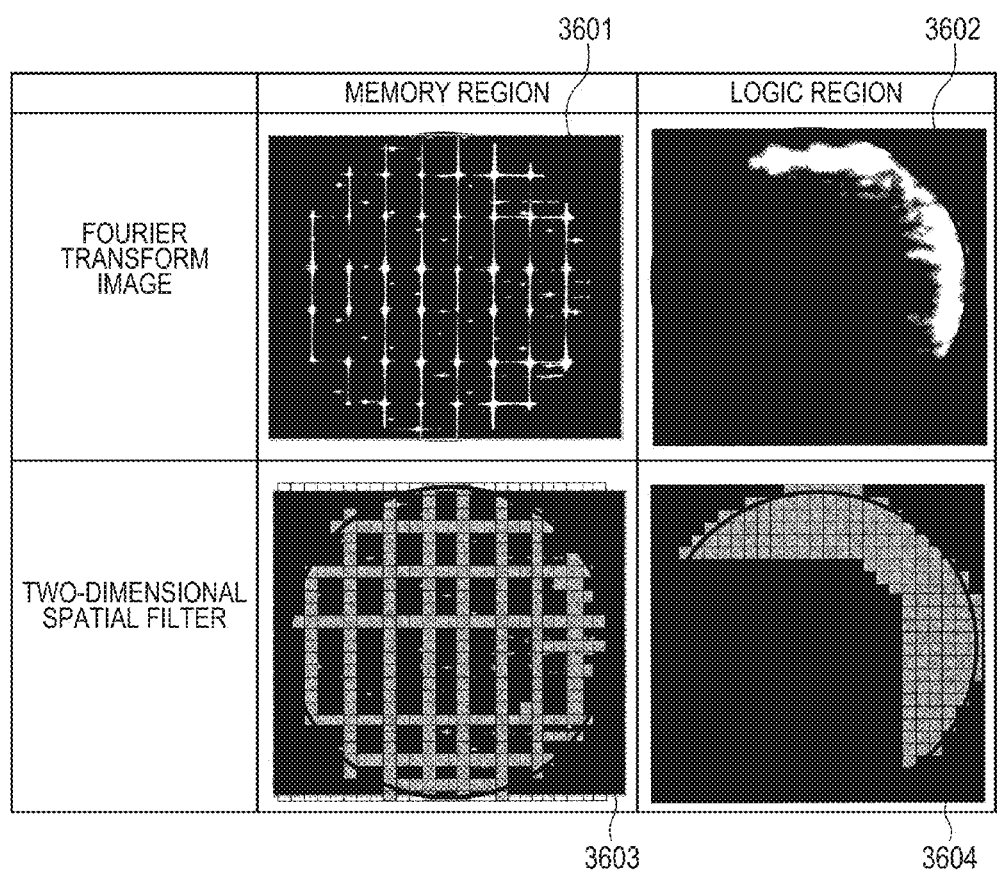
FIG. 36 is a diagram illustrating a diffracted light intensity distribution on the Fourier transform plane of an object lens when a laser beam is irradiated upon a memory sell region and a logic region of a semiconductor wafer and a pattern shape of a two-dimensional spatial filter corresponding to the diffracted light intensity distribution.

FIG. 36 illustrates an example of a diffracted light intensity distribution on the Fourier transform plane of the objective lens 31 when a laser beam is irradiated upon a memory cell region and a logic region of a semiconductor wafer (substrate 100). In a Fourier transform image 3601 of the memory cell region (memory region), since a place at which diffracted light is intense appears repetitively, the time reduction effect for the transition from the closed state to latched state of the shutters in the light blocking region for forming a light blocking pattern 3603 by the two-dimensional spatial filter using the speeding up technique disclosed in the present modification is achieved notably. Also in a Fourier transform image 3602 in the logic region, when a light blocking region which is great in the column and row directions is set based on a light blocking pattern 3604 by the two-dimensional spatial filter, the effect of speeding up of the light blocking state transition by the method of the present modification is achieved notably.

Figure 37A:
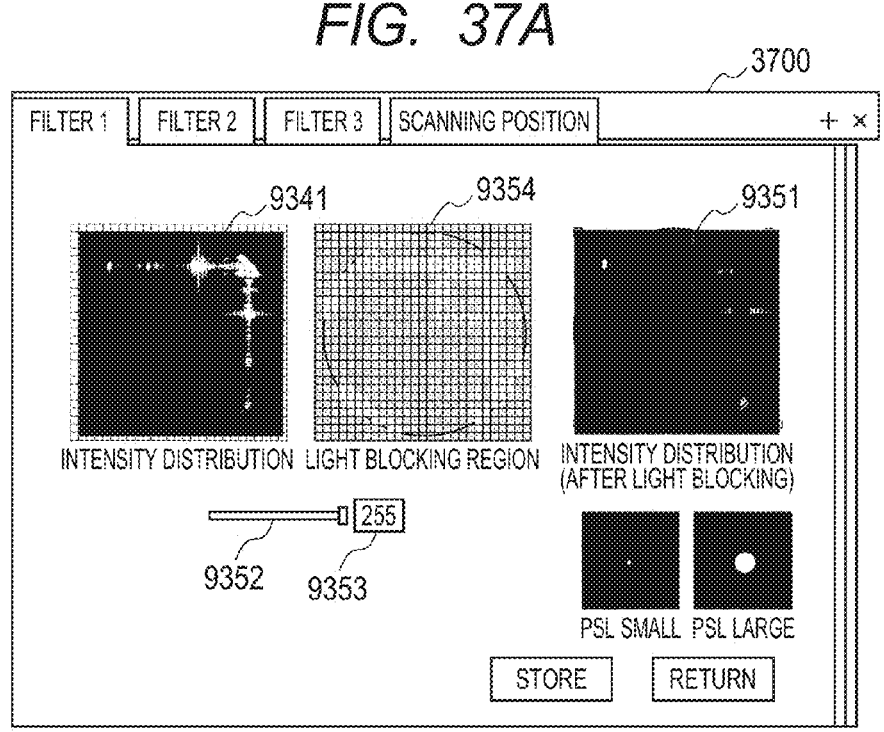
FIG. 37A is a front view of a screen image showing a light blocking region setting user interface for setting a spatial filter by the inspection apparatus which includes the optical filtering device which uses the micro shutter array according to the first embodiment.
Figure 37B:
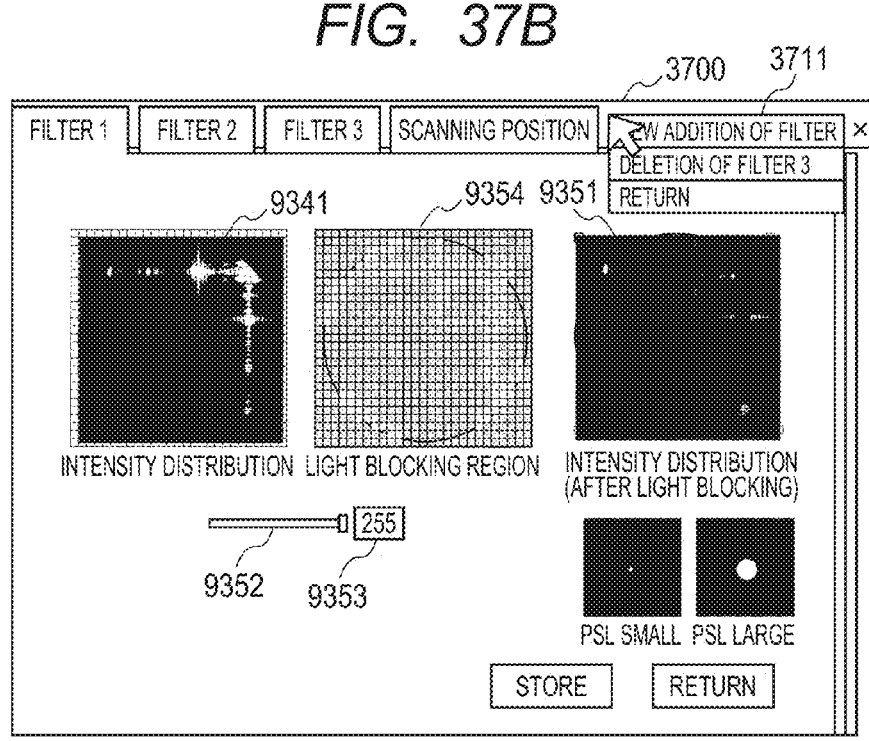
FIG. 37B is a front view of a screen image which displays a plurality of tabs in order to make it possible to set a plurality of light blocking region patterns in a modification to the light blocking region setting user interface for setting a spatial filter by the inspection apparatus which includes the optical filtering device which uses the micro shutter array.

FIGS. 37A and 37B show an embodiment of a user interface screen image (GUI screen image) 3700 for light blocking region setting. The configuration of the GUI screen image 3700 shown in FIG. 37A is same as the configuration of the GUI screen image 3200 described hereinabove with reference to FIG. 28A. However, in the present modification, in order to make it possible to set a plurality of light blocking region patterns as shown in FIG. 37B, a plurality of tabs 3711 are displayed. On the GUI screen image 3700, a light blocking pattern stored in storage means is set on each tab 3711. The number of tabs 3711 can be increased or decreased so that the number of light blocking region patterns can be increased or decreased. The setting method of each light blocking region is same as the contents described hereinabove with reference to FIGS. 28A and 29B.

Figure 38A:
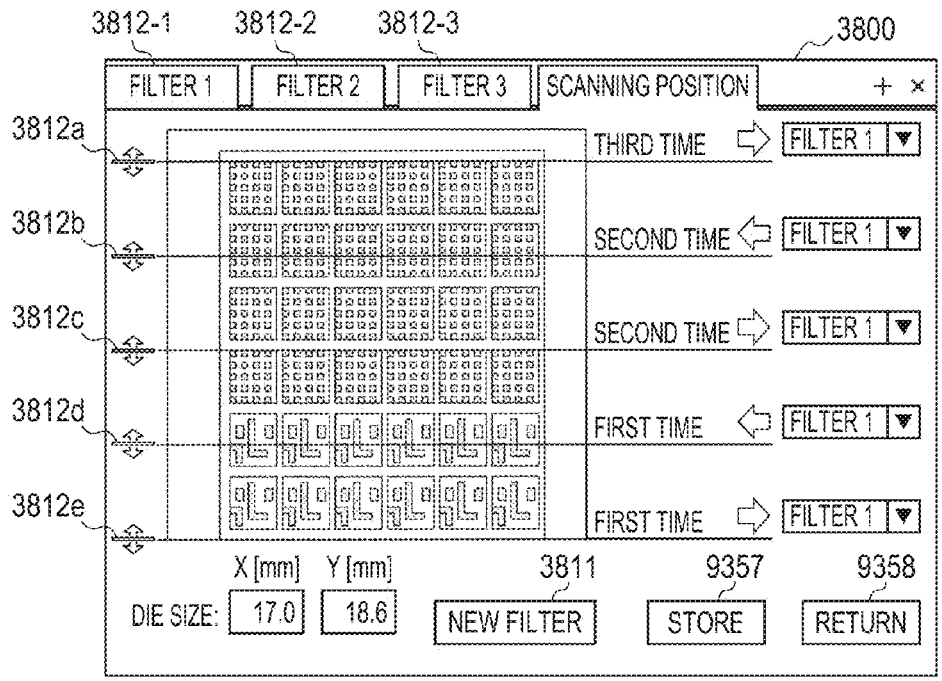
FIG. 38A is a front view of a screen image of a user interface for setting a combination of a scanning region of the spatial filter and a light blocking region and a changeover position by the inspection apparatus which includes the optical filtering device which uses the micro shutter array according to the first embodiment.
Figure 38B:
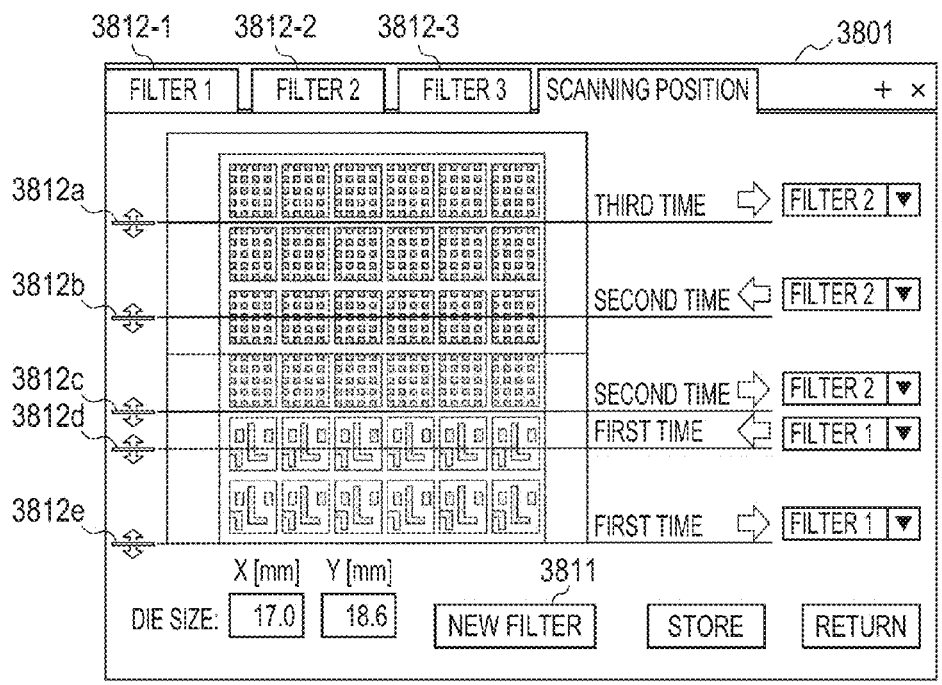
FIG. 38B is a front view of a screen image illustrating a state in which the position of a notch side end of a scanning region in each scanning cycle is moved in an X direction in conformity with a die region on the user interface for setting a combination of a scanning region of the spatial filter and a light blocking region and a changeover position by the inspection apparatus which includes the optical filtering device which uses the micro shutter array according to the first embodiment.

FIGS. 38A and 38B show an embodiment of a user interface screen image (GUI) 3800 for setting a scanning position and a combination of the scanning position and a light blocking region. Depending upon the wafer (substrate) 100 fabricated actually, patterns of the same shape formed in a die are formed like a belt. With such a wafer (substrate) 100 as just described, defect detection of a higher sensitivity can be achieved by the present modification.

FIG. 38A indicates a die pattern and a scanning region in each scanning cycle in the X direction through the user interface screen image (GUI) 3800. The user would move scanning position knobs 3812a to 3812e upwardly or downwardly to set a position of a notch side end of a scanning region in each scanning cycle in the X direction in conformity with a die region. It is to be noted that, when any of the scanning position knobs 3812a to 3812e is moved upwardly or downwardly, also a different knob moves such that the width of the scanning region for each scanning cycle has an upper limit at a value set in advance (determined taking the sensor size and so forth when the line sensor is projected on a sample through the inspection optical system into consideration).

Although FIG. 38B illustrates an example wherein the knob 3812c is moved, in this instance, also the position of the knobs 2812a and 2812b moves together with the movement of the knob 3812c. Thereafter, a light blocking state in each scanning cycle is selected. The light blocking state is set in advance using the user interface 3700 described hereinabove with reference to FIGS. 37A and 37B. It is to be noted that, if it is intended to increase a light blocking state, a new filter button 3811 is depressed. As a result, "filter" tabs 3812-1, 3812-2 and 3212-3 increase in the window. As setting of an increased light blocking region, a newly added tab is selected so that the interface of FIG. 37B is displayed and an increased light blocking region is set in the interface.

Now, a modification to the usage of the apparatus by the present embodiment is described.

Figure 39:
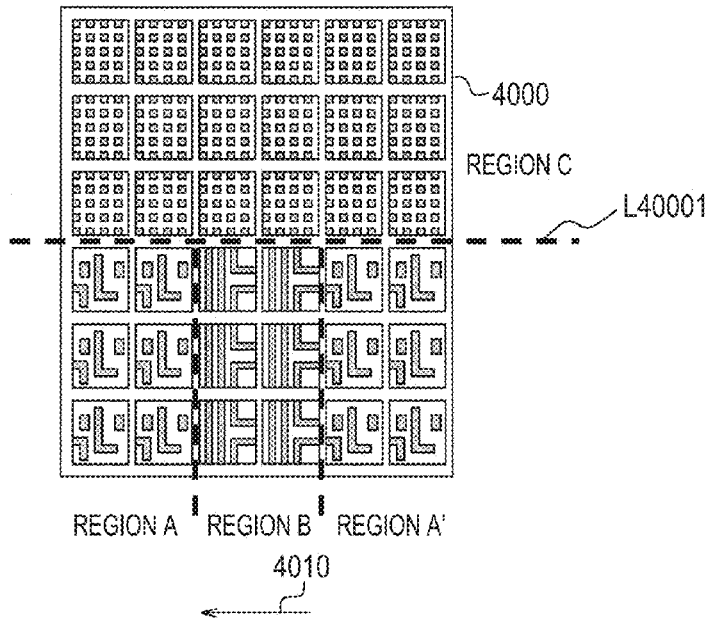
FIG. 39 shows an example of a die pattern and is a plan view of a die pattern in which a region is divided for each pattern shape.

FIG. 39 is an image view of arrangement of a certain die 4000 of a semiconductor wafer 100 (substrate).

In each of a region A and another region A', a further region B and a still further region C, substantially similar patterns are formed repetitively, and the regions A, A' and B and the region C are divided by a line L4001 extending along a scanning direction 4010. In the regions A, A' and B, comparatively large patterns such as a peripheral circuit or a logic pattern are formed, and in the region C, fine repetitive patterns of a memory or the like are formed. In the present embodiment, an example wherein the region of the die 4000 is divided and a light blocking pattern suitable for a shape of a diffracted light pattern on the Fourier transform plane of the objective lens 31 from each divisional region is set to detect a defect in a high sensitivity is described.

Figure 40:
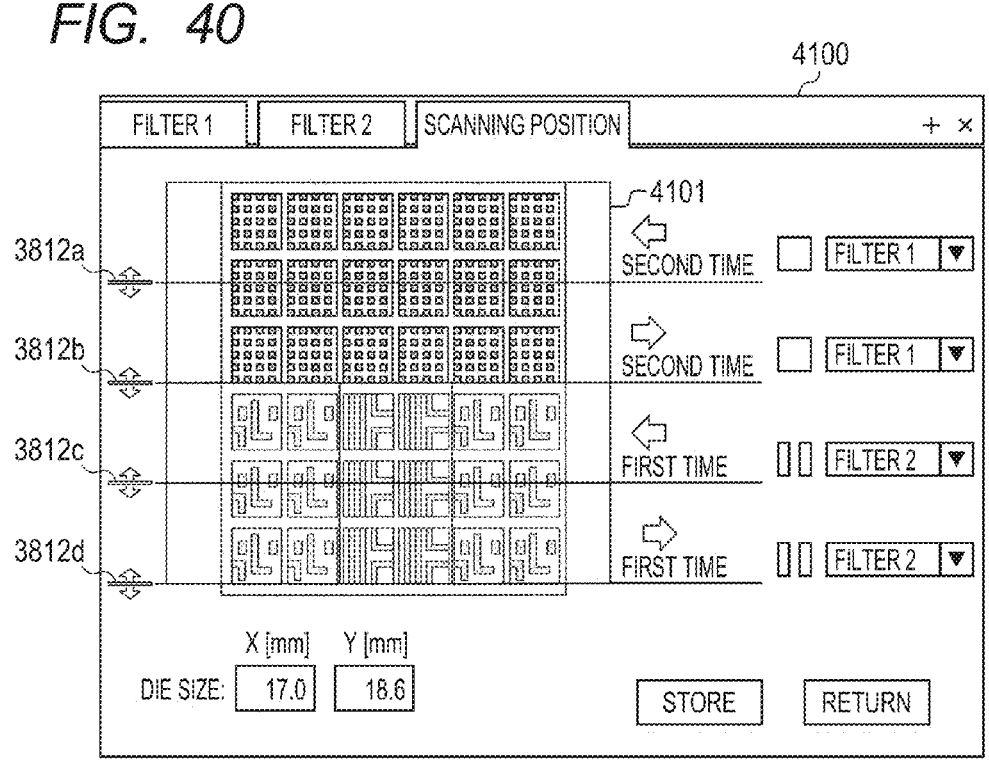
FIG. 40 is a front view of a screen image of a user interface for setting a combination of a scanning region and a light blocking region and a changeover position for carrying out a modification to a setting flow for setting a spatial filter by the inspection apparatus which includes the optical filtering device which uses the micro shutter array according to the first embodiment.

FIG. 40 shows an embodiment of a user interface screen image (GUI) 4100 for setting a scanning position and a combination of a scanning position and a light blocking region. The basic configuration of the GUI screen image 4100 is similar to that described hereinabove with reference to FIG. 38.

On this GUI screen image 4100, a die pattern and a scanning region for each scanning cycle are shown. The user would move any of scanning position knobs 3812a to 3812d upwardly or downwardly to set the position of a notch side end of the scanning region for each scanning cycle in conformity with the die 4101. It is to be noted that, when any of the knobs 3812a to 3812d is moved upwardly or downwardly, also a different knob moves such that the width of the scanning region for each scanning cycle has an upper limit at a value set in advance (determined taking the sensor size and so forth when the line sensor is projected on a sample through the inspection optical system into consideration). Here, 3812b is adjusted such that it is substantially in register with the line L4001 which divides the regions A, A' and B and the region C described hereinabove with reference to FIG. 40 from each other. Then, a filter tab 4111 or 4112 is clicked to select a filter to be used upon scanning. The example shown in FIG. 40 indicates an example wherein the filter 1 is selected so as to be used upon scanning of the region C and the filter 2 is selected so as to be used upon scanning of the regions A, A' and B.

Then, the user would select a light blocking state in each scanning cycle. The light blocking state is set in advance using the user interface screen image (GUI) 3700 described hereinabove with reference to FIG. 37. Here, when the filter 2 is set, a diffracted light pattern in the region A/A' and the region B is measured, and a light blocking region is set to each of the regions A, A' and B. Then, an exclusive OR of the set light blocking regions or the like is used to set a light blocking region for the entire pattern.

Figure 41:
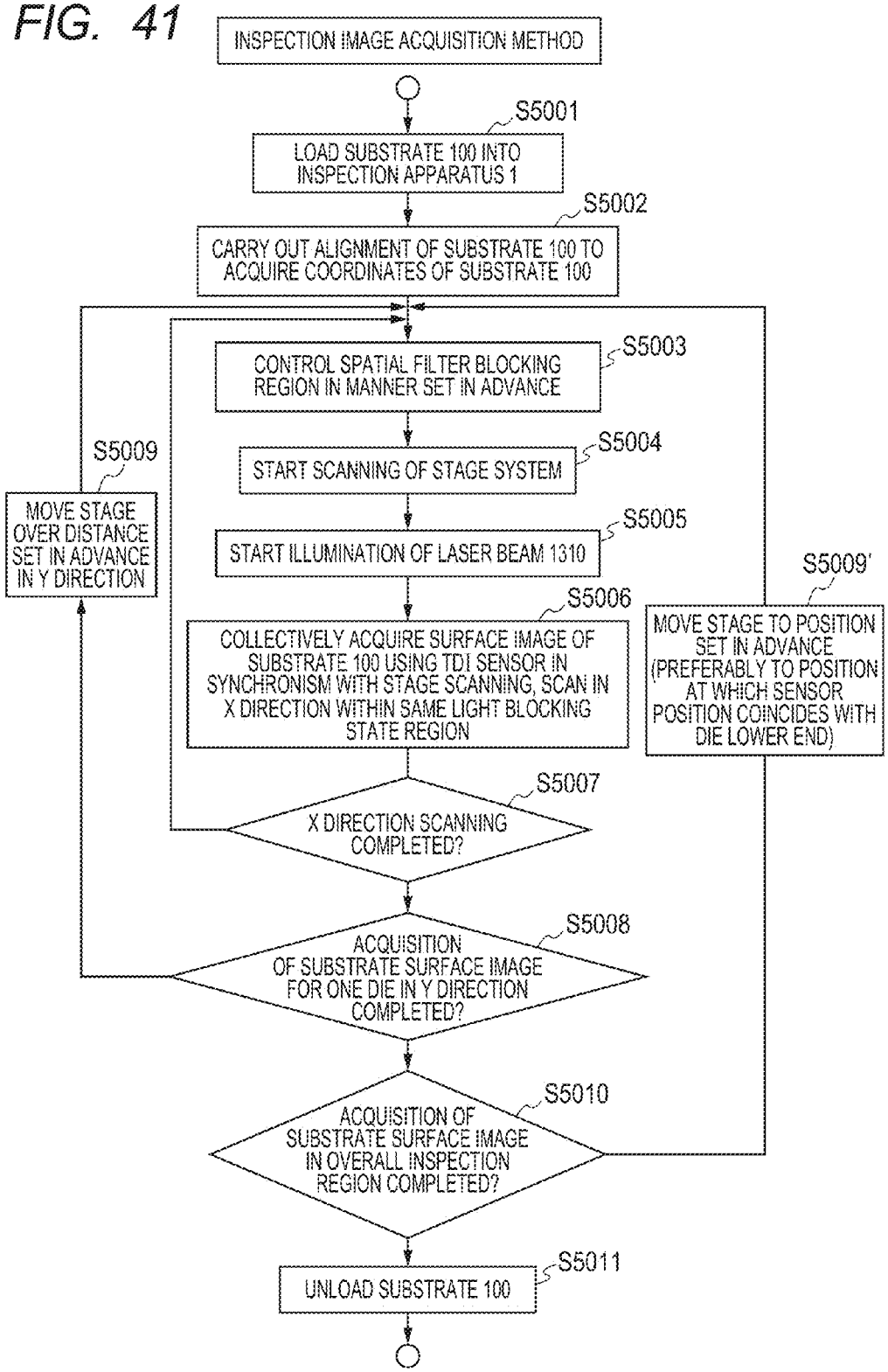
FIG. 41 is a flow chart illustrating a flow of processing for acquiring an inspection image by the inspection apparatus which includes the optical filtering device which uses the micro shutter array according to the first embodiment.

FIG. 41 illustrates a modification to the operation flow when the linear region 199 on the surface of the inspection object substrate (substrate) 100 is illuminated by the sheet beam 198 and the optical sensor (TDI sensor) 35 is used to detect an inspection image of the surface of the substrate 100.

First, a substrate 100 is loaded into the inspection apparatus 1 and fixed by the polarizing filter 34 (S5001). Then, the alignment marks 108 on the substrate 100 are used to carry out wafer alignment, and the offset 2101 and the inclination 2102 between coordinates on the substrate 100 and coordinates of the substrate scanning system are measured (S5002). If the inclination 2102 is greater than an angular threshold value 1309 set in advance, then the θ stage 25 is rotated by the inclination 2102 in the reverse direction so that the inclination reduces to almost zero. Thereafter, the alignment of the substrate is carried out again, and the offset 2101 between the coordinates on the substrate 100 and the coordinates of the substrate scanning system is measured again.

Thereafter, the optical filtering device 2000 is controlled to block a region set in advance against light (S5003). Then, the X stage 21 is scanned (S5004). The X stage 21 is moved at a substantially uniform speed while a sheet beam 1310 is irradiated upon the wafer. The shutters 13 of the laser light source 11 are opened within a range within which the irradiation region of the sheet beam remains on the wafer to carry out sheet beam illumination (S5005).

The TDI sensor is rendered operative in synchronism with the scanning of the X stage 21 to collectively acquire a surface image of the substrate 100 (S5006). After one cycle of scanning of the X stage 21 is completed, the stage is moved in the Y direction by a distance set in advance (S5008). At this time, since the light blocking region of the spatial filter can be set for every one scanning cycle, when an operation for a different light blocking pattern is to be carried out subsequently, the optical filtering device 2000 is controlled so that the region set in advance is blocked against light (S5003).

After the acquisition of the substrate surface image for one die in the Y direction is completed, the stage is moved to the proximity of a position at which the sensor position is in register with a lower end of the next die in the Y direction (S5009'). Then, the scanning of the X stage 21 is carried out repetitively. Here, if the acquisition of the substrate surface image of the overall measurement region on the substrate designated in advance is completed (S5010), then the substrate 100 is unloaded (S5011), thereby completing the operation as the inspection apparatus.

Embodiment 2

Now, a second embodiment wherein an optical filtering device which uses a micro shutter array according to the present invention is used is applied to a dark-field inspection apparatus for inspecting a defect of a semiconductor wafer (substrate) is described with reference to FIG. 42.

Figure 42:
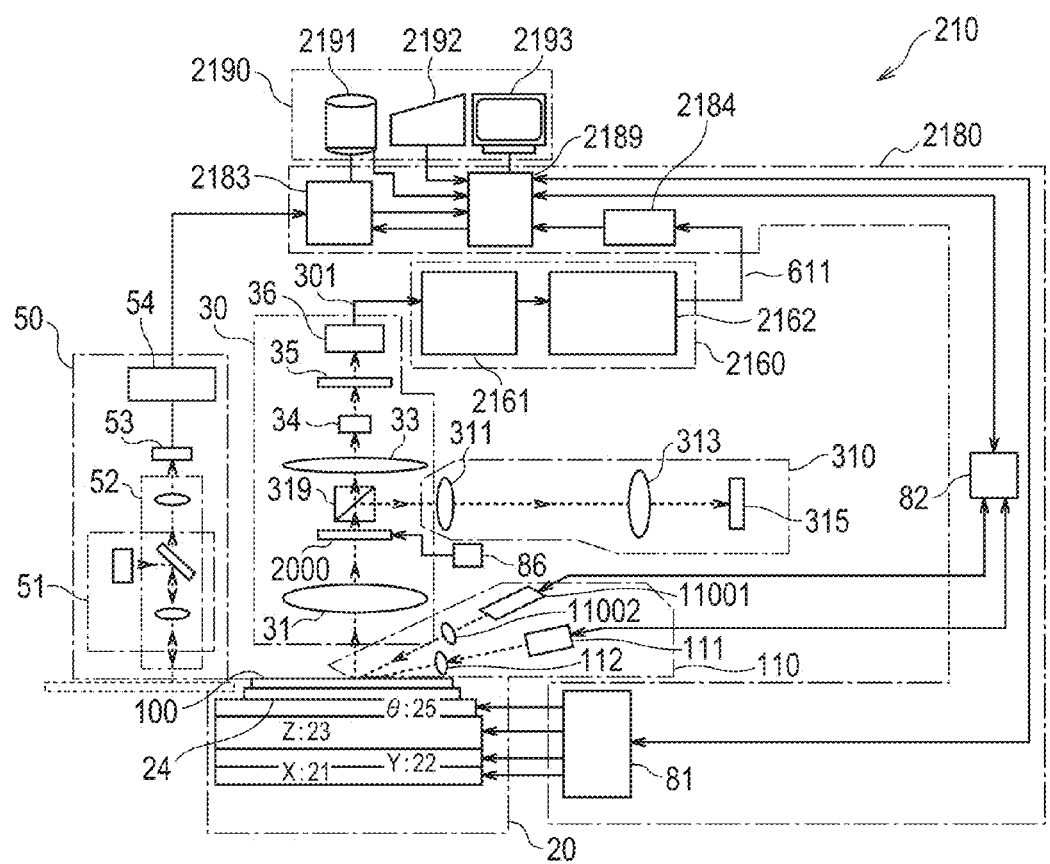
FIG. 42 is a block diagram showing a general configuration of an inspection apparatus which includes an optical filtering device which uses a micro shutter array according to a second embodiment and inspects a wafer on which a pattern is formed in a dark field.

FIG. 42 is a block diagram of an inspection apparatus 210. Like components to those of the inspection apparatus according to the first embodiment shown in FIG. 21A are denoted by like reference numerals.

The second embodiment is different from the first embodiment in that an illumination optical system 110 includes a laser light source 111 and a lens 112 for beam shaping, and a laser light source 11001 and a lens 11002 for beam shaping, and light emitted from the laser light source 111 is suitably shaped by the lens 112 or light emitted from the laser light source 11001 is suitably shaped by the lens 11002, to illuminate the inspection object substrate 100.

An image processing system 2160 includes an inter-adjacent die image positional displacement information calculation unit 2161 and a data processing unit 2162 for carrying out a defect decision and detection process using an inter-die difference image. The inter-adjacent die image positional displacement information calculation unit 2161 and the data processing unit 2162 individually include a memory having a capacity sufficient to store image data therein.

A controlling and processing system 2180 at least includes a transport system controlling unit 81 for controlling the substrate transport system 20, an illumination light source controlling unit 82, and a sensor controlling unit 2183 for acquiring an image from a detection signal from the first detection optical system 30. The controlling and processing system 2180 further includes a defect information processing unit 2184 for carrying out a classification process of defect information 611 outputted from the image processing system 2160, and a control unit 2189 for controlling the entire controlling and processing system 2180. FIG. 42 shows also a power supply unit 86 including a control circuit for the optical filtering device 2000.

An interface system 2190 at least includes a data accumulation section 2191 for accumulating defect information processed by and outputted from the controlling and processing system 2180, and an inputting section 2192 for carrying out inspection condition setting or controlling processing information inputting. The interface system 2190 further includes a display section 2193 for displaying defect information or displaying controlling processing information.

Figure 43:
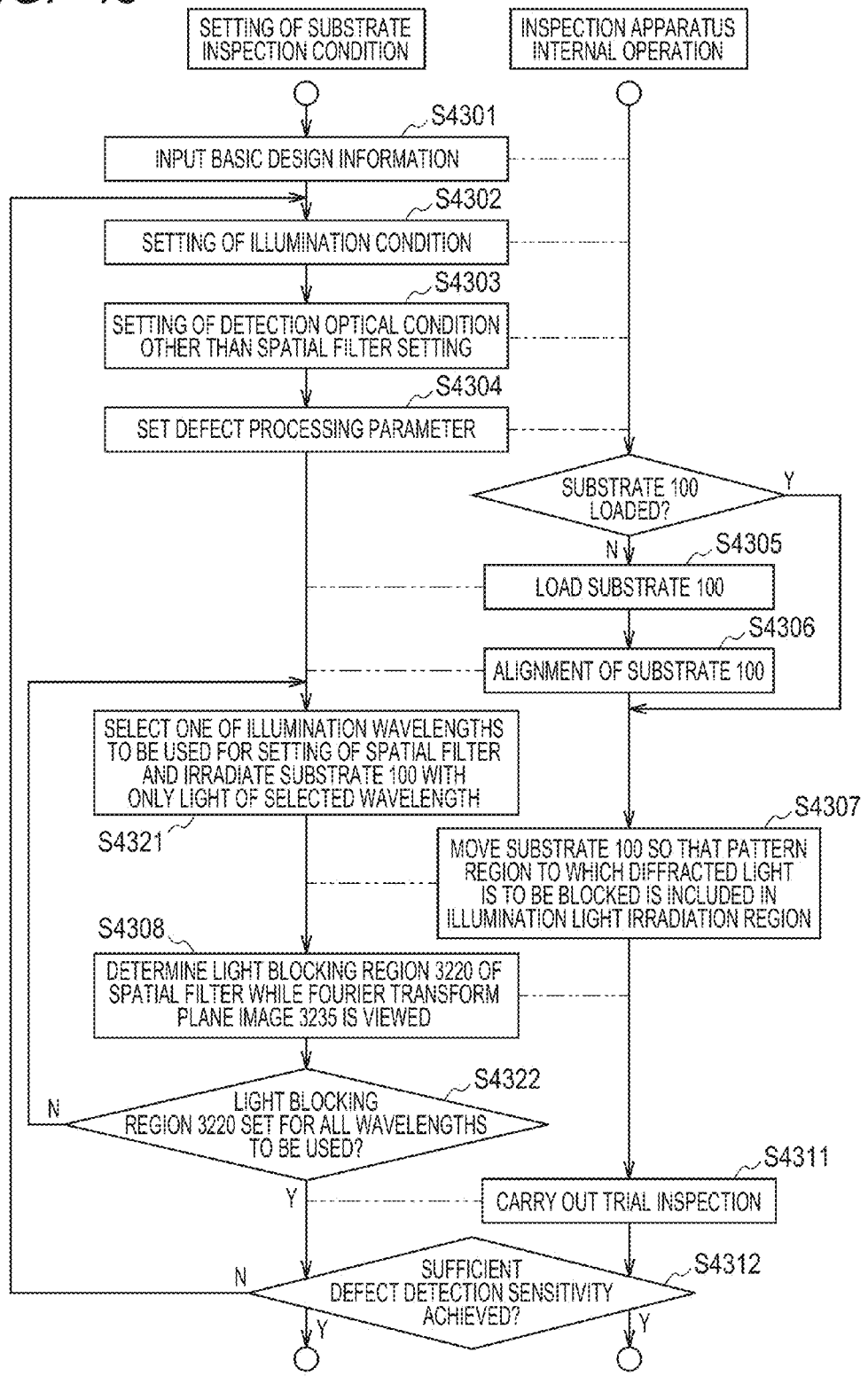
FIG. 43 is a flow chart illustrating a flow of processing for setting substrate inspection conditions of the inspection apparatus which includes the optical filtering device according to the second embodiment.

Now, a setting flow of substrate inspection conditions using the inspection apparatus according to the embodiment 2 is shown in FIG. 43.

Operation of the inspection apparatus according to the embodiment 2 is same as the operation described hereinabove with reference to FIG. 23 in connection with the embodiment 1 until a substrate 100 is loaded into the apparatus and alignment of the substrate 100 is carried out (S4306).

As an illumination light source, one wavelength of the illumination optical system 110 or 11001 is selected and irradiated upon the substrate 100 (S4321). The X stage 21 or the Y stage 22 is driven by the transport system controlling unit 81 to move the substrate 100 so that a region including a pattern to which diffracted light is to be removed by the optical filtering device 2000 from among patterns on the substrate 100 may be included in the region in which the illumination light is irradiated (S4307).

Then, while the Fourier transform plane image 3235 (FIG. 28A) is viewed using the pupil plane observation system 310, the light blocking region 3220 (FIG. 28B) of the optical filtering device 2000 is determined (S4308). Here, it is to be noted that the light blocking region 3220 is set as a light blocking region for inspection obtained by adding a light blocking region determined in advance by illumination of a different waveform on the substrate 100 and the light blocking region 3220 determined at the preceding stage.

Thereafter, the procedure at S4321, S4307 and S4308 is repeated until setting of a light blocking region 3220 is set for all wavelengths of illumination light to be sequentially used in the inspection.

The substrate 100 is trial-inspected using the inspection conditions set by the procedure described above (S4311), and the substrate inspection condition setting is ended if a sufficient defect detection sensitivity can be achieved (S4312). If the defect detection sensitivity is insufficient, then the conditions set through the procedure from the setting of illumination conditions (S4302) are modified until a sufficient defect detection sensitivity can be achieved.

Figure 44A:
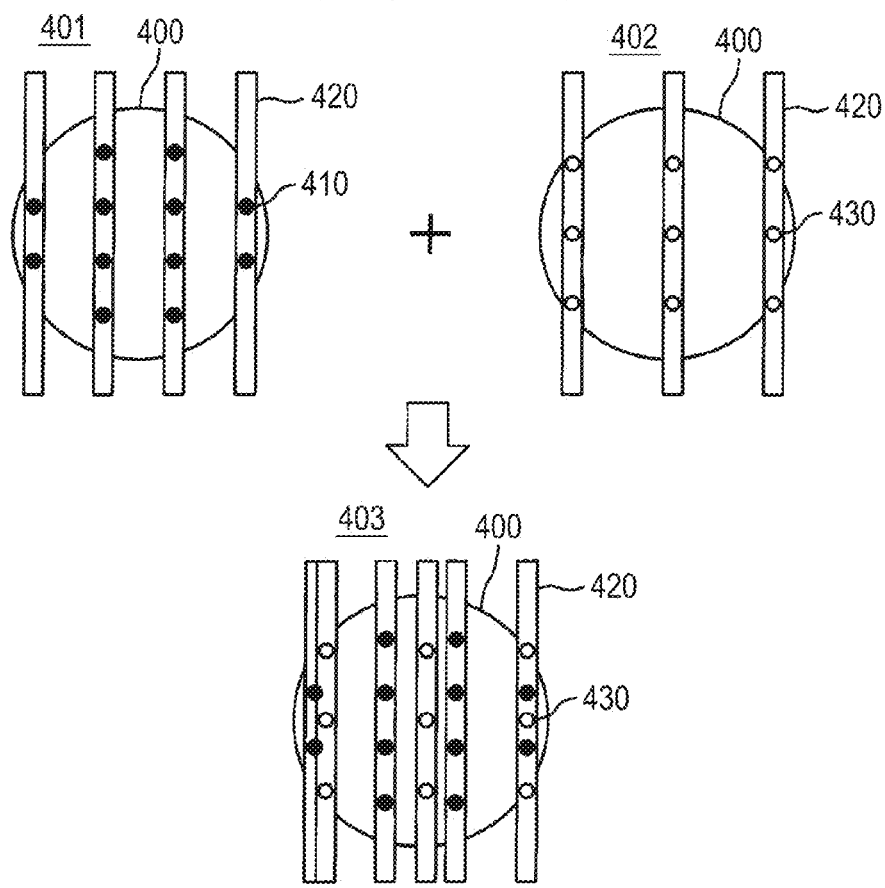
FIG. 44A is a plan view of the Fourier transform plane illustrating a distribution of bright points on the Fourier transform plane by diffracted light from repetitive patterns on a substrate and includes a FIG. 401 illustrating a positional relationship between a distribution of bright points from first repetitive patterns and linear light blocking patterns, a FIG. 402 illustrating a positional relationship between a distribution of brightness points from second repetitive patterns and linear light blocking patterns, and a FIG. 403 wherein they are overlapped with each other.

Now, an embodiment wherein diffracted light from a pattern formed on the substrate 100 is blocked using the optical filtering device 2000 installed on the Fourier transform plane of the objective lens 31 is described with reference to FIGS. 44A and 44B.

On the substrate 100 of an object of inspection, usually various repetitive patterns are formed at pitches different from each other. In 401 of FIG. 44A, arrangement of bright points 410 which are generated by scattered light from the first repetitive patterns formed on the substrate 100 and generated in a visual field 400 of the detection optical system 30 on the Fourier transform plane of the objective lens 31 and light blocking patterns 420 conventionally used to block light to the bright points 410 is illustrated. Meanwhile, in 402 of FIG. 44A, arrangement of bright points 430 which are generated by scattered light from the second repetitive patterns formed on the substrate 100 and light blocking patterns 420 conventionally used to block light to the bright points 410 is illustrated. Where the substrate 100 is inspected over the overall area, when the first repetitive pattern region is inspected, the bright points 410 are generated in the visual field 400 of the detection optical system 30 on the Fourier transform plane of the objective lens 31, and when the second repetitive pattern region is inspected, the bright points 430 are generated. Therefore, a large number of light blocking patterns 420 must be disposed in accordance with the bright points 410 and the bright points 430 and the light blocking region in the field of view must be made great as illustrated in 403 of FIG. 44A. As a result, the detection accuracy is deteriorated.

Figure 44B:
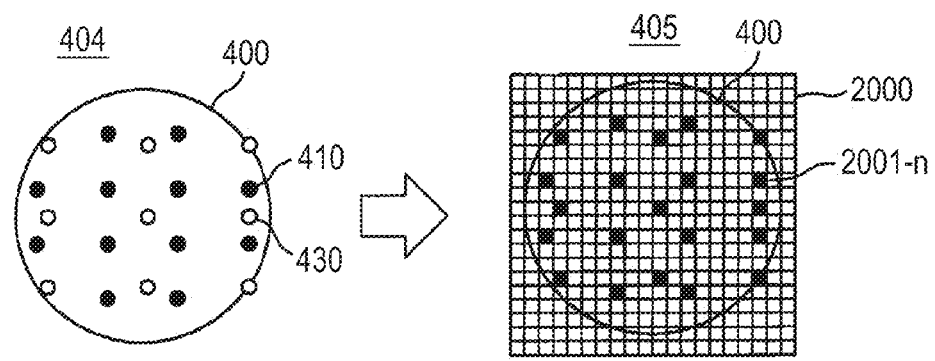
FIG. 44B is a plan view 404 of the Fourier transform plane in which distributions of brightness points on the Fourier transform plane by refracted light from the first and second repetitive patterns on the substrate are illustrated in an overlapping relationship with each other and a plan view of the micro shutter array showing a shape of a light blocking pattern formed in conformity with the distribution of the brightness points on the micro shutter array.

On the other hand, where the optical filtering device 2000 according to the present invention is used, if such bright points 410 and 430 as illustrated in 404 of FIG. 44B are generated in the visual field 400 on the Fourier transform plane of the objective lens 31 by scattered light from the patterns formed on the substrate 100, such a light blocking pattern as indicated by 2001-*n* in 405 of FIG. 44B is generated on the optical filtering device 2000 disposed on the Fourier transform plane of the objective lens 31. This makes it possible to allow light to be blocked only at places at which the bright points 410 and 430 are generated and makes it possible to carry out detection without decreasing the amount of light to enter the optical sensor 35. As a result, defects can be detected with a high sensitivity in comparison with that in an alternative case in which intense light from the bright points 410 and 430 is blocked using a conventional linear filter 420.

Figure 45:
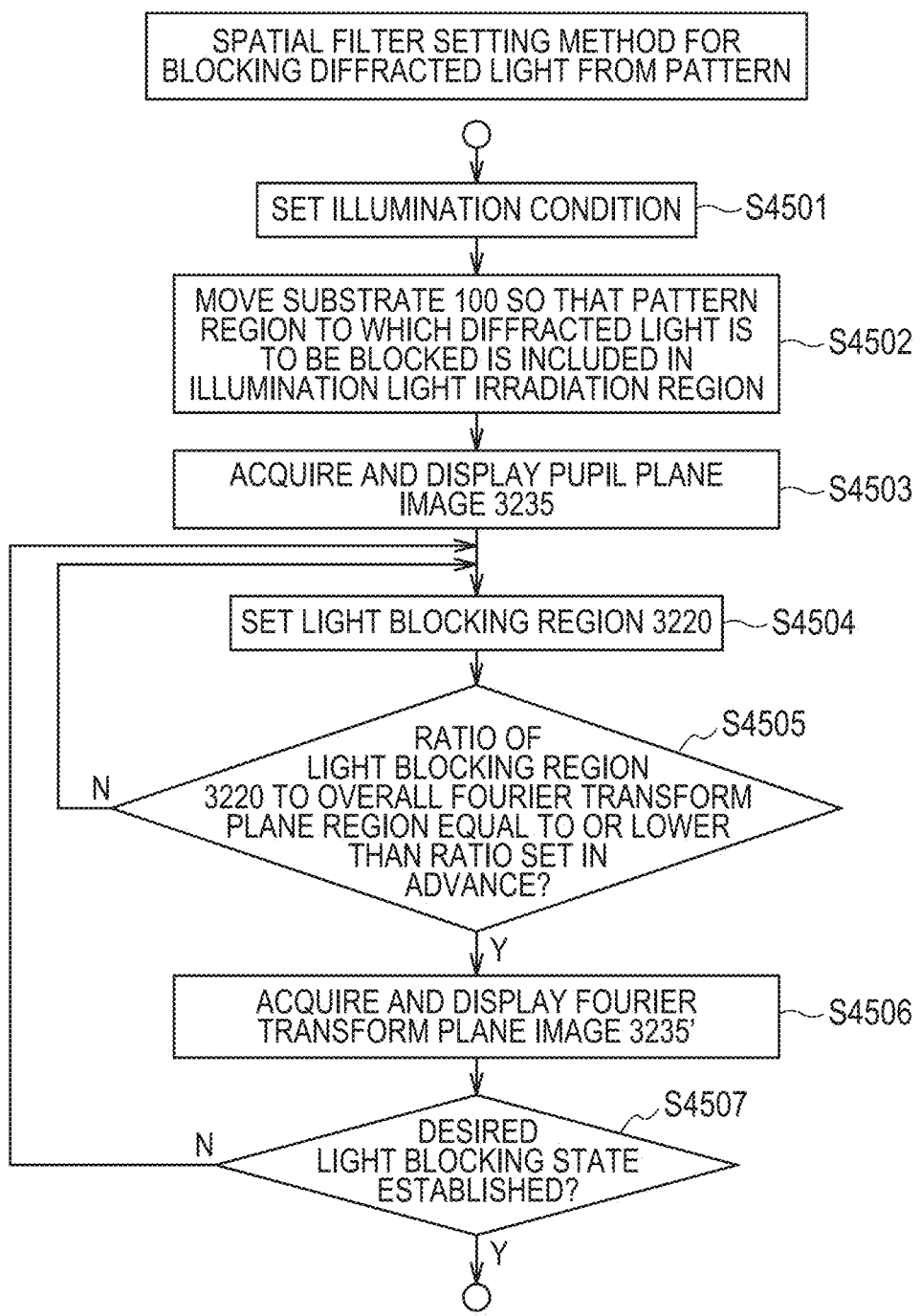
FIG. 45 is a flow chart illustrating a flow of processing for setting substrate inspection conditions of the inspection apparatus according to the second embodiment.

Now, a modification to the embodiment wherein diffracted light from the patterns formed on the substrate 100 is blocked using the optical filtering device 2000 installed on the pupil plane of the objective lens 31 is described with reference to FIG. 45.

First, illumination conditions to be used for inspection of the substrate 100 are set (S4501). Then, the stage system is rendered operative to move the substrate 100 so that a pattern region to which diffracted light is to be blocked may be included in the illumination light irradiation region (S4502). A pupil plane image 3235 including diffracted light from the pattern is acquired (S4503). A light blocking region is set based on the idea to block intense diffracted light (S4504). Here, it is confirmed whether or not light to the Fourier transform plane of the objective lens 31 is blocked exceeding a ratio set in advance (S4505). This is because, if the light blocking region is too great, then the resolution of the inspection image is prone to drop and the defect detection sensitivity accordingly drops. Thereafter, the pupil plane distribution is actually measured by the pupil plane observation system 310 in a state in which a spatial filter by the optical filtering device 2000 is set (S4506). Then, it is confirmed that the region into which intense diffracted light has been entered is blocked against light (S4507). The setting of a light blocking state using the optical filtering device 2000 is completed thereby.

Embodiment 3

Figure 46:
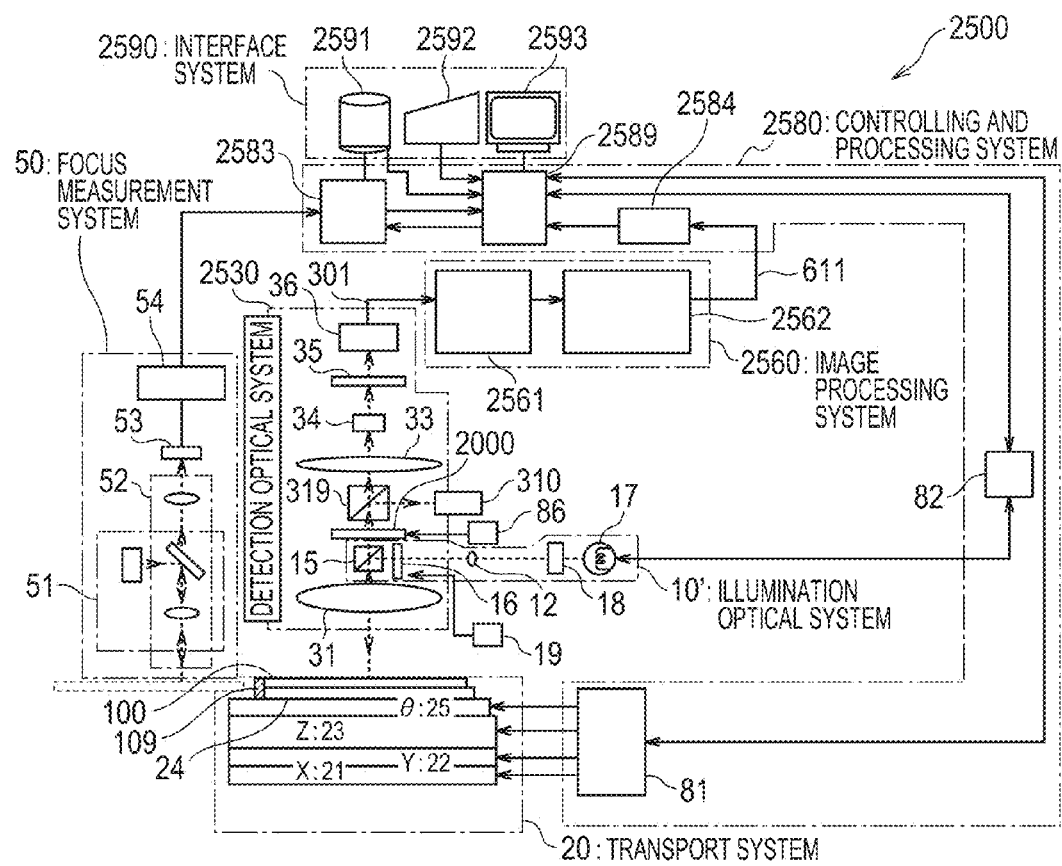
FIG. 46 is a block diagram showing a general configuration of a substrate inspection apparatus according to a third embodiment.

A configuration of a bright-field inspection apparatus which uses a lamp as a light source and which is a third embodiment of the present invention is described with reference to FIG. 46.

The third embodiment is changed in configuration of the illumination optical system from the first embodiment. The illumination optical system 10' includes a lamp light source 17 and a lens 12 for beam shaping, a beam splitter 15, and an illumination diaphragm 16 and a controlling apparatus 19 for the illumination diaphragm. It is to be noted that a wavelength selector 18 may be installed in an illumination light path in order to raise the sensitivity for defect detection. FIG. 46 shows an embodiment wherein the wavelength selector 18 is installed in an illumination light path. The lamp light source 17 is disposed such that an image thereof is formed at the position of the illumination diaphragm 16 through the lens 12. The position of the illumination diaphragm 16 is provided on the Fourier transform plane of the objective lens through the beam splitter 15. By this arrangement, the illumination optical system 10' forms a Kohler illumination optical system. By suitably controlling the magnitude and the position of the light blocking region of the illumination diaphragm 16, the illumination conditions such as the illumination spread angle and the lighting elevation can be changed.

A detection optical system 2530 includes an objective lens 31, an optical filtering device 2000, an imaging lens 33, an optical sensor 35, and an A/D conversion unit 36. If a sensor of the integration type (TDI (Time Delay Integration) sensor) is used as the optical sensor 35, then inspection can be carried out at a high speed.

Further, a polarizing filter 34 may be provided between the imaging lens 33 and the optical sensor 35. In FIG. 46, a block diagram including the polarizing filter 34 is shown. Although the configuration of the pupil plane observation system 310 is omitted, the pupil plane observation system 310 includes lenses 311 and 313 and an area sensor 315 so that a light intensity distribution on the Fourier transform plane of the object lens can be observed similarly as in the description given hereinabove with reference to FIGS. 21A and 42.

Reference numeral 319 denotes a beam splitter configured from a half mirror. The beam splitter 319 transmits half of light condensed by the objective lens 31 and transmitted through the optical filtering device 2000 from within scattered light from the substrate 100 illuminated by the illumination optical system 10 and introduces the half of the light toward the imaging lens 33. Meanwhile, the half mirror 319 reflects and introduces the remaining half of the light toward the pupil plane observation system 310.

An image processing system 2560 includes an inter-adjacent die image positional displacement information calculation unit 2561, and a data processing unit 2562 for carrying out a defect decision and detection process using an inter-die difference image. The inter-adjacent die image positional displacement information calculation unit 2561 and the data processing unit 2562 individually include a memory having a capacity sufficient to store image data.

A controlling and processing system 2580 at least includes a transport system controlling unit 81 for controlling the substrate transport system 20, an illumination light source controlling unit 82, and a sensor controlling unit 2583 for acquiring information from a detection signal from the detection optical system 2530. The controlling and processing system 2580 further includes a defect information processing unit 2584 for carrying out a classification process of defect information 611 outputted from the image processing system 2560, and a control unit 2589 for controlling the entire controlling and processing system 2580. FIG. 46 illustrates also a power supply unit 86 including a control circuit for the optical filtering device 2000. Although the power supply unit 86 is connected to the control unit 2589, illustration thereof is omitted in FIG. 46.

An interface system 2590 at least includes a data accumulation section 2591 for accumulating defect information processed by and outputted from the controlling and processing system 2580, and an inputting section 2592 for carrying out inspection condition setting and controlling processing information inputting. The interface system 2590 further includes a display section 2593 for displaying defect information and displaying controlling processing information.

In the present embodiment, the diffracted light distribution on the Fourier transform plane of the objective lens 31 has a spread greater than that in the case of the embodiment 2. This is because the lamp illumination light source has a waveform distribution of illumination light and, since the lamp illumination light source is low in luminance in comparison with the laser light source, it is frequently necessary to assure a high illumination σ to use a greater illumination light intensity. Therefore, the combination of linear filters at equal distances as conventionally known cannot achieve a sufficient performance to block unnecessary diffracted light. However, with the two-dimensional filter system 32 which uses the optical filtering device 2000 according to the present invention, since light to an arbitrary region can be blocked, even if the diffracted light distribution expands, light blocking is possible.

Figure 47:
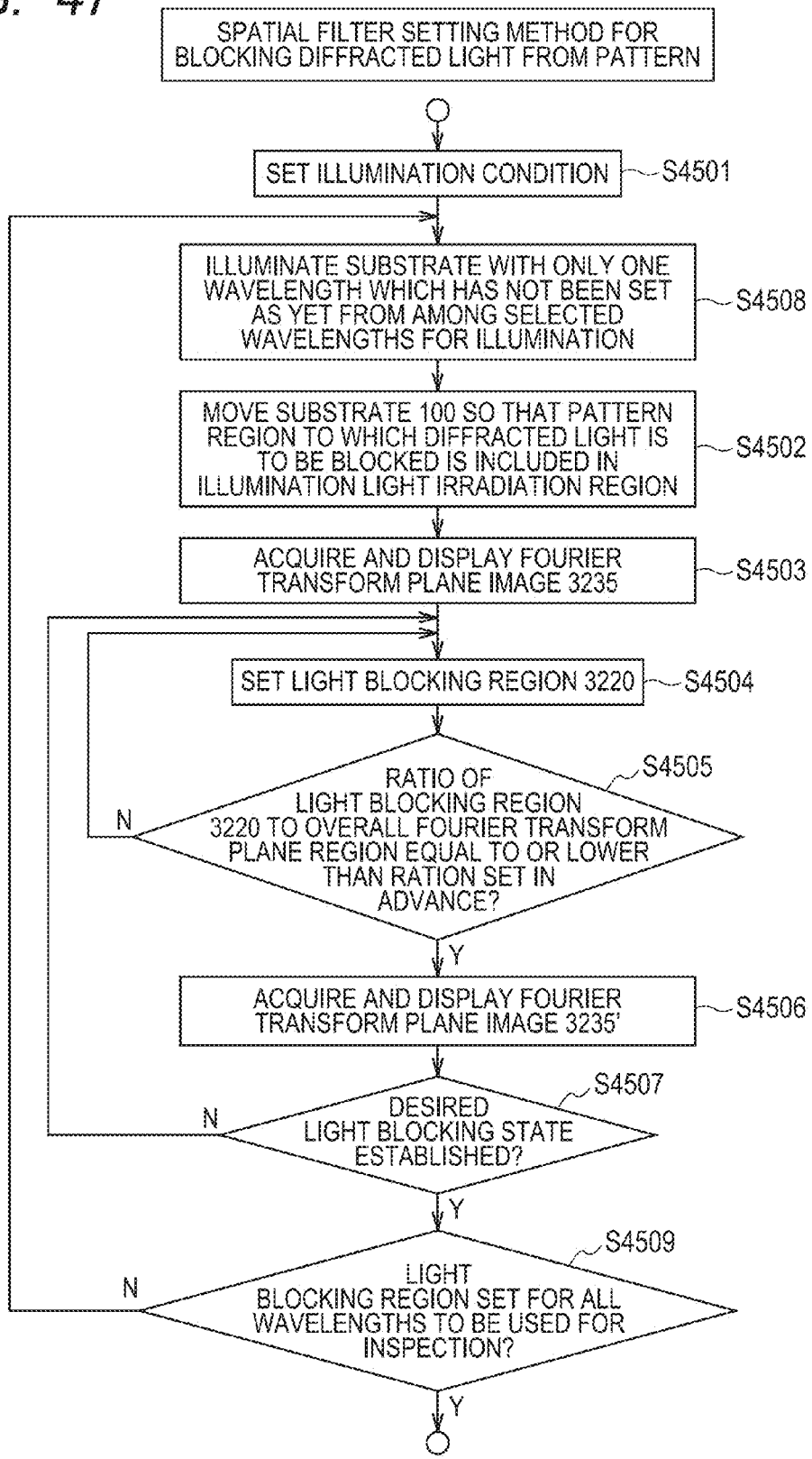
FIG. 47 is a flow chart illustrating a flow of processing for setting a light blocking region of a spatial filter according to the third embodiment.

Now, an embodiment wherein diffracted light from a pattern formed in the proximity of the surface of a wafer is blocked using a spatial filter installed on the pupil plane is described with reference to FIG. 47.

First, illumination conditions to be used for wafer inspection are set (S4501). Then, one wavelength for which a light blocking pattern is not determined from among wavelengths of illumination light to be used in the section is selected, and the substrate 100 is illuminated only by the selected wavelength (S4508). The stage system is rendered operative to move the substrate 100 so that a pattern region to which diffracted light is to be blocked may be included in the illumination light irradiation region (S4502). A pupil plane image 3235 including diffracted light from the pattern is acquired (S4503). A light blocking region is set based on the idea to block intense refracted light (S4504). Here, it is confirmed whether or not light to the Fourier transform plane of the objective lens 31 is blocked exceeding a ratio set in advance (S4505). This is because, if the light blocking region is too great, then the resolution of the inspection image is prone to drop and the defect detection sensitivity accordingly drops. Thereafter, the pupil plane distribution is actually measured in a state in which a spatial filter is set (S4506), and it is confirmed that a region into which intense refracted light has entered is blocked against light (S4507). The procedure at S4508 and S4502 to S4507 is repetitively carried out for light of all wavelengths to be used in the inspection (S4509). If a light blocking region is set for all wavelengths, then the present procedure is completed.

Embodiment 4

Figure 48:
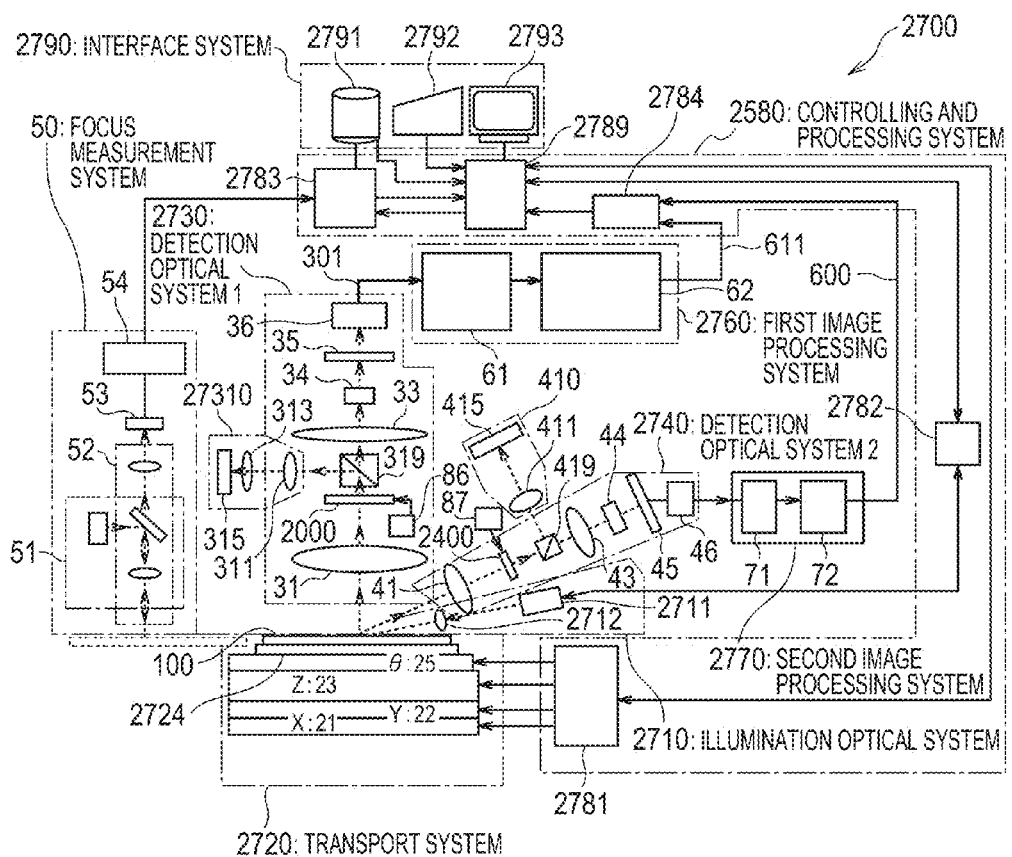
FIG. 48 is a block diagram showing a general configuration of a substrate inspection apparatus having an oblique detection optical system according to a fourth embodiment.

Now, a fourth embodiment wherein an optical filtering device in which a micro shutter array according to the present invention is used is applied to a dark-field inspection apparatus is described with reference to FIG. 48.

The inspection apparatus 2700 includes an illumination optical system 2710, a substrate transport system 2720, an upper detection optical system 2730, a first Fourier transport plane observation system 27310, an oblique detection optical system 2740, and a second Fourier transform plane observation system 410. The inspection apparatus 2700 further includes a focus measurement system 50, a first image processing system 2760, a second image processing system 2770, a controlling and processing system 2780, and an interface system 2790.

The illumination optical system 2710 includes a laser light source 2711 and a lens 2712 for beam shaping, and suitably shapes light emitted from the laser light source 2711 by the lens 2712 and illuminates an inspection object substrate 100. Like elements to those of the dark-field inspection apparatus 1 shown in FIG. 21 in the embodiment 1 are denoted by like reference numerals.

The substrate transport system 2720 includes an X stage 21, a Y stage 22, a Z stage 23, a substrate chuck 24, and a θ stage 25.

The detection optical system 1: 2730 which is an upper detection optical system includes an objective lens 31, an optical filtering device 2000, an imaging lens 33, an optical sensor 35, and an A/D conversion unit 36. Further, a polarizing filter 34 may be interposed between the imaging lens 33 and the optical sensor 35. In FIG. 48, a configuration which includes the polarizing filter 34 is shown.

While the optical filtering device 2000 is installed on the Fourier transform plane of the objective lens 31, the first Fourier transform plane observation system 27310 is installed such that a light intensity distribution and a light blocking state by the optical filtering device 2000 on the Fourier transform plane can be observed. The first Fourier transform plane observation system 27310 at least includes an optical element 319 for splitting light, lenses 311 and 313, and an area sensor 315.

A detection optical system 2: 2740 which is an oblique detection optical system includes, similarly to the upper detection optical system 2730, an objective lens 41, an optical filtering device 2400, an imaging lens 43, an optical sensor 45, and an A/D conversion unit 46. Further, a polarizing filter 44 may be interposed between the imaging lens 43 and the optical sensor 45. FIG. 48 shows a diagram of a configuration which includes the polarizing filter 44.

Although the optical filtering device 2400 is installed on the Fourier transform plane of the objective lens 41, the second Fourier transform plane observation system 410 is installed such that a light intensity distribution and a light blocking state by the optical filtering device 2400 on the Fourier transform plane can be observed. The second Fourier transform plane observation system 410 includes an optical element 419 for splitting light, lenses 411 and 413, and an area sensor 415.

The focus measurement system 50 includes an illumination optical system 51, a detection optical system 52, an optical sensor 53, and a focus shift calculation processing unit 54.

The first image processing system 60 includes an inter-adjacent die image positional displacement information calculation unit 61, and a data processing unit 62 which uses an inter-die difference image to carry out a defect decision and detection process.

The second image processing system 70 includes an inter-adjacent die image positional displacement information calculation unit 71, and a data processing unit 72 which uses an inter-die difference image to carry out a defect decision and detection process.

The controlling and processing system 2780 at least includes a transport system controlling unit 2781 for controlling the substrate transport system 2720, and an illumination light source controlling unit 2782. The controlling and processing system 2780 further includes a sensor controlling unit 2783 for synchronizing the detection optical system 1: 2730 which is an upper detection optical system, and the detection optical system 2: 2740 which is an oblique detection optical system with each other to acquire an image. The controlling and processing system 2780 further includes a defect information processing unit 2784 for carrying out a merge process and a classification process of defect information 600 and 611 outputted from the first image processing system 2760 and the second image processing system 2770. The controlling and processing system 2780 further includes a control unit 2789 for controlling the entire controlling and processing system 2780. In FIG. 48, also a power supply unit 86 including a control circuit for the optical filtering device 2000 and another power supply unit 87 including a control circuit for the optical filtering device 2400 are shown. (In FIG. 48, indication of the power supply unit 86 and signal lines which interconnect the power supply units 87 and the control unit 2789 is omitted for simplified illustration.)

The interface system 2790 at least includes a data accumulation section 2791 for accumulating defect information processed by and outputted from the controlling and processing system 2780. The interface system 2790 further includes an inputting section 2792 for carrying out inspection condition setting and controlling process information inputting, and a display section 2793 for displaying defect information and displaying controlling processing information.

The fourth embodiment is most different from the first embodiment in that it includes the detection optical system 2: 2740 which is an oblique detection optical system, the second Fourier transform plane observation system 410 and the second image processing system 70.

Figure 49A:
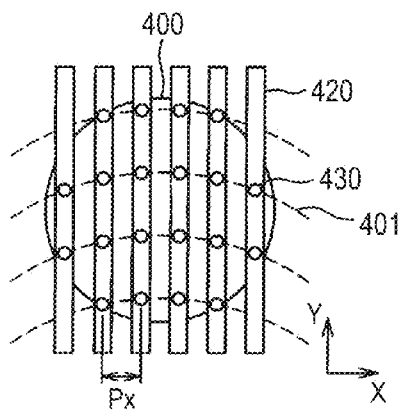
FIG. 49A is a plan view of the Fourier transform plane illustrating a state in which a distribution of bright points on the Fourier transform plane of an oblique detection system of the substrate inspection apparatus having the oblique detection optical system according to the fourth embodiment is blocked against light by a light blocking pattern elongated in a Y direction.
Figure 49B:
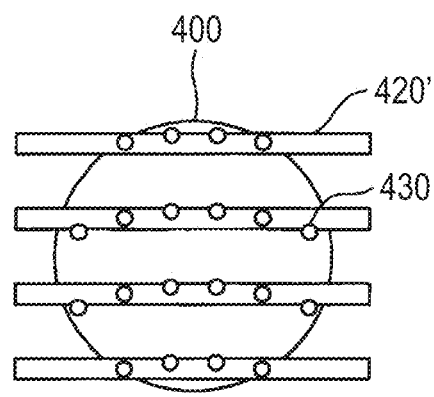
FIG. 49B is a plan view of the Fourier transform plane illustrating a state in which a distribution of bright points on the Fourier transform plane of the oblique detection system of the substrate inspection apparatus having the oblique detection optical system according to the fourth embodiment is blocked against light by a light blocking pattern elongated in an X direction.
Figure 49C:
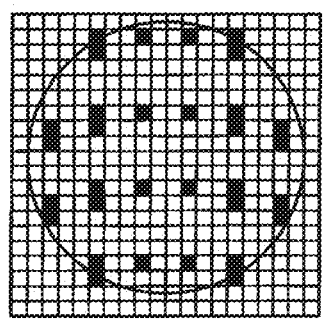
FIG. 49C is a plan view of the Fourier transform plane illustrating a state in which a distribution of bright points on the Fourier transform plane of an oblique detection system of the substrate inspection apparatus having the oblique detection optical system according to the fourth embodiment is blocked against light by a micro shutter array.

FIGS. 49A to 49C illustrate a state in which light incident to the detection optical system 2: 2740 which is an oblique detection optical system within diffracted light from the repetitive patterns formed on the substrate 100 is condensed on the Fourier transform plane.

In general semiconductor substrates and the like, repetitive patterns are frequently formed in XY directions. Therefore, a light intensity distribution on the Fourier transform plane of the detection optical system 1: 2730 which is an upper detection optical system which is installed in a direction substantially perpendicular to the surface of the substrate 100 indicates a distribution of a lattice in vertical and horizontals, and crossing points of the lattice become bright points. However, the detection optical system 2: 2740 which is an oblique detection optical system is inclined by a great amount from the perpendicular direction to the surface of the inspection object substrate 100. Therefore, as discussed also in JP-A-2000-105203 (Patent Document 4), in the light intensity distribution in the visual field 400 on the Fourier transform plane in the detection optical system 2: 2740, bright points 430 are juxtaposed, in one direction (Y direction in FIG. 49A), at lattice points on straight lines but, in a perpendicular direction to the one direction (in the X direction in FIG. 49A), at lattice points on curved lines. In this instance, if it is tried to use filters 420 to block light to the bright points 430, then it is necessary to place filters 420 which are long in the juxtaposition direction of the straight lines of the lattice as shown in FIG. 49A. Thus, where the lattice point distance $P_x$ is small, there is the possibility that the light blocking regions by the filters 420 in the aperture of the objective lens 41 may become so great that inspection is substantially disabled.

In contrast, where the lattice points on the curved lines are blocked against light by such filters 420' extending in the horizontal direction as shown in FIG. 49B, there is no problem if the curve of the curved lines 401 is not great (curvature is great) and the filters 420' extending in the horizontal direction can be used for light blocking. However, where the filters 420' do not have a sufficient width as shown in FIG. 49B, it is difficult to block all bright points against light. In contrast, with the optical filtering method in which the optical filtering device 2000 is used according to the present development, since light can be blocked only at the regions of the bright points, desired bright points can be blocked against light in a state in which the region for blocking light of the aperture of the objective lens 41 is small.

Embodiment 5

Figure 50:
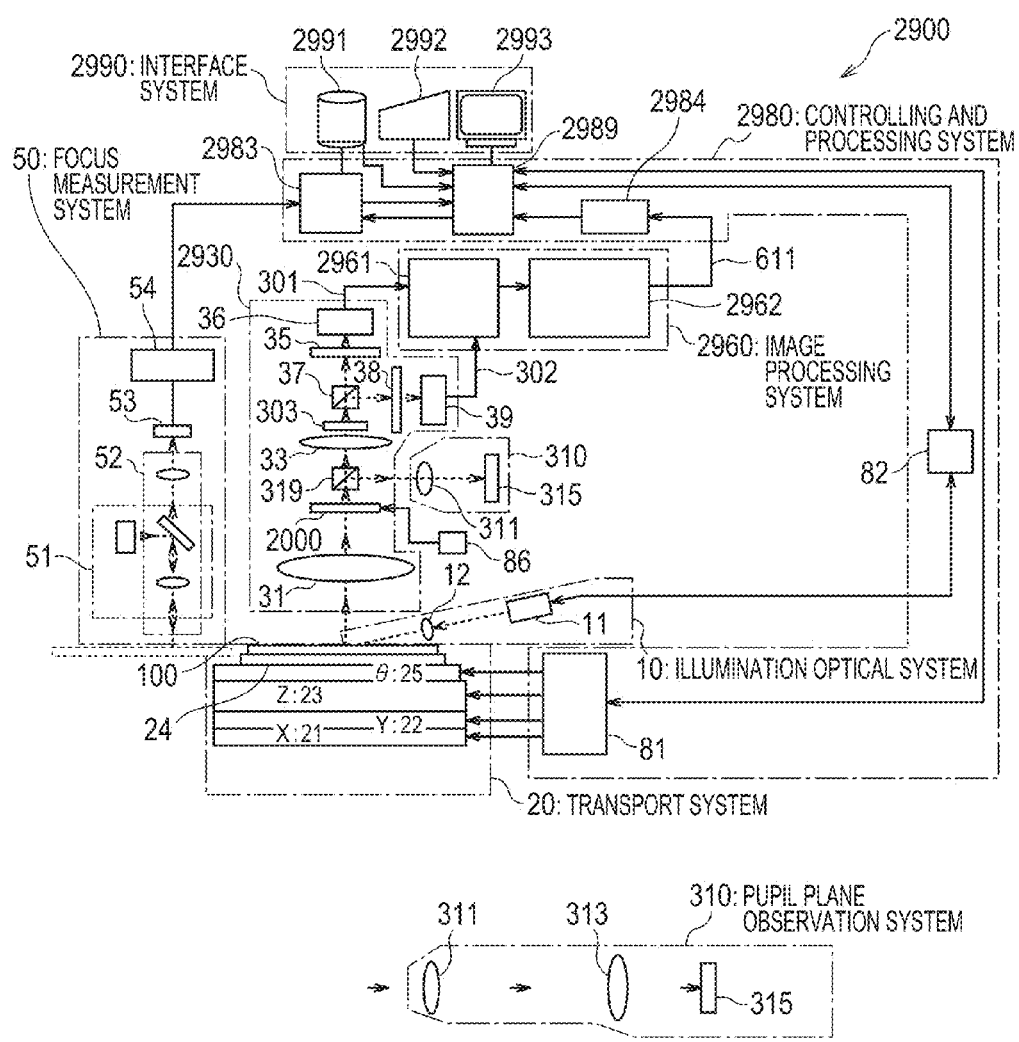
FIG. 50 is a block diagram showing a general configuration of an inspection apparatus which uses an optical filtering device according to a fifth embodiment.

FIG. 50 shows a fifth embodiment wherein an optical filtering device which uses a micro shutter array according to the present invention is applied to a dark-field inspection apparatus. The present embodiment is different from the first embodiment in configuration of a detection optical system 2930. Scattered light from the surface of a substrate 100 transmitted through the relay lens 33 is split into two polarized light components using a polarizing beam splitter 37 and imaged on the sensor 35 and another sensor 38. Light intensity distributions obtained by the imaging are converted into digital data by the A/D conversion units 36 and 39, and the digital data are processed by an image processing unit 2960. At this time, since light scattered from the substrate 100 includes scattered light of a polarized light component according to a pattern formed on the surface of the substrate 100 or a characteristic of a defect, outputs of the sensors 35 and 38 are suitably utilized to detect whether or not a defect exists.

The image processing system 2960 includes an inter-adjacent die image positional displacement information calculation unit 2961 and a data processing unit 2962 for carrying out a defect decision and detection process using an inter-die difference image. The inter-adjacent die image positional displacement information calculation unit 2961 and the data processing unit 2962 individually include a memory having a capacity sufficient to store image data therein.

A controlling and processing system 2980 at least includes a transport system controlling unit 81 for controlling the substrate transport system 20, an illumination light source controlling unit 82, and a sensor controlling unit 2983 for acquiring an image from a detection signal from the detection optical system 2930. The controlling and processing system 2980 further includes a defect information processing unit 2984 for carrying out a classification process of defect information 611 outputted from the image processing system 2960, and a control unit 2189 for controlling the entire controlling and processing system 2980. FIG. 50 shows also a power supply unit 86 including a control circuit for the optical filtering device 2000. Although the power supply unit 86 is connected to the control unit 2989, illustration of the same is omitted in FIG. 50.

An interface system 2990 at least includes a data accumulation section 2991 for accumulating defect information processed by and outputted from the controlling and processing system 2980, and an inputting section 2992 for carrying out inspection condition setting and controlling processing information inputting. The interface system 2990 further includes a display section 2993 for displaying defect information and displaying controlling processing information.

Embodiment 6

Figure 51:
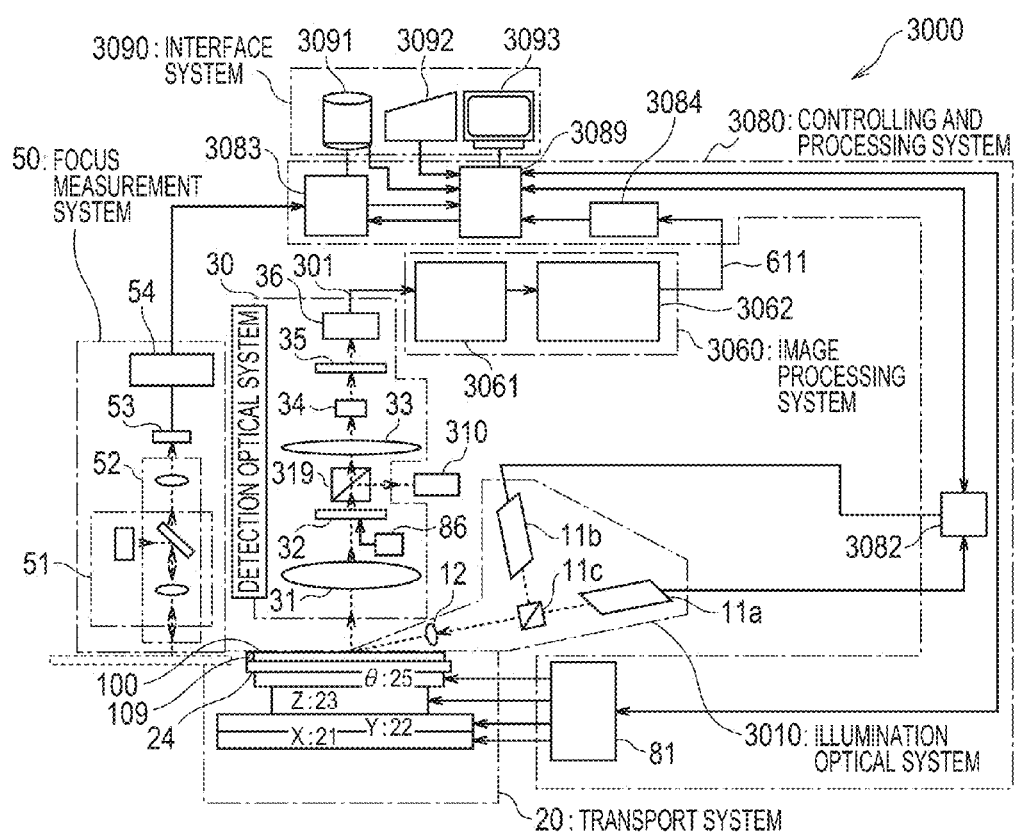
FIG. 51 is a block diagram showing a general configuration of an inspection apparatus which uses an optical filtering device according to a sixth embodiment.

FIG. 51 shows a sixth embodiment wherein an optical filtering device which uses a micro shutter array according to the present invention is applied to a dark-field inspection apparatus.

The present embodiment is configured such that, after beams emitted from a plurality of light sources 11a and 11b provided in an illumination optical system 3010 are guided to pass optical paths substantially same as each other using a beam splitter 11c once, they are irradiated on a substrate 100.

An image processing system 3060 includes an inter-adjacent die image positional displacement information calculation unit 3061 and a data processing unit 3062 for carrying out a defect decision and detection process using an inter-die difference image. The inter-adjacent die image positional displacement information calculation unit 3061 and the data processing unit 3062 individually include a memory having a capacity sufficient to store image data therein.

A controlling and processing system 3080 at least includes a transport system controlling unit 81 for controlling the transport system 20, an illumination light source controlling unit 3082, and a sensor controlling unit 3083 for acquiring an image from a detection signal from the detection optical system 30. The controlling and processing system 3080 further includes a defect information processing unit 3084 for carrying out a classification process of defect information 611 outputted from the image processing system 3060, and a control unit 3089 for controlling the entire controlling and processing system 3080. FIG. 51 shows also a power supply unit 86 including a control circuit for the optical filtering device 2000. Although the power supply unit 86 is connected to the control unit 3089, illustration thereof is omitted in FIG. 51.

An interface system 3090 at least includes a data accumulation section 3091 for accumulating defect information processed by and outputted from the controlling and processing system 3080, and an inputting section 3092 for carrying out inspection condition setting and controlling processing information inputting. The interface system 3090 further includes a display section 3093 for displaying defect information and displaying controlling processing information.

Embodiment 7

Figure 52:
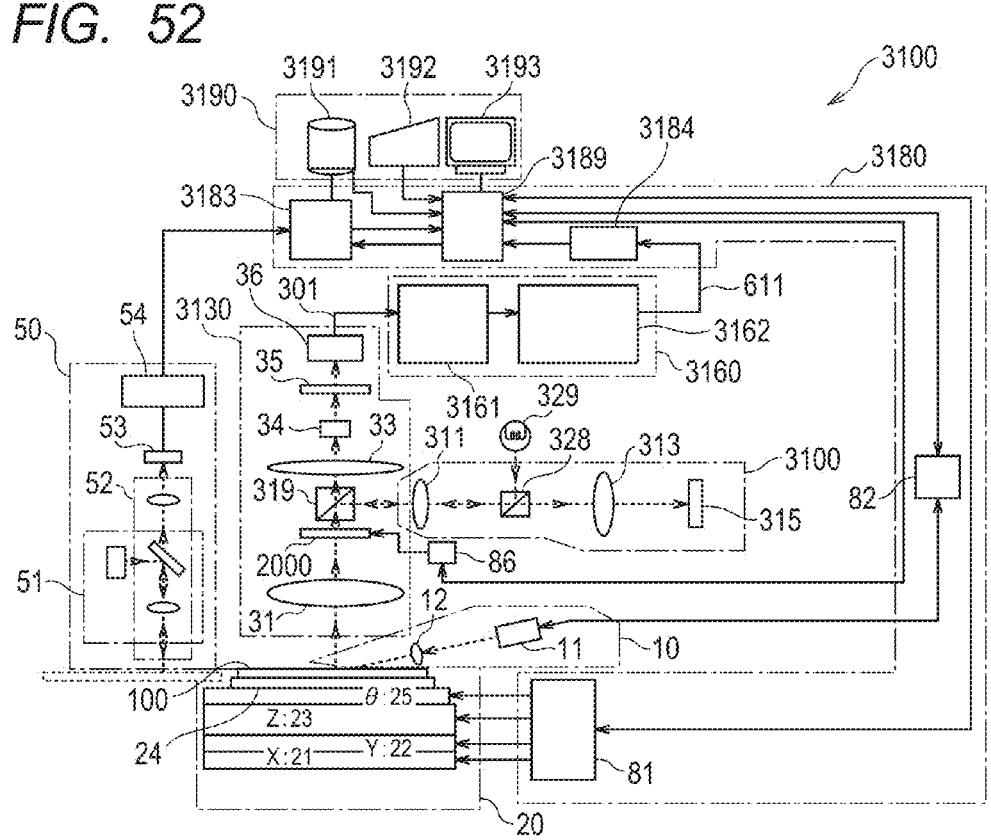
FIG. 52 is a block diagram showing a general configuration of an inspection apparatus which uses an optical filtering device according to a seventh embodiment.

FIG. 52 shows a seventh embodiment wherein an optical filtering device which uses a micro shutter array according to the present invention is applied to a dark-field inspection apparatus.

In the configuration described hereinabove with reference to FIG. 16A, the spatial filter 32 in which the expansion observation system 3210 is incorporated is used in the optical filtering device 2000. However, in the present embodiment, the first Fourier transform plane observation system 3100 includes the function of the expansion observation system 3210 described hereinabove with reference to FIG. 16A. In particular, the expanded Fourier transform plane observation system 3100 includes a light source 329 and a beam splitter 328 in addition to the Fourier transform plane observation system 310 of the first embodiment. Consequently, the optical axis of light emitted from the light source 329 is bent by the beam splitter 328 such that the light passes a route substantially coincident with the optical axis of the Fourier transport plane observation system of a detection optical system 3130.

The light thus passes through the lens 311 and the optical element 319 and illuminates the optical filtering device 2000. If reflected light 3214 from a noticed shutter 2001 arrives at the area sensor 315 and the shutter 2001 looks bright, then it is decided that the shutter 2001 is in a closed state, but if no reflected light arrives and the noticed shutter 2001 looks dark, then it is decided that the shutter 2001 is in an open state.

Here, the shutter 2001 in the latched closed state is inclined by $\Delta\theta$ with respect to a maximum angle of $\Delta\theta_{max}$ similarly as in the foregoing description given with reference to FIGS. 16A to 16E. Therefore, directly reflected light is reflected toward a direction displaced by $2 \times \Delta\theta_{max}$ from that at any other portion than the shutter. Therefore, it is necessary to use a lens having a sufficiently large aperture as the lens 311 so that also the reflected light may enter the lens 311. It is to be noted that the aperture of the lens 311 is so small that reflected light from a shutter in the latch closed state does not enter the aperture, the shutter 2001 looks totally dark, and therefore, the latched closed state cannot be distinguished from the open state.

It is to be noted that, in order to avoid mixture with the scattered light from diffracted scattered light from the surface of the inspection object substrate 100, it is preferable to take the following measures. In particular, in the flow chart shown in FIG. 22, when a substrate 100 is scanned (S2204) to acquire an optical image in the proximity of the surface of the inspection object substrate 100 (S2205), the light source 329 is turned off or light is blocked so that illumination light may not be irradiated upon the optical filtering device 2000.

An image processing system 3160 includes an inter-adjacent die image positional displacement information calculation unit 3161 and a data processing unit 3162 for carrying out a defect decision and detection process using an inter-die difference image. The inter-adjacent die image positional displacement information calculation unit 3161 and the data processing unit 3162 individually include a memory having a capacity sufficient to store image data therein.

A controlling and processing system 3180 at least includes a transport system controlling unit 81 for controlling the transport system 20, an illumination light source controlling unit 82, and a sensor controlling unit 3183 for acquiring an image from a detection signal from the detection optical system 30. The controlling and processing system 3180 further includes a defect information processing unit 3184 for carrying out a classification process of defect information 611 outputted from the image processing system 3160, and a control unit 3189 for controlling the entire controlling and processing system 3180. FIG. 52 shows also a power supply unit 86 including a control circuit for the optical filtering device 2000. The power supply unit 86 is connected to the control unit 3089.

An interface system 3190 at least includes a data accumulation section 3191 for accumulating defect information processed by and outputted from the controlling and processing system 3180, and an inputting section 3192 for carrying out inspection condition setting and controlling processing information inputting. The interface system 3190 further includes a display section 3193 for displaying defect information and displaying controlling processing information.

Embodiment 8

An eighth embodiment wherein an optical filtering device which uses a micro shutter array according to the present invention is applied to a dark-field inspection apparatus is described with reference to FIGS. 53A and 53B.

Figure 53A:
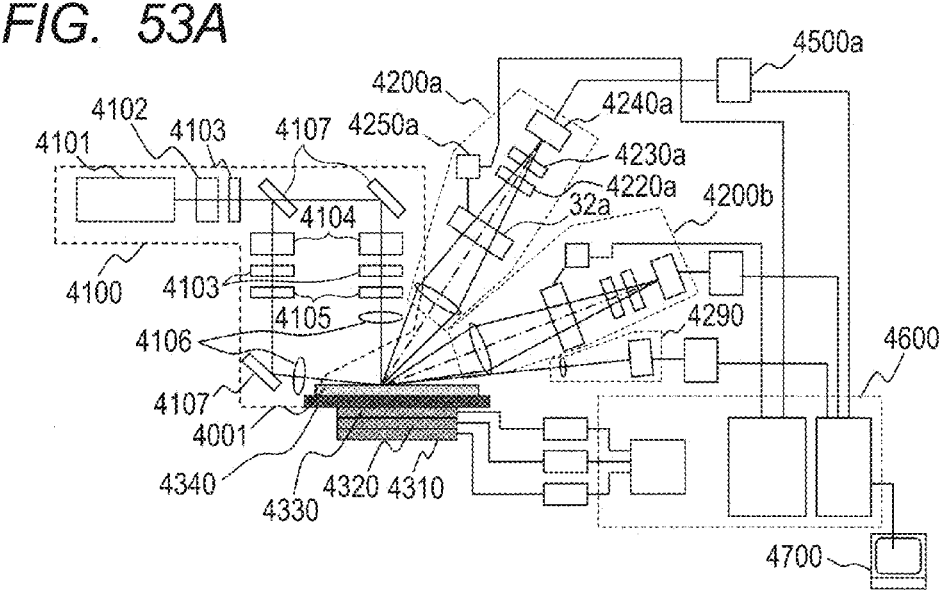
FIG. 53A is a block diagram of the front showing a general configuration of an inspection apparatus which incorporates an optical filtering device which uses a micro shutter array according to an eighth embodiment and inspects a wafer having no pattern formed thereon in a dark field.

The dark-field inspection apparatus according to the present embodiment is configured suitably using an illumination section 4100, a detection section 4200 (4200a to 4200f), a stage 4300 on which a specimen 4001 can be placed, a signal processing section 4500, an overall controlling section 4600, a display section 4700 and an inputting section 4800 as shown in FIG. 53A.

The signal processing section 4500 includes a defect decision section 4510, a feature value extraction section 4520, and a defect type and size decision section 4530. A regular reflection detection section 4290 is installed for large area defect inspection, specimen surface measurement and so forth as occasion demands. The illumination section 4100 is configured suitably using a laser light source 4101, an attenuator 4102, a polarizing element 4103, a beam expander 4104, an illuminance distribution controlling element 4105, a reflection mirror 4106, and a condenser lens 4107. A laser beam emitted from the laser light source 4101 is adjusted in intensity by the attenuator 4102, in polarization state by the polarizing element 4103 and in intensity distribution in an illumination light flux by the illuminance distribution controlling element 4105. Then, the laser beam is condensed to the proximity of the surface of the specimen 4001 using the reflection mirror 4106 and the condenser lens 4107 and irradiated upon the surface of the specimen.

Figure 59:
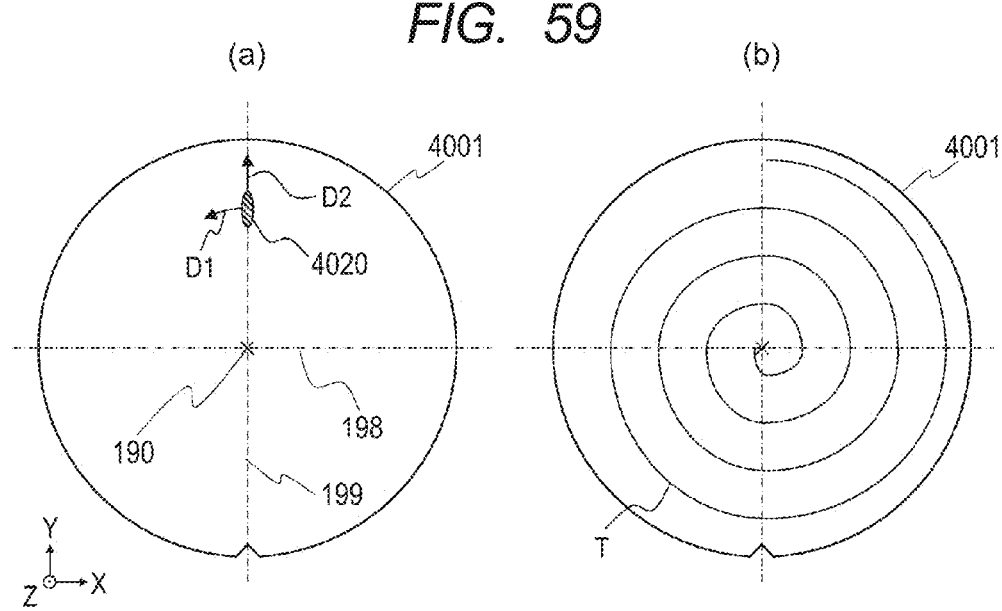
FIG. 59 is a schematic view illustrating a scanning method of an irradiation spot illuminated on the surface of a specimen.
Figure 60A:
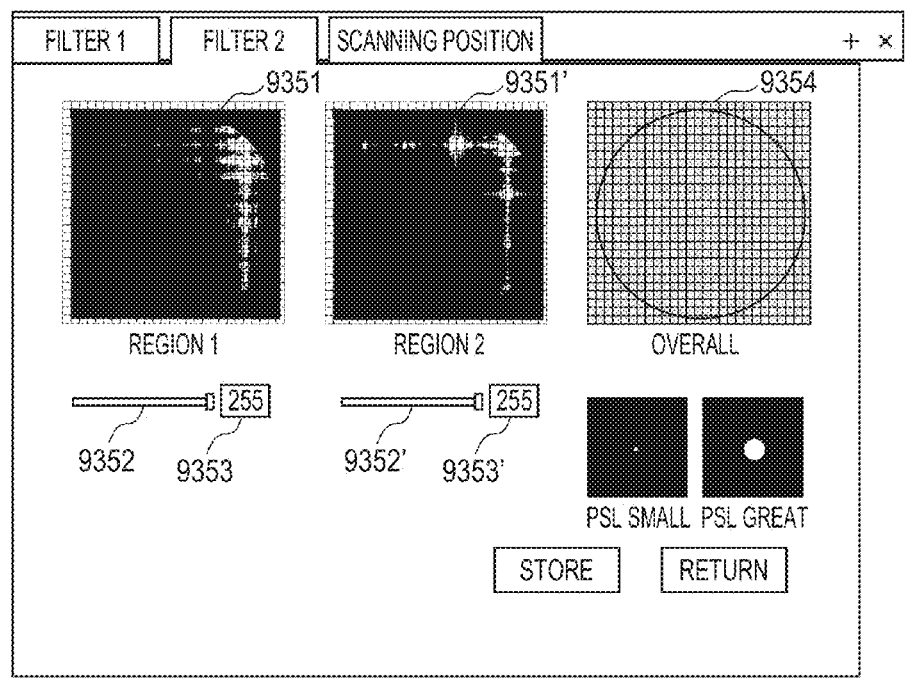
FIG. 60A is a front view of a screen image illustrating a diffracted light intensity distribution on the Fourier transform plane before setting of a spatial filter on a user interface for setting a light blocking region by the inspection apparatus which incorporates the optical filtering device which uses the micro shutter array according to the eighth embodiment of the present invention and inspects a wafer having no pattern formed thereon in a dark field.
Figure 60B:
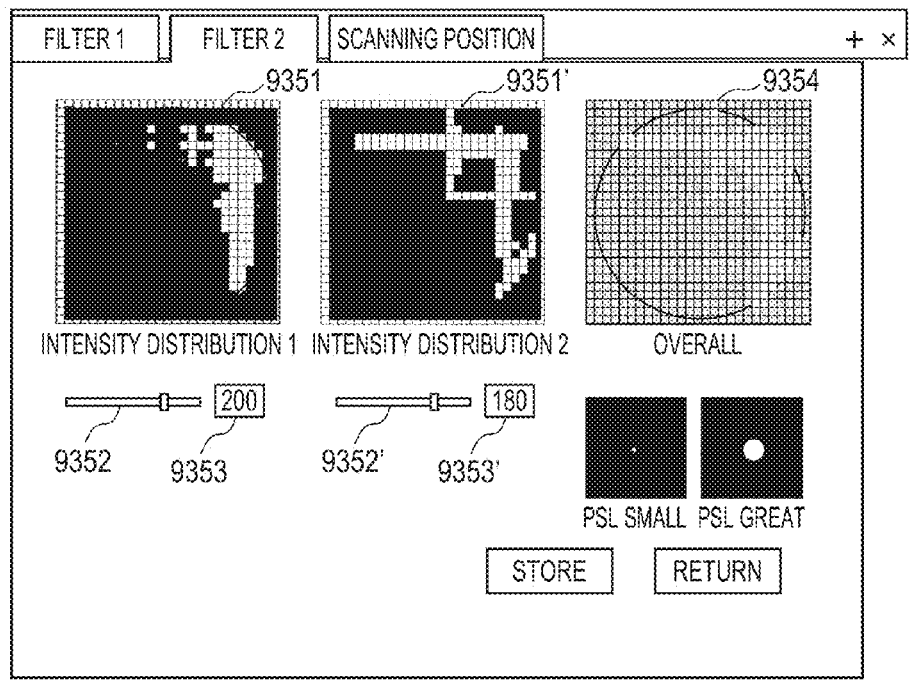
FIG. 60B is a front view of a screen image showing, in a second modification to the inspection apparatus which incorporates the optical filtering device which uses the micro shutter array according to a form of the first embodiment and inspects a wafer having no pattern formed thereon in a dark field, a spatial filter setting region for blocking light by the optical filtering device on a user interface for light blocking region setting.
Figure 61:
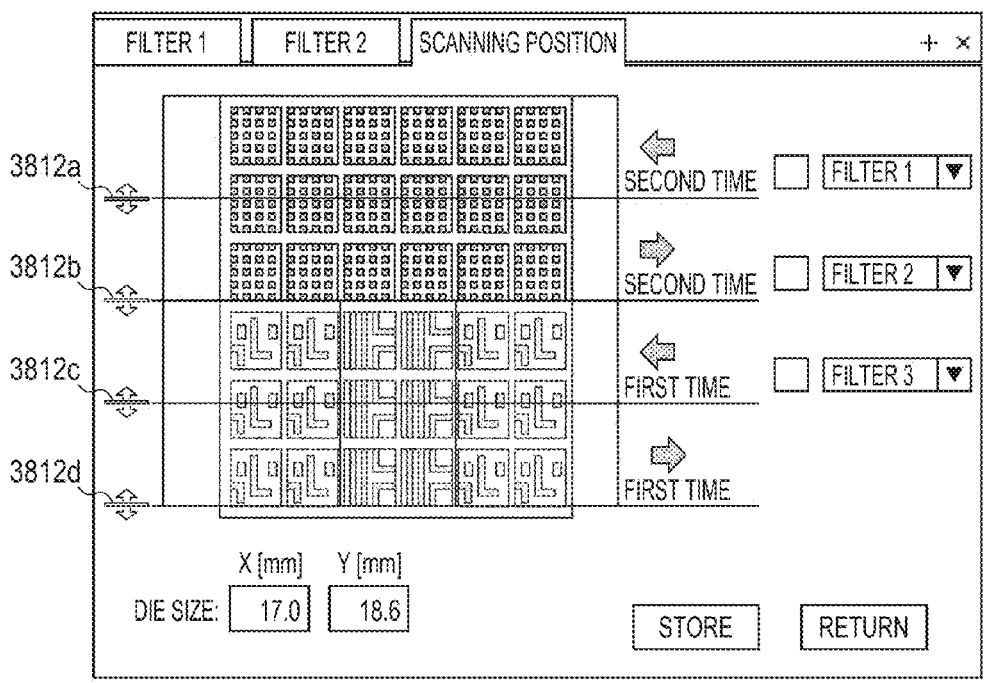
FIG. 61 is a front view illustrating an embodiment of a user interface for setting a scanning position and a combination of the scanning position and a light blocking region by the second modification to the inspection apparatus which incorporates the optical filtering device which uses the micro shutter array according to the form of the first embodiment of the present invention.

The stage 4300 includes a translation stage 4310, a rotational stage 4320, a Z stage 4330, and a substrate supporting mechanism 4340. FIG. 59 illustrates a relationship between an illumination region (illumination spot 4020) on the specimen 4001 and a scanning direction by movement of the rotational stage 4320 and the translation stage 4310 and a locus of the illumination spot 4020 drawn on the specimen 4001.

The illumination spot 4020 is scanned in a circumferential direction D1 of a circle centered at the axis of rotation of the rotational stage 4320 by rotational movement of the rotational stage 4320 and a translation direction D2 of the translation stage 4310 by translation movement of the translation stage 4310. The illumination section 4100 is configured such that the longitudinal direction of the illumination spot 4020 is parallel to the scanning direction D2 and the illumination spot 4020 passes the axis of rotation of the translation stage 4310 by the scanning in the scanning direction D2. The Z stage is moved such that the surface of the specimen 4001 is positioned at an appropriate position. By the configuration described above, while the specimen 4001 makes one rotation by the scanning in the scanning direction D1, the illumination spot 4020 scans in the scanning direction D2 over a distance smaller than the length thereof in the longitudinal direction. As a result, the illumination spot 4020 draws a spiral locus T, and the specimen 4001 is scanned over the overall area thereof.

Figure 53B:
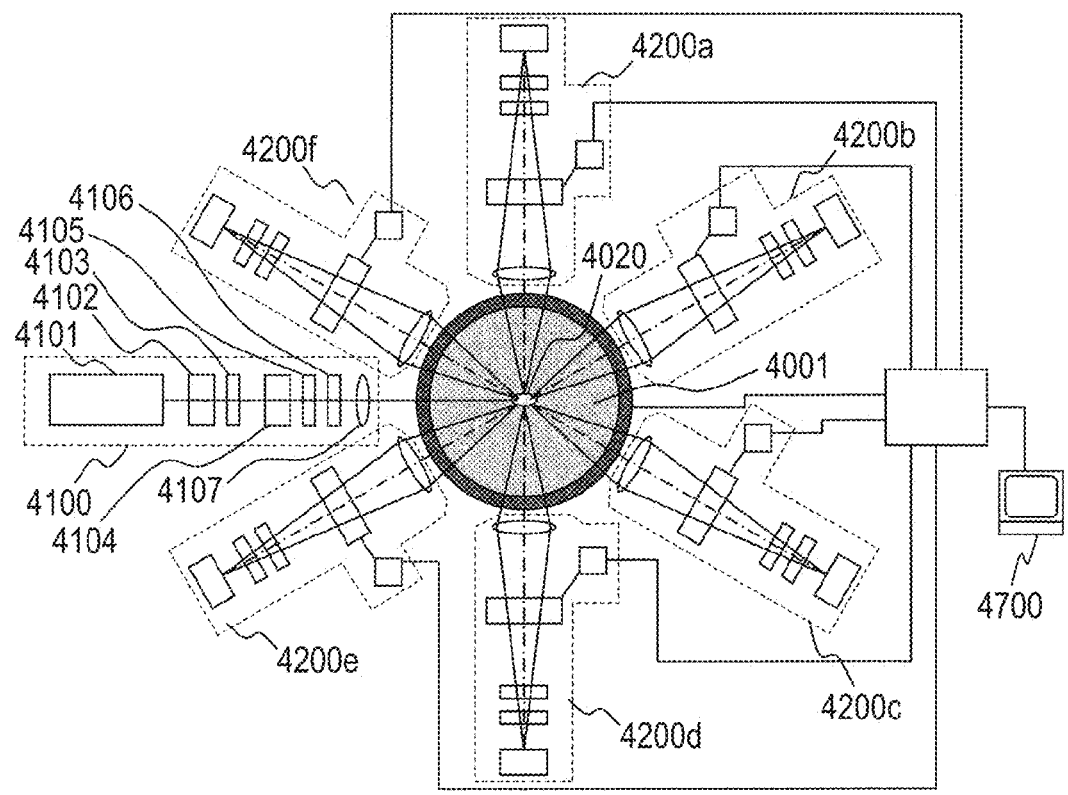
FIG. 53B is a diagram illustrating a block diagram of a plan and showing a general configuration of the inspection apparatus which incorporates the optical filtering device which uses the micro shutter array according to the eighth embodiment and inspects a wafer having no pattern formed thereon in a dark field.

The detection section 4200 is configured such that it includes a plurality of detection sections 4200a to 4200f as shown in FIG. 53B and condenses and detects scattered light scattered by the surface of the specimen 4001 and propagating in different orientations and elevation directions from each other.

A detailed configuration of the detection sections 4200a to 4200f is described using the detection section 4200a.

The detection section 4200a is configured suitably using a collector optics 4210a, a two-dimensional spatial filter system 32a, a polarizing filter 4220a, and a sensor 4230a. An image of an illumination spot 4020 is formed on or in the proximity of a light receiving face of the sensor 4230a by the collector optics 4210a. Thereupon, it is possible to use the two-dimensional spatial filter system 32a to block light scattered to a desired direction. The polarizing filter 4220a can be inserted into and removed from the optical axis of the collector optics 4210a. The sensor 4230a is configured suitably using a photomultiplier tube, an avalanche photodiode, a semiconductor detector coupled to an image intensifier, or the like.

After a scattered light signal detected by the detection section 4200 is subjected to processes such as A/D conversion, it is transmitted to the signal processing section 4500. In the signal processing section 4500, the defect decision section 4510 decides an existing place of a defect. With regard to a place decided as a defect, a feature value is extracted by the feature value extraction section 4520. The feature value is sent to the defect type and size decision section 4530, by which a defect type and a defect size are decided. A result of the decision is sent to the overall controlling section 4600 and is outputted in a form in which it can be confirmed by an operator of the apparatus from the display section 4700.

In the optical system of the present embodiment, scattered light by surface roughness of a semiconductor wafer or the like is detected by the detection optical system similarly as in the description in Patent Document 8 (JP-A-2010-2406). On the other hand, when it is desired to detect a foreign article placed on the surface of a substrate or a defect of the surface of a substrate with a high sensitivity, the surface roughness makes a cause of background noise.

Figure 54A:
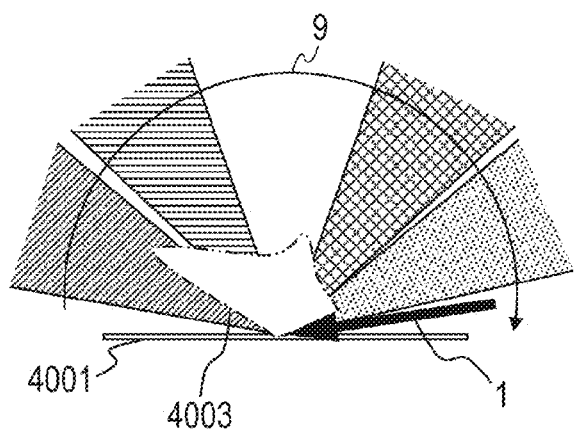
FIG. 54A is an image view illustrating a distribution of scattered light scattered by components of high spatial frequencies by surface roughness of a specimen when illumination light is irradiated upon a specimen.
Figure 54B:
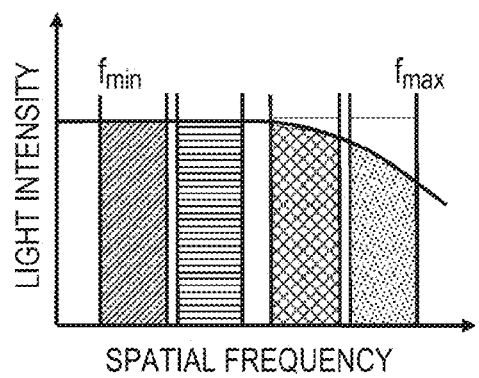
FIG. 54B is a graph illustrating a relationship between a spatial frequency and a light intensity of scattered light scattered by components having high spatial frequencies by surface roughness of a specimen.
Figure 54C:
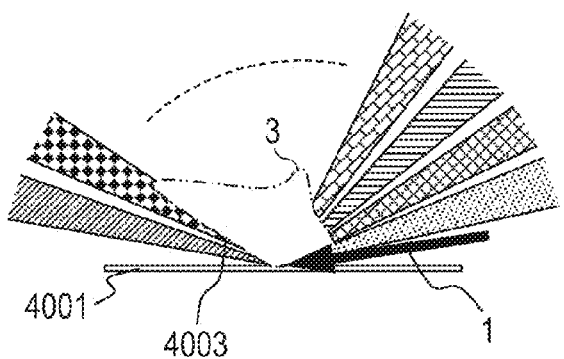
FIG. 54C is an image view illustrating a distribution of scattered light scattered by components having low spatial frequencies by surface roughness of a specimen when illumination light is irradiated upon a specimen.
Figure 54D:
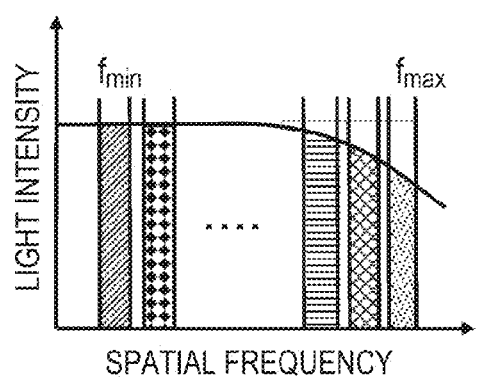
FIG. 54D is a graph illustrating a relationship between a spatial frequency and a light intensity of scattered light scattered by components having low spatial frequencies by surface roughness of a specimen.

FIGS. 54A to 54D show an image which indicates in what distribution 4003 scattered light by the surface roughness of the specimen 4001 is distributed when an illumination 1 is irradiated upon the specimen 4001. The illumination 1 is scattered in various directions in response to the spatial frequency of the surface roughness which contributes to the light scattering. Such light scattered by a component of the specimen 4001 having a high spatial frequency as shown in FIG. 54A is scattered in a direction near to the direction of direct reflection of the illumination light 1 (FIG. 54B). Meanwhile, such light scattered by a component having a low spatial frequency as shown in FIG. 54C is scattered in a direction near to the incidence direction of the illumination light 1 (FIG. 54D).

Here, since the degree of the surface roughness arises from a process in wafer fabrication or wafer reclamation, it may be considered that, for example, within the same lot, it little varies. If the degree of the surface roughness does not vary, then the scattering direction of the scattered light arising from the surface roughness does not vary.

In the present embodiment, the scattering direction of scattered light arising from surface roughness is acquired in advance, and the optical filtering device 2000 of the present invention is used to block scattered light arising from the surface roughness. As a result, a foreign article placed on the surface of a substrate or a defect on the surface of a substrate can be detected with a high sensitivity.

Figure 55A:
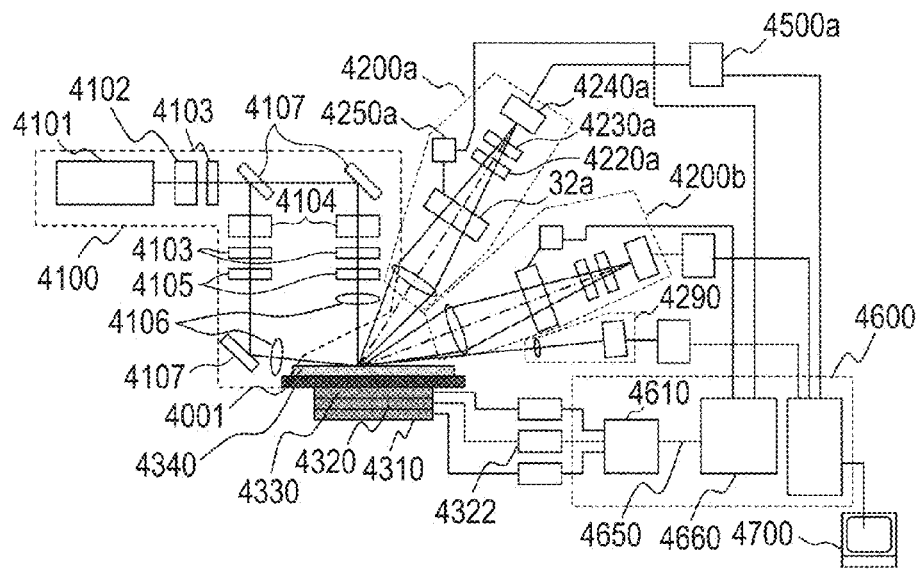
FIG. 55A is a block diagram of the front showing a general configuration of an inspection apparatus which incorporates an optical filtering device which uses a micro shutter array according to a modification to the eighth embodiment and inspects a wafer having no pattern formed thereon in a dark field.
Figure 55B:
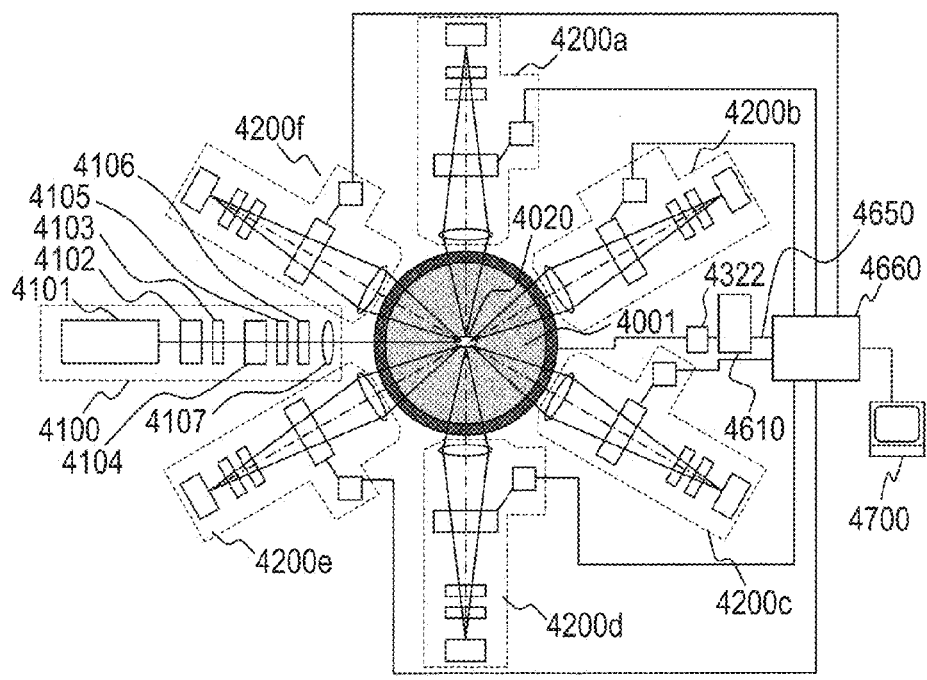
FIG. 55B is a block diagram of a plan showing a general configuration of the inspection apparatus which incorporates the optical filtering device which uses the micro shutter array according to the modification to the eighth embodiment and inspects a wafer having no pattern formed thereon in a dark field.

Now, a modification to the configuration of the embodiment 8 is described with reference to FIGS. 55A and 55B. The present modification is configured such that, in order that driving circuits 4250a to 4250f of the spatial filters 32a to 32f can dynamically change a light blocking region in synchronism with an output of a rotational angle outputting device 4322 of the rotational stage 4320, a signal line 4650 is additionally provided between a stage driver 4610 and a spatial filter driving circuit controlling system 4660.

It is known that, in a silicon wafer which has an epitaxial growth film of silicon on the surface thereof (wafer on the surface of which no pattern is formed, hereinafter referred to simply as "silicon epitaxial wafer"), differences in level which corresponds to the thickness of an atomic layer called terrace are juxtaposed in a substantially same direction. (JP-A-2006-100596, "Step Pattern Formation on Si Vicinal Surfaces with Two Coexisting Structures", M. Uwaha, http://www.ims.nus.edu.sg/Programs/nanoscale/files/muwahal.pdf)

Therefore, it is known that, when white illumination is irradiated upon a silicon epitaxial wafer, the wafer looks in the rainbow colors. It is known that, by a cause same as that of this phenomenon, when a laser beam is illuminated on a silicon epitaxial wafer, intense scattered light is generated from a direct reflection direction of the illumination light from the surface of the wafer toward the juxtaposition direction of the terraces. In other words, if a silicon epitaxial wafer is rotated while a laser beam is irradiated upon the wafer, then the direction in which intense scattered light is emitted varies in response to the direction of the wafer. However, since terraces on a silicon epitaxial wafer are not defects, there are strong needs that the terraces be not detected as detects.

Therefore, the present embodiment is configured such that the light blocking region of the optical filtering device 2000 is changed in accordance with rotation of a wafer to make it possible to block intense scattered light generated by a cause of different level portions of terraces while the other scattered light can be detected by an optical sensor of a high sensitivity such as a photomultiplier tube. With the configuration, it is possible to efficiently detect a foreign article and a defect on a silicon epitaxial wafer.

Figure 57:
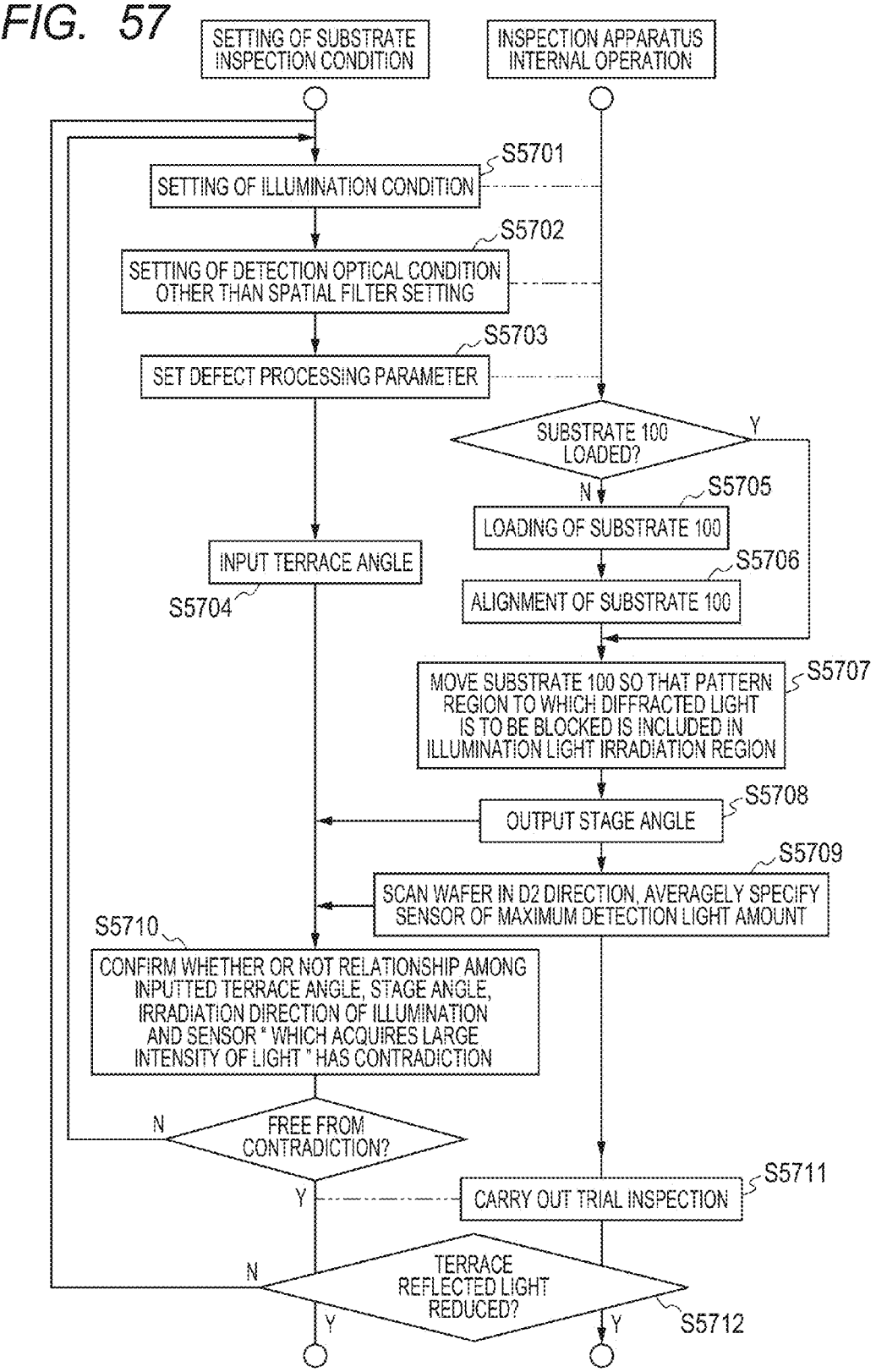
FIG. 57 is a flow chart illustrating a flow of processing for setting substrate inspection conditions by the inspection apparatus which incorporates the optical filtering device which uses the micro shutter array according to the modification to the eighth embodiment and inspects a wafer having no pattern formed thereon in a dark field.

A setting flow of substrate inspection conditions where the inspection apparatus according to the present invention is used is shown in FIG. 57.

First, illumination conditions such as an illumination angle (orientation, elevation) and illumination polarization (S5701). Detection optical conditions other than the spatial filter setting (optical magnification, presence or absence of light analysis and so forth) are set (S5702). Defect processing parameters are set (S5703). If an inspection object wafer 100 is not yet loaded in the apparatus, then a wafer 100 is loaded (S5705), and alignment is carried out using notches or an orientation flat (S5706). The wafer is moves so that a region including terraces on the epitaxial wafer is included in the irradiation region of illumination light (S5707).

Figure 56A:
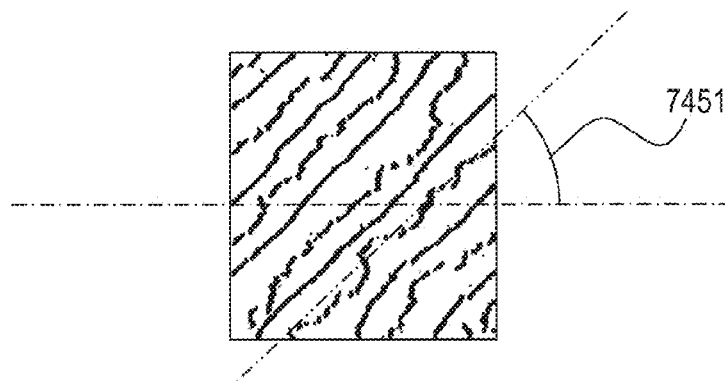
FIG. 56A is a plan view in which a surface structure of a silicon epitaxial wafer is displayed in an enlarged scale.
Figure 56B:
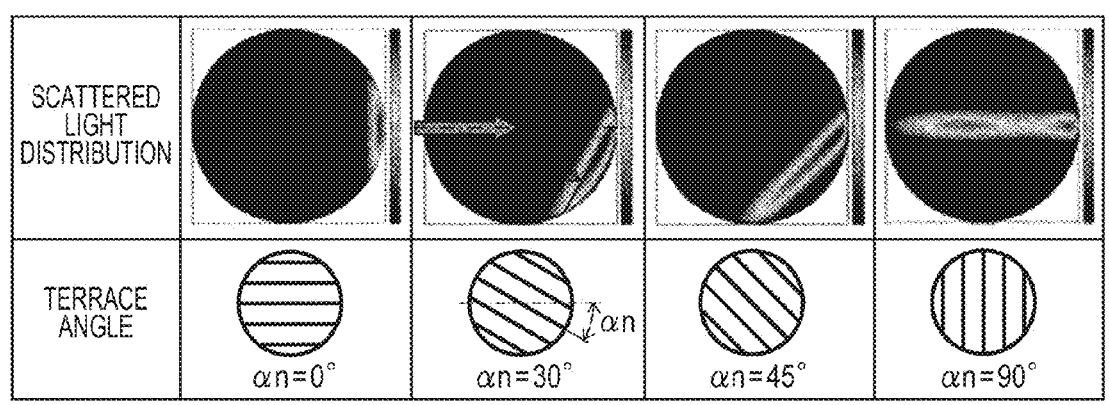
FIG. 56B is a table in which relationships between a distribution of scattered light and an angle of a terrace of a silicon epitaxial wafer when illumination light is irradiated from a direction of an arrow mark upon a silicon epitaxial wafer.

As shown in FIG. 56A, the direction 7451 of the terraces is displaced by approximately 5 to 15 degrees with respect to the horizontal direction of the wafer. It is known that this displacement differs depending upon the growth method of the crystal. This value is inputted (S5704). Here, a stage angle is obtained (S5708), and while the wafer is scanned in the D2 direction indicated in FIG. 59, light diffracted by the terraces on the epitaxial wafer is detected and the sensor which indicates a maximum average detection light intensity is specified (S5709). Then, it is confirmed whether or not the terrace angle 7451 and the stage angle, the irradiation direction of the illumination and the sensor which exhibits the maximum detection light intensity have an inconsistent relationship thereamong (S5710). If they are inconsistent, then since the setting of the optical system or the input value of the terrace angle is wrong, the processing returns to S4601 of the procedure.

The wafer is trial-inspected using the inspection conditions set as described above (S5711), and if it can be confirmed that the diffracted light from the terraces exhibits decrease (S5712), then the substrate inspection condition setting is ended. If the defect detection sensitivity is insufficient, then the processing returns to the setting of illumination conditions (S5701) to modify the set conditions.

Figure 58:
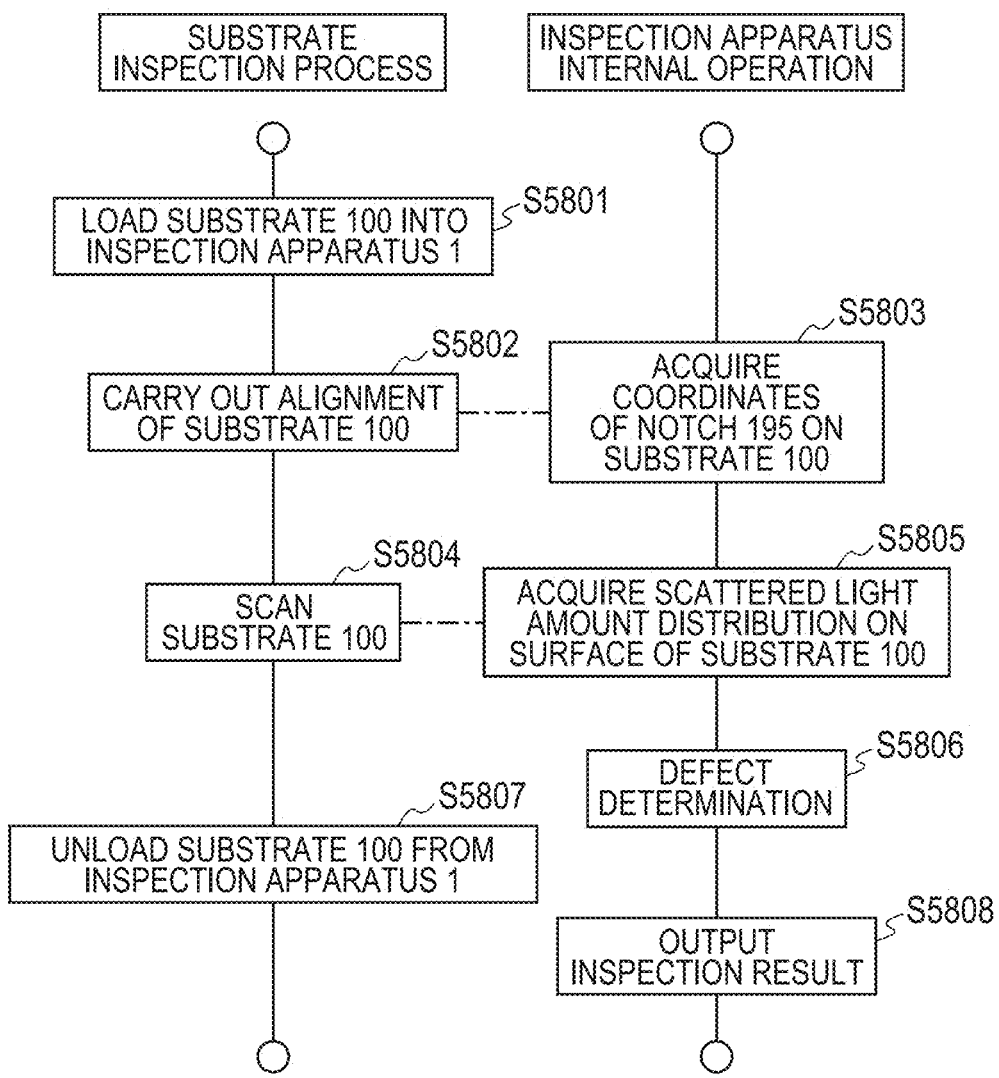
FIG. 58 is a flow chart illustrating a flow of processing for picking up an image of the surface of a substrate by the inspection apparatus which incorporates the optical filtering device which uses the micro shutter array according to the modification to the eighth embodiment and inspects a wafer having no pattern formed thereon in a dark field.

A flow chart of the substrate inspection procedure using the inspection apparatus according to the eighth embodiment of the present invention is shown in FIG. 58.

A substrate 100 is loaded into the inspection apparatus 1 (S5801) and held by the substrate chuck 24. The inspection apparatus 1 executes alignment of the substrate 100 (S5802) and acquires coordinates of notches 195 on the aligned substrate 100 (S5803) to detect an angle defined by the angle of the substrate 100 and a reference direction of the rotational stage.

Then, the substrate 100 is scanned as indicated in FIG. 59 (S5804), and light scattered from the surface of the substrate 100 is detected and a light intensity distribution of the light is acquired (S5805). Based on the acquired distribution, a defect decision process (S5806) for deciding whether or not a defect and a foreign article exist in the proximity of the surface of the inspection object substrate 100 is carried out. Then, the substrate 100 is unloaded from the inspection apparatus 1 (S5807), and a defect detection result of the substrate 100 is outputted (S5808).

FIG. 59 illustrates a relationship between the illumination region (illumination spot 4020) on the specimen 4001 and the scanning direction by movements of the rotational stage 4320 and the translation stage 4310 and a locus of the illumination spot 4020 drawn on the specimen 4001 by the scanning.

The illumination spot 4020 is scanned in the circumferential direction D1 of a circle centered at the axis of rotation of the rotational stage 4320 by rotational movement of the rotational stage 4320 and in the translation direction D2 of the translation stage 4310 by the translation movement of the translation stage 4310. The illumination section 4100 is configured such that the longitudinal direction of the illumination spot 4020 is parallel to the translation direction D2 and the illumination spot 4020 passes the axis of rotation of the translation stage 4310 by the scanning in the translation direction D2. The Z stage is moved so that the surface of the specimen 4001 is positioned at a suitable position.

By the configuration described above, while the specimen 4001 makes one rotation by the scanning in the circumferential direction D1, the illumination spot 4020 scans in the translation direction D2 over a distance smaller than the length thereof in the longitudinal direction. Consequently, the illumination spot 4020 draws a spiral locus T, and the specimen 4001 is scanned over the overall area thereof.

Although the invention made by the present inventor has been particularly described above based on the embodiments thereof, the present invention is not limited to the embodiments described above but includes various modifications. For example, it is possible to replace some component of a certain embodiment with a component of another embodiment without departing from the spirit and scope of the invention, and also it is possible to add some component of a certain embodiment to a component of another embodiment. Further, it is possible to add, delete or replace some other publicly known component to, from or with some component of any embodiment.

DESCRIPTION OF THE REFERENCE CHARACTERS

1 . . . Apparatus main body, 100 . . . Inspection object substrate, 10 . . . Illumination optical system, or first illumination optical system, 20 . . . Substrate transport system, 30 . . . Defect detection optical system (upper), 40 . . . Defect detection optical system (oblique), 50 . . . Focus measurement system, 60 . . . Image processing system, 80 . . . Overall controlling system, 90 . . . Interface system, 91 ... Storage section, 92 ... Inputting and outputting means (including also a keyboard and a network), 93 ... Display means, 11 ... Laser light source, 12 ... Beam shaping lens, 13 ... Polarization controlling element, 14 ... Polarization controlling element driver, 18, 78 ... Illumination beam, 19, 79 ... Illumination region of sample surface, 21 ... X stage, 22 ... Y stage, 23 ... Z stage, 24 ... Substrate fixing and supporting portion (wafer chuck), 25 ... θ stage, 31 ... Objective lens, 32 ... Spatial filter, 33 ... Imaging lens, 34 ... Polarizing filter, 35 ... Optical sensor, 36 ... A/D conversion unit, 62 ... Defect decision and detection unit, 109 ... Point light source, 2000 ... Optical filtering device, 2100 ... Micro shutter array, 2010 ... Unit shutter, 2001 ... Unit shutter, 2002 ... Working electrode, 2003 ... Suspension, 2004 ... Aperture, 2006, 2007 ... Incision, 2008 ... Protrusion of shutter, 2014 ... Oxide insulating film portion, 2016 ... SOI portion, 2017 ... Groove, 2020 ... Glass window material with wiring line, 2021, 2021', 2023 ... Wiring pattern, 2022 ... Light blocking pattern, 2200 ... Power supply unit (including a driving circuit)

The invention claimed is:

1. A defect inspection apparatus, comprising:
   illuminator which illuminates an inspection object substrate;
   detection optical unit including an optical filtering device which blocks scattered light from a portion of the inspection object substrate which is not desired to be detected as a defect, and detects scattered light from the portion of the inspection object substrate which is not blocked by the optical filtering device;
   signal processing unit which processes a signal obtained by the detection of the scattered light by the detection optical unit to detect a defect of the inspection object substrate; and
   outputting unit which outputs information of the defect detected by the signal processing unit,
   wherein, the optical filtering device of the defect inspection apparatus including:
   a shutter array which has shutter patterns formed in a two-dimensionally arrayed relationship on an optically opaque thin film produced on a SOI wafer and working electrodes formed on remaining portion of the SOI wafer which is removed at portions lower sides of the shutter patterns to form perforation portions;
   a glass substrate having electrode patterns formed on the surface thereof and having the shutter array mounted thereon; and
   a power supply section for supplying electric power to the electrode patterns formed on the glass substrate and the working electrodes of the SOI wafer,
   wherein the electric power to be supplied from the power supply section to the electrode patterns and the working electrodes being controlled to cause the shutter patterns formed in the two-dimensionally arrayed relationship to carry out opening and closing movements with respect to the perforation portions.

2. The defect inspection apparatus according to claim 1, wherein the inspection object substrate has regular circuit patterns formed on the surface thereof, and the optical filtering device blocks, from among the scattered light from the inspection object substrate illuminated by the illuminator, intense scattered light generated from the regular circuit patterns.

3. The defect inspection apparatus according to claim 1, wherein the inspection object substrate is a silicon epitaxial wafer, and the optical filtering device blocks, from among the scattered light from the silicon epitaxial wafer illuminated by the illuminator, intense scattered light generated from fine differences in level on the surface of the silicon epitaxial wafer.

4. The defect inspection apparatus according to claim 1, wherein the shutter patterns of the optical filtering device have two protrusions at end portions thereof.

5. The defect inspection apparatus according to claim 1, wherein wiring patterns are formed on a face of the glass substrate of the optical filtering device opposing to the face on which the electrode patterns are formed, and the wiring patterns have a recessed portion at a position thereof corresponding to the position of the protrusions of the shutter patterns.

6. The defect inspection apparatus according to claim 5, wherein the electrode patterns formed on the glass substrate are disposed at positions corresponding to the positions of the recessed portions of the wiring patterns formed on the glass substrate.

7. The defect inspection apparatus according to claim 1, wherein the power supply section controls a potential difference between the shutter patterns and the electrode patterns or the working electrodes such that a potential difference between the shutter patterns and the working electrodes when the shutter patterns are operated to open is more than a potential difference between the shutter patterns and the electrode patterns when the shutter patterns are operated to be closed.

8. A defect inspection method, comprising:
   illuminating an inspection object substrate;
   blocking with an optical filtering device, scattered light from a portion of the inspection object substrate which is not desired to be detected as a defect among scattered light from the illuminated inspection object substrate, and detecting scattered light which is not blocked by the optical filtering device;
   processing a signal obtained by the detection of the scattered light to detect a defect of the inspection object substrate with a processor; and
   outputting information of the detected defect from an outputting unit,
   wherein in the step of blocking, the scattered light from the portion of the inspection object substrate which is not desired to be detected as a defect being carried out such that controlling electric power to be supplied to working electrodes and electrode patterns to drive shutter patterns, which can carry out opening and closing movements with respect to perforation portions, to close a desired one or more of the shutter patterns to block the scattered light, the shutter patterns are formed in a two-dimensionally arrayed relationship on an optically opaque thin film on a SOI wafer as a shutter array and the working electrodes are formed on the SOI wafer at perforation portions which are processed by removing portion on the SOI wafer which are under portions lower sides of the shutter patterns, and the electrode patterns are formed on a surface of a glass substrate on which the shutter array is mounted.

9. The defect inspection method according to claim 8, wherein the inspection object substrate has regular circuit patterns formed on the surface thereof, and the optical filtering device blocks, among the scattered light from the inspection object substrate illuminated by the illumination means, intense scattered light generated from the regular circuit patterns, by closing the desired shutter pattern or patterns.

10. The defect inspection method according to claim 8, wherein the inspection object substrate is a silicon epitaxial wafer, and the optical filtering device blocks, among the scattered light from the illuminated silicon epitaxial wafer, intense scattered light generated from fine differences in level on the surface of the silicon epitaxial wafer, by closing the desired shutter pattern or patterns.

11. The defect inspection method according to claim 8, wherein a potential difference between the shutter patterns and the electrode patterns or the working electrodes is controlled such that a potential difference between the shutter patterns and the working electrodes when the shutter patterns are operated to open is more than a potential difference between the shutter patterns and the electrode patterns when the shutter patterns are operated to be closed.

* * * * *